US012613246B2

(12) United States Patent
Zhu et al.

(10) Patent No.: US 12,613,246 B2
(45) Date of Patent: *Apr. 28, 2026

(54) FLUORESCENT PROBE AND PROTEIN LABELING METHOD

(71) Applicant: SHANGHAI GLORY CAPITAL MANAGEMENT LTD., Shanghai (CN)

(72) Inventors: Linyong Zhu, Shanghai (CN); Yi Yang, Shanghai (CN); Bingkun Bao, Shanghai (CN); Ni Su, Shanghai (CN); Dasheng Zhang, Shanghai (CN); Xianjun Chen, Shanghai (CN); Qiuning Lin, Shanghai (CN); Chunyan Bao, Shanghai (CN)

(73) Assignee: FLUORESCENCE DIAGNOSIS (SHANGHAI) BIOTECH COMPANY LTD., Shanghai (CN)

( * ) Notice: Subject to any disclaimer, the term of this patent is extended or adjusted under 35 U.S.C. 154(b) by 1480 days.

This patent is subject to a terminal disclaimer.

(21) Appl. No.: 17/250,061

(22) PCT Filed: Apr. 30, 2019

(86) PCT No.: PCT/CN2019/085192

§ 371 (c)(1),
(2) Date: Jun. 4, 2021

(87) PCT Pub. No.: WO2019/218876

PCT Pub. Date: Nov. 21, 2019

(65) Prior Publication Data

US 2021/0382060 A1 Dec. 9, 2021

(30) Foreign Application Priority Data

May 18, 2018 (CN) ........................ 201810485224.4

(51) Int. Cl.
*G01N 33/58* (2006.01)
*G01N 21/64* (2006.01)
(Continued)

(52) U.S. Cl.
CPC ....... *G01N 33/582* (2013.01); *G01N 21/6428* (2013.01); *G01N 33/68* (2013.01);
(Continued)

(58) Field of Classification Search
CPC .. G01N 33/582; G01N 21/6428; G01N 33/68; G01N 2021/6439
See application file for complete search history.

(56) References Cited

U.S. PATENT DOCUMENTS 11,209,437 B2 * 12/2021 Zhu ...................... C07D 473/18
2019/0187144 A1 * 6/2019 Zhu ...................... C07D 473/18

FOREIGN PATENT DOCUMENTS

CN 104745177 A 7/2015
CN 107641121 A 1/2018
WO WO-2018014821 A1 * 1/2018 ............. A61K 49/00

OTHER PUBLICATIONS

Leng, S. et al. "SNAP-tag fluorogenic probes for wash free protein labeling," Chinese Chemical Letters 28 (2017) 1911-1915 (Year: 2017).*

(Continued)

*Primary Examiner* — Jennifer Wecker
*Assistant Examiner* — Michelle Adams
(74) *Attorney, Agent, or Firm* — HAUPTMAN HAM, LLP

(57) ABSTRACT

Provided are a fluorescent probe, a preparation method therefor and a use thereof. The fluorescent probe sensitively and specifically responds to viscosity, and can be used for the specific fluorescence labeling of proteins as well as in the
(Continued)

quantification, detection or kinetic study of proteins and the imaging of cells, tissues and living bodies.

11 Claims, 6 Drawing Sheets

(51) Int. Cl.
*G01N 33/68* (2006.01)
*C07D 239/47* (2006.01)
*C07D 473/18* (2006.01)

(52) U.S. Cl.
CPC ......... *C07D 239/47* (2013.01); *C07D 473/18* (2013.01); *G01N 2021/6439* (2013.01)

(56) References Cited

OTHER PUBLICATIONS

International Search Report and Written Opinion mailed Jul. 26, 2019 in International Application No. PCT/CN2019/085192, filed Apr. 30, 2019.

* cited by examiner

FLUORESCENT PROBE AND PROTEIN LABELING METHOD

TECHNICAL FIELD

The present invention relates to a fluorescent probe, and a preparation method and use thereof.

BACKGROUND ART

Fluorescence specific labeling is a powerful tool for studying and quantifying protein function. Contrast to other study methods, fluorescent labeling has such irreplaceable advantages as being sensitive, in situ, instant, and visual. Currently, the most common method of fluorescent labeling proteins is to express the fluorescent protein in situ on the target protein by means of gene fusion technology, thereby lighting up specificity of the target protein and making it possible to perform tracking studies of the target protein in cells or tissues under a fluorescence microscope. Fluorescent protein technology has been developed for a long time and is relatively mature, but there are still a few shortcomings. For example, fluorescent proteins mature and fold slowly, and will easily aggregate; once the fluorescent protein is expressed, post-modification will be difficult; in addition, most fluorescent proteins still have a bad photostability and other shortcomings. These shortcomings limit the application of fluorescent proteins to some extent.

In fact, the molecular structure of fluorescent protein chromophores is relatively simple, and there are hardly rules to construct different types or functionalized fluorescent proteins, so sea screen is carried out by means of random mutation. In contrast, organic small molecule fluorescent dyes are rich in molecular structure, but small molecule fluorescent probes still have many defects in protein-specific labeling. Recently, the emergence of chemical tag technology has effectively solved the problem of fluorescence specific labeling using small molecule fluorescent probes. This technology fuses the target protein with a polypeptide or a protein tag having specific recognition function, and achieves small-molecule fluorescent probe-specific protein labeling by using the highly specific combination of the tag with the substrate. Thus, chemical tag technology inherits not only the advantages of gene fusion technology, but also those of organic dye probes compared to fluorescent proteins. Currently, protein tag technologies, such as SNAP-tag (K. Johnsson et. al. WO 2004031405), CLIP-tag (K. Johnsson et. al. WO 2008012296), Halo-tag (Wood, Keith V et. al. WO 2004072232), have been commercialized, wherein SNAP-tag and CLIP-tag are the most widely used chemical tags, and have got unanimous approval of the market.

Chemical tags such as SNAP-tag and CLIP-tag are capable of specifically labeling their protein of interest. However, during the practical labeling process, both free probes and labeled probes have the same problem of fluorescent emission. That is, either labeled probes or unlabeled probes emit fluorescence within the system. This non-characteristic fluorescence emission is clearly a serious defect in current chemical labeling technology. Therefore, strictly speaking, this method still cannot achieve the same specificity as fluorescent protein. The only effective way to solve this problem is washing out the unlabeled probe. Apparently, the application of this technology will be severely limited in situations where speediness is needed or the probe cannot be washed.

If a method of fluorescent-activated protein-specific labeling suitable for SNAP-tag and CLIP-tag is designed, it remains dark or emits very weak fluorescence before labeling, and the fluorescence of the dye is sharply enhanced once it is labeled onto the protein. Undoubtedly, this kind of probes will be able to achieve the same specificity as fluorescent proteins, which can avoid washing out free probes and greatly reduce the background interference of free probes, as well as widen the application of SNAP-tag and CLIP-tag technology. A method for designing a fluorescent-activated protein-specific label suitable for this technique must consider a suitable fluorescence ON/OFF mechanism. The FRET mechanism is first applied to this design, which additionally adds the ligand with a fluorescence quenching group, and the small molecule fluorescence is quenched by the quenching group in normal situations; once the ligand combines with the chemical tag, the quenching group will be released, thereby achieving fluorescence activation (T. Komatsu. et. al. J. Am. Chem. Soc. 2011, 133, 6745-6751). However, the introduction of the quenching group greatly increases the molecular volume of the probe, which greatly reduces the labeling speed and severely limits the real-time tracking and detection of proteins in cells and tissues by the probe. Furthermore, there must be a good energy level match between the fluorescent probe and the quenching group, which makes the FRET design of long wavelength fluorescent probes become very difficult, for example, the red light emitting dye. In addition, some dyes with fluorescence sensitive to polarity have also been used to design activated probes (T. K. Liu. et. al. ACS Chem. Biol. 2014, 9, 2359-2365). These probes exhibit no fluorescence or weak fluorescence when the dyes are in polar fluids, such as cell fluid. When the ligand is combined with the protein, the probe is placed in the non-polar pocket of the protein and emits stronger fluorescence. However, on the one hand, the protein surface itself has a hydration layer with great polarity, so the fluorescence enhancement of the probe is limited; on the other hand, the cell or tissue per se is a very complex system, and the polarity of each organelle varies greatly, which can all lead to a high background of the polar-sensitive probes in cell or tissue imaging. Recently, the literature (T. Y. Wang et. al. Chem Sci. 2016, 7, 301-307) reported a molecular rotor fluorescent probe with viscosity response, wherein the freedom degree of molecular rotor is reduced by the protein steric hinderance after protein ligands are covalently combined with proteins, thereby activating fluorescent of the probe. However, in this literature, the fluorescence intensity of the probe after fluorescence activation is dim, and the fluorescence quantum yield is very low. Therefore, the method reported in this literature cannot serve as qualified fluorescent protein tags for labeling, tracking, localization and quantification of target proteins.

SUMMARY OF THE INVENTION

The inventors have discovered that, by linking a ligand moiety to the electron donor of a viscosity-responsive fluorescent dye, a significant increase in fluorescent intensity is achieved after the fluorescent is activated by the combination of the ligand with a tag protein, thereby obtaining a fluorescent probe with a novel structured and viscosity response, and can be used for protein specific labeling with rapid labeling speed, high brightness of fluorescent activation, excellent bleaching resistance and wide range of application, which can be effectively used for labeling, tracking, localization and quantification of target proteins.

In view of this, the present invention provides a fluorescent probe, comprising a ligand moiety A, an optional linker moiety C, and a fluorescent dye moiety, wherein the fluorescent dye moiety is a viscosity-responsive fluorescent dye which comprises an electron donor portion D, a conjugated system B and an electron acceptor moiety, and the ligand moiety A is a group capable of identifying and labeling specificity of a target protein of a protein tag or a fusion protein tag, optionally, the ligand moiety A is a group capable of identifying and covalently labeling specificity of a target protein of a protein tag or a fusion protein tag, characterized in that the ligand moiety A is directly and covalently connected to the electron donor moiety D of the fluorescent dye moiety, or is covalently connected to the electron donor moiety D of the fluorescent dye moiety via the linker moiety C.

Optionally, said fluorescent probe has a structure represented by formula (I), (I)

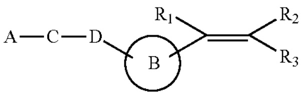

wherein:

the ligand moiety A is from an $O^6$-alkylguanine derivative or an alky 4-chloropyrimidine derivative or an alkycytosine derivative;

the linker moiety C is an optionally existing group selected from an alkylene group and a modified alkylene group; and the fluorescent dye moiety has a structure represented by formula (I-R), (I-R)

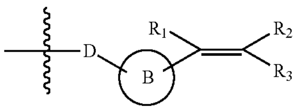

wherein:

the electron donor moiety -D- is —$NX_1$—$X_2$—, $X_1$ being selected from hydrogen, an alkyl group, or a modified alkyl group, $X_2$ being selected from an alkyl group or a modified alkyl group, and $X_1$ and $X_2$ are optionally connected to each other to form an aliphatic heterocycle with the N atom;

the conjugated system B has a structure represented by formulae (I-1-1) to (I-1-7):

(I-1-1)

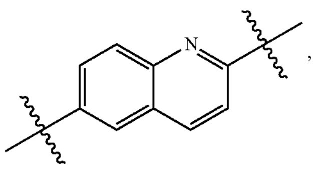

(I-1-2)

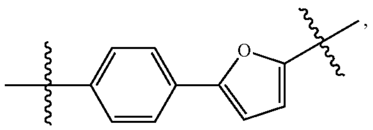

-continued (I-1-3)

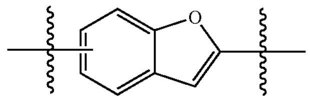

(I-1-4)

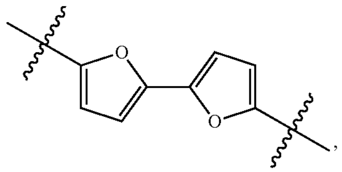

(I-1-5)

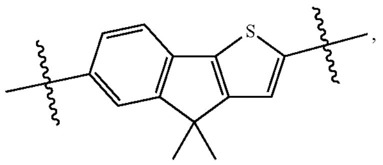

(I-1-6)

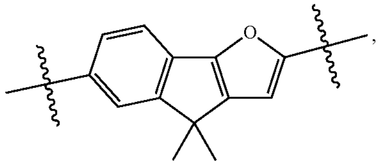

(I-1-7)

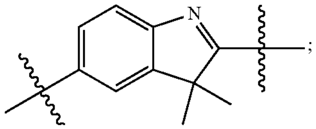

optionally, the structure represented by formulae (I-1-1) to (I-1-7) is connected with $X_1$ and $X_2$ to form an aliphatic heterocycle;

the electron accept moiety has a structure represented by formula (I-2):

(I-2)

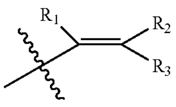

wherein:

$R_1$ is selected from hydrogen, a halogen atom, a nitro group, an alkyl group, an aryl group, a heteroaryl group, a hydrophilic group or a modified alkyl;

$R_2$ is selected from hydrogen, a cyano group, a carboxyl group, a keto group, an ester group, an amide group, a thioamino group, a thioester group, a sulfonic acid group, a sulfonate group, a sulfone group, a sulfoxide group, an aryl group, a heteroaryl group, an alkyl group or a modified alkyl group; and $R_3$ is a cyano group;

the electron acceptor moiety optionally forms a ring structure represented by the following formulae (I-2-a), (I-2-b) and (I-2-c):

(I-2-a)

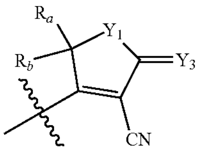

(I-2-b)

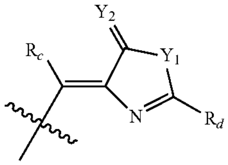

(I-2-c)

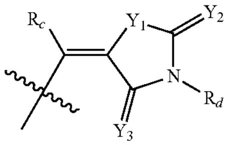

wherein:

$R_a$ and $R_b$ are independently selected from hydrogen, a hydrophilic group, an alkyl group and a modified alkyl group, and $R_a$ and $R_b$ are optionally connected to each other to form an aliphatic ring or an aliphatic heterocycle;

each $R_c$ is independently selected from hydrogen, a halogen atom, a nitro group, an alkyl group, an aryl group, a heteroaryl group, a hydrophilic group or a modified alkyl group; each $R_d$ is independently selected from hydrogen, a halogen atom, a nitro group, an alkyl group, an aryl group, a heteroaryl group, a hydrophilic group or a modified alkyl group, or a group formed by conjugate connection of a double bond with at least one of an aromatic ring and an aromatic heterocyclic ring;

each $Y_1$ is independently selected from —O—, —S—, —(S═O)—, and —($NR_i$)—, $R_i$ being selected from hydrogen, an alkyl group or a modified alkyl group;

each $Y_2$ is independently selected from ═O, ═S, ═S═O and ═$NR_i$, $R_i$ being selected from hydrogen, an alkyl group, or a modified alkyl group;

each $Y_3$ is independently selected from ═O, ═S, ═S═O and ═$NR_i$, $R_i$ being selected from hydrogen, an alkyl group or a modified alkyl group;

or, each $Y_3$ is independently ═C($R_e$)(CN);

$R_e$ being selected from a cyano group, a carboxyl group, a keto group, an ester group, an amide group, a phosphite group, a phosphate group, a sulfonic acid group, a sulfonate group, a sulfone group, a sulfoxide group, an aryl group, a heteroaryl group, an alkyl group or a modified alkyl group; when $R_2$ or $R_e$ is an aryl group or a heteroaryl group, the hydrogen atom on the ring is optionally and independently substituted by a substituent selected from a halogen atom, a cyano group, a nitro group, a hydrophilic group, an alkyl group or a modified alkyl group; optionally, the substituents are connected to each other to form a saturated or unsaturated aliphatic ring or aliphatic heterocycle;

wherein:

the "alkyl group" is a $C_1$-$C_{30}$ linear or branched alkyl; preferably a $C_1$-$C_{10}$ linear or branched alkyl; preferably a $C_1$-$C_7$ linear or branched alkyl; preferably a $C_1$-$C_5$ linear or branched alkyl; and preferably selected from methyl, ethyl, n-propyl, isopropyl, n-butyl, isobutyl, tert-butyl, sec-butyl, n-pentyl, 1-methylbutyl, 2-methylbutyl, 3-methylbutyl, isopentyl, 1-ethylpropyl, neopentyl, n-hexyl, 1-methylpentyl, 2-methylpentyl, 3-methylpentyl, isohexyl, 1,1-dimethylbutyl, 2,2-dimethylbutyl, 3,3-dimethylbutyl, 1,2-dimethylbutyl, 1,3-dimethylbutyl, 2,3-dimethylbutyl, 2-ethylbutyl, n-heptyl, 2-methylhexyl, 3-methylhexyl, 2,2-dimethylpentyl, 3,3-dimethylpentyl, 2,3-dimethylpentyl, 2,4-dimethylpentyl, 3-ethylpentyl or 2,2,3-trimethylbutyl;

the "alkylene group" is a $C_1$-$C_{30}$ linear or branched alkylene; preferably a $C_1$-$C_7$ linear or branched alkylene; and preferably a $C_1$-$C_5$ linear or branched alkylene;

the "modified alkyl group" is a group obtained by replacement of any carbon atom of an alkyl group with at least one group selected from a halogen atom, —O—, —OH, —CO—, —CS—, —$NO_2$, —CN, —S—, —$SO_2$—, —(S═O)—,

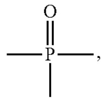

a phenyl group, a phenylene group, a primary amino group, a secondary amino group, a tertiary amino group, a quaternary ammonium group, a saturated or unsaturated monocyclic or bicyclic cycloalkylene group, a biaryl heterocyclic group, and a bridged aliphatic heterocyclic group, the modified alkyl group having 1 to 30 carbon atoms, and the carbon-carbon single bond is optionally and independently replaced by a carbon-carbon double bond or a carbon-carbon triple bond.

the "modified alkylene" is a group obtained by replacement of any carbon atom of an alkylene group with at least one group selected from a halogen atom, —O—, —OH, —CO—, —$NO_2$, —CN, —S—, —CS—, —$SO_2$—, —(S═O)—,

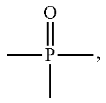

a phenyl group, a phenylene group, a primary amino group, a secondary amino group, a tertiary amino group, a quaternary ammonium group, a saturated or unsaturated monocyclic or bicyclic cycloalkylene group, a biaryl heterocyclic group, and a bridged aliphatic heterocyclic group, the modified alkylene group has 1 to 30 carbon atoms, and the carbon-carbon single bond is optionally and independently replaced by a carbon-carbon double bond or a carbon-carbon triple bond;

the replacement of the carbon atom means that the carbon atom or the carbon atom and the hydrogen atom thereon together are replaced by a corresponding group;

the "aliphatic ring" is a saturated or unsaturated 4- to 10-membered monocyclic or polycyclic aliphatic ring;

the "aliphatic heterocycle" is a saturated or unsaturated 4- to 10-membered monocyclic or polycyclic aliphatic heterocycle containing at least one heteroatom selected from N, O, S, or Si; when the aliphatic heterocycle contains an S atom, the S is in the form of —S—, —SO—, or —$SO_2$—; the aliphatic heterocycle is optionally substituted with a halogen atom, a nitro group, an alkyl group, an aryl group, a hydrophilic group, and a modified alkyl group;

the "aryl or aromatic ring" is a 5- to 10-membered monocyclic or fused bicyclic aromatic group;

the "heteroaryl or aromatic heterocyclic ring" is a 5- to 10-membered monocyclic or fused bicyclic heteroaromatic group containing at least one heteroatom selected from N, O, S or Si on the ring;

the "halogen atom" is respectively and independently selected from F, Cl, Br, I;

the "hydrophilic group" is a hydroxyl group, a sulfonic acid group, a carboxyl group, a phosphite group, a primary amino group, a secondary amino group, or a tertiary amino group;

the "monocyclic cycloalkylene group" is a 4- to 7-membered cycloalkylene group;

the "bicyclic cycloalkylene group" is a 5- to 10-membered bicyclic cycloalkylene group;

the "bridged aliphatic heterocycle" is a 5- to 20-membered bridged aliphatic heterocycle containing at least one hetero atom selected from N, O, or S on the ring;

the "keto group" is an R—(C═O)R' group;

the "ester group" is an R(C═O)OR' group;

the "amide group" is a RCONR' group;

the "thioamide group" is an R(C═S)NR' group;

the "thioester group" is an R(C═S)OR' group;

the "phosphite group" is an $RP(═O)(OH)_2$ group;

the "phosphate group" is a $ROP(═O)(OH)_2$ group;

the "sulfonic group" is an $RSO_3H$ group;

the "sulfonate group" is an $RSO_2OR'$ group;

the "sulfone group" is an $RSO_2R'$ group;

the "sulfoxide" is an RSOR' group;

the "primary amino group" is a $RNH_2$ group;

the "secondary amino group" is a RNHR' group;

the "tertiary amino group" is an RNR'R" group;

the "quaternary ammonium salt" is an $RR'R''R'''N^+$ group;

each R, R', R", R'" respectively and independently being a single bond, an alkyl group, an alkylene group, a modified alkyl group, or a modified alkylene group, and the modified alkyl group or modified alkylene group being a group obtained by replacement of any carbon atom of $C_1$-$C_{10}$ (preferably $C_1$-$C_6$) alkyl or alkylene group with a group selected from —O—, —OH, —CO—, —CS—, —(S═O)—; optionally, the modified alkyl group or modified alkylene group respectively and independently being a group containing at least one group selected from —OH, —O—, an ethylene glycol unit (—$(CH_2CH_2O)n$-), a $C_1$-$C_8$ alkyl group, a $C_1$-$C_8$ alkoxy group, a $C_1$-$C_8$ acyloxy group, a $C_1$-$C_8$ haloalkyl group, a monosaccharide group, a disaccharide group, a polysaccharide group, —O—CO—, —NH—CO—, —(—NH—CHR""—CO—)$_n$—, —$SO_2$—O—, —SO—, —$SO_2$—NH—, —S—S—, —CH═CH—, a halogen atom, a cyano group, a nitro group, an o-nitrophenyl group, a benzoylmethyl group, and a phosphate group, wherein n is 1 to 100, preferably 1 to 50, preferably 1 to 30, more preferably 1 to 10; R"" is H or a residue of a amino acid; the "phosphate group" has the definition as described above;

the "monosaccharide unit" is a saccharide unit that can no longer be simply hydrolyzed into smaller sugar molecules;

the "disaccharide unit" is a saccharide unit formed by dehydration of two monosaccharides;

the "polysaccharide unit" is a saccharide unit formed by dehydration of 10 or more monosaccharides; optionally, the $C_1$-$C_8$ alkyl group being methyl, ethyl, propyl, or isopropyl, the $C_1$-$C_8$ alkoxy group being methoxy, ethoxy, propoxy, or isopropoxy, the $C_1$-$C_8$ acyloxy being acetoxy, ethyl, propyl, or isopropyl, and the $C_1$-$C_8$ haloalkyl being trifluoromethyl, chloromethyl, or bromomethyl; optionally, the aliphatic heterocycle is selected from azetidine, pyrrolidine, piperidine, tetrahydrofuran, tetrahydropyran, morpholine, and thiomorpholine;

optionally, the heteroaryl ring is selected from

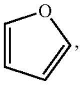, 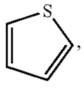, 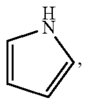, 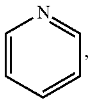, 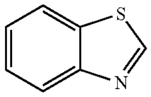,

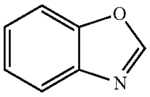, 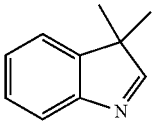.

optionally, the aryl ring is selected from

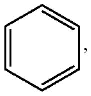, 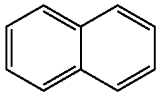.

Optionally, said fluorescent probe is characterized in that:

the protein tag is a purified product, an unpurified product, or an in situ state existing in a cell or a tissue;

optionally, the protein tag is selected from a dehalogenase;

optionally, the protein tag is a $O^6$-alkylguanine-DNA-alkyltransferase (SNAP-tag) or a mutant thereof, alkylcytimidine-transferase (CLIP-tag) or a mutant thereof.

optionally, the mutant of $0^6$-alkylguanine-DNA-alkyltransferase is selected from SNAP F33G or SNAP V164E.

optionally, the protein tag is a $O^6$-alkylguanine-DNA-alkyltransferase (SNAP-tag) or a mutant thereof;

optionally, the ligand moiety suitable for SNAP-tag is selected from $O^{6-}$ alkylguanine or alky 4-chloropyrimidine derivative;

optionally, the ligand moiety suitable for CLIP-tag is selected from an alkycytosine derivative;

optionally, the ligand moiety A- is selected from the following structures:

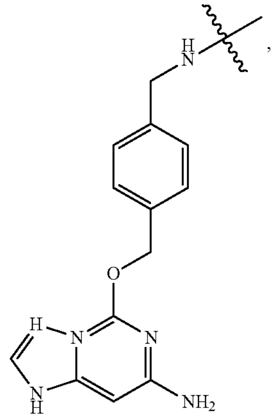

,

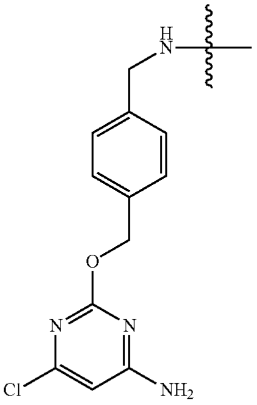

or

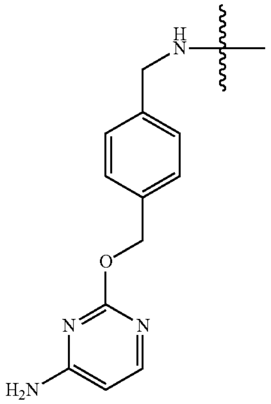

optionally, the linker moiety C is selected from a saturated linear or branched alkyl group having 1 to 30 carbon atoms, one or more carbon atoms on the alkyl chain being replaced with one or more —O— or —(C═O)—; said replacement of carbon atom with —O— or —(C═O)— means that a carbon atom or a carbon atom and the hydrogen atom thereon together are replaced with —O— or —(C═O)—;

optionally, $X_1$ is a $C_{1-30}$ linear or branched alkyl group optionally substituted with one or more groups selected from a hydroxyl group, a cyano group, a halogen atom, a carboxyl group, and a quaternary ammonium group, and $X_2$ is a $C_{1-30}$ linear or branched chain alkyl or alkylene group optionally substituted with one or more groups selected from a hydroxyl group, a cyano group, a halogen atom, a carboxyl group, and a quaternary ammonium group; or $X_1$ and $X_2$ are respectively and independently selected from $C_{2-30}$ ether chain group which contains 1 to 10 oxygen atoms and is optionally substituted with one or more groups selected from a sulfonic acid group and a carboxyl group; or $—NX_1—X_2$ forms any group selected from the following formulae (I-i-1), (I-i-2):

(-i-1)

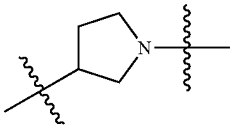

-continued (I-i-2)

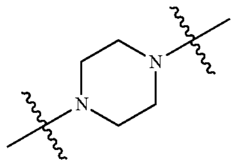

optionally, $X_1$ is a $C_{1-10}$ linear or branched alkyl group optionally substituted with one or more groups selected from a hydroxyl group, a cyano group, a halogen atom, a carboxyl group, and a quaternary ammonium group, and $X_2$ is a $C_{1-10}$ linear or branched chain alkyl or alkylene group optionally substituted with one or more groups selected from a hydroxyl group, a cyano group, a halogen atom, a carboxyl group, and a quaternary ammonium group;

optionally, said $R_2$ and $R_e$ are independently a group selected from the following structures, or a bicyclic or polycyclic fused aromatic ring or fused aromatic heterocyclic ring formed by fusion of the following structure itself or with each other; preferably is a bicyclic or tricyclic fused aromatic ring or fused aromatic heterocyclic ring;

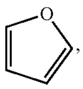, 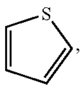, 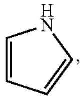, 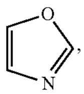, 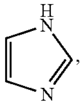, 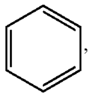,

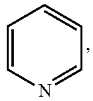, 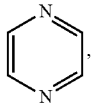, 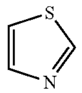;

optionally, H on CH in the above structures of $R_2$ or $R_e$ is substituted with a halogen atom, a cyano group, a nitro group, a hydrophilic group, an alkyl group, or a modified alkyl group; optionally, $R_2$ or $R_e$ is a NH-containing group selected from the above structures, and optionally, H on the NH is substituted with an alkyl group or a modified alkyl group;

alternatively, said $R_2$ is selected from hydrogen, a cyano group, a carboxyl group, a keto group, an ester group, an amide group, a thioamino group, or a thioester group, is connected to the alkenyl carbon of the formula (I-2), the formula (I-2-a), the formula (I-2-b) or the formula (I-2-c) when $R_2$ is selected from a keto group, an ester group, or an amide group, the carbonyl group in the keto group, the ester group or the amide group, and is connected to the alkenyl carbon of the formula (I-2), the formula (I-2-a), the formula (I-2 b) or the formula (I-2-c) when $R_2$ is selected from a thioamino group and a thioester group, the thiocarbonyl group in the thioamino group or the thioester group; $R_e$ is selected from a cyano group, a keto group, an ester group, and an amide group, and is connected to the alkenyl carbon of the formula (I-2-a) or the formula (I-2-c) when $R_e$ is selected from a keto group, an ester group, or an amide group, the carbonyl group in the keto group, the ester group, or the amide group;

optionally, said electron acceptor moiety is one selected from the following formulae (I-2-1) to (I-2-22):

(I-2-1)
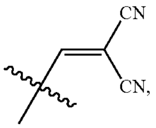
(I-2-2)
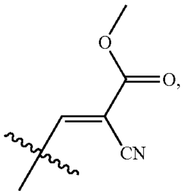
(I-2-3)
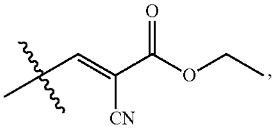
(I-2-4)
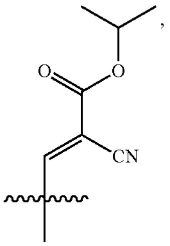
(I-2-5)
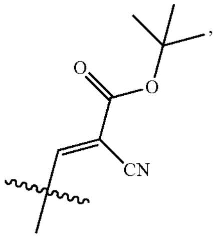
(I-2-6)
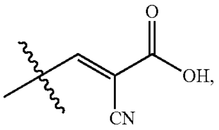
(I-2-7),
(I-2-8)
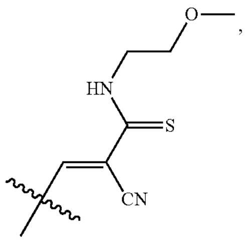
-continued
(I-2-9)
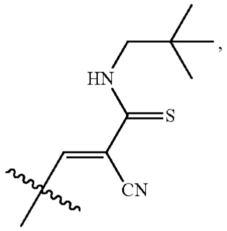
(I-2-10)
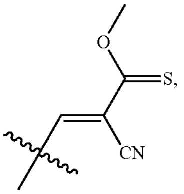
(I-2-11)
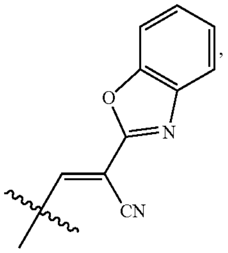
(I-2-12)
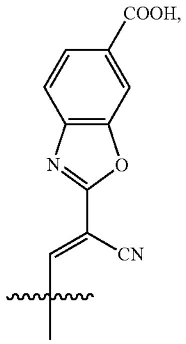
(I-2-13)
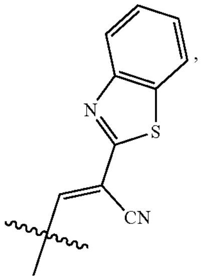

-continued
(I-2-14)
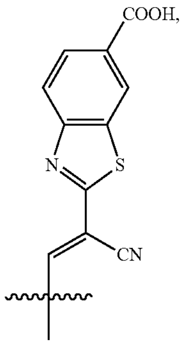
(I-2-15)
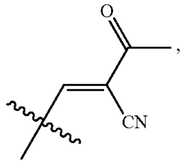
(I-2-16)
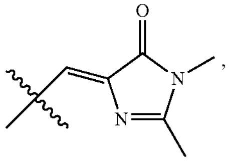
(I-2-17)
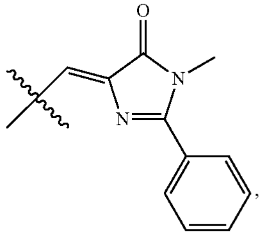
(I-2-18)
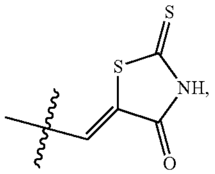
(I-2-19)
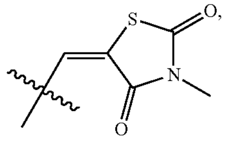
(I-2-20)
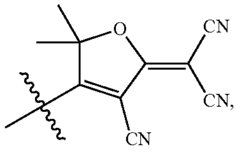
(I-2-21)
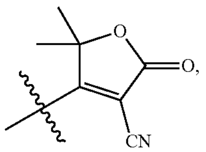
-continued
(I-2-22)
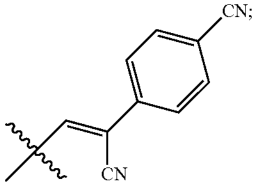
optionally, said fluorescent probe is characterized in that the fluorescent probe is selected from compounds of the following formulae or salts thereof:
probe 1
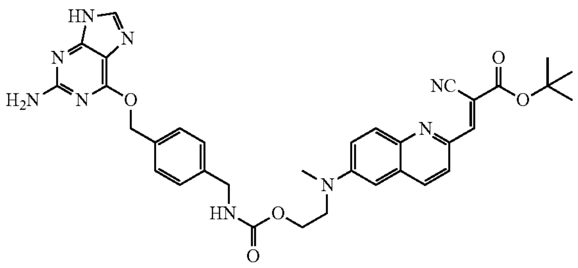
1
probe 2
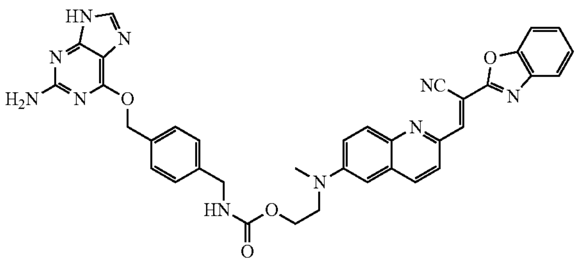
2
probe 3
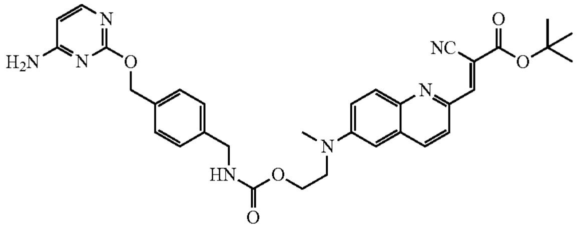
3
probe 4
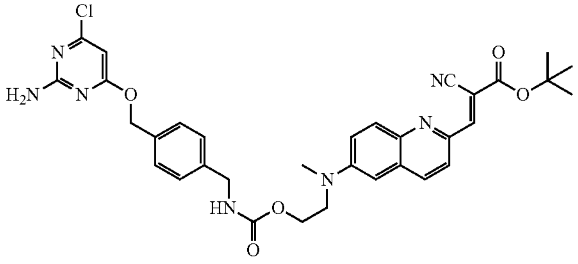

-continued
probe 5
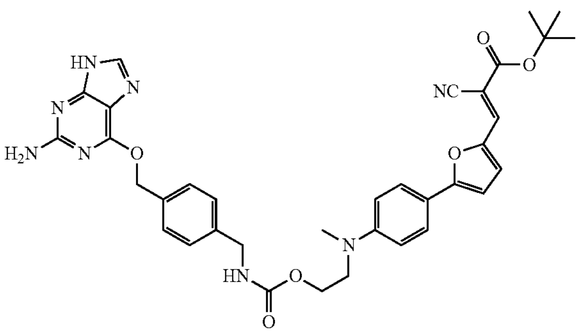
probe 6
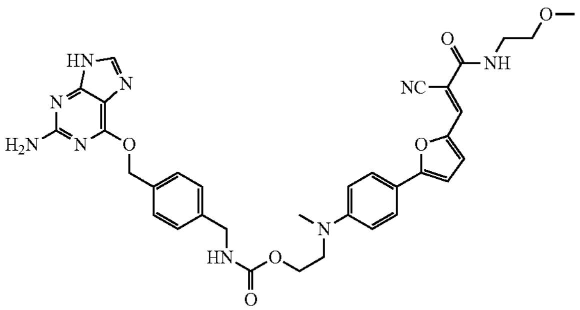
probe 7
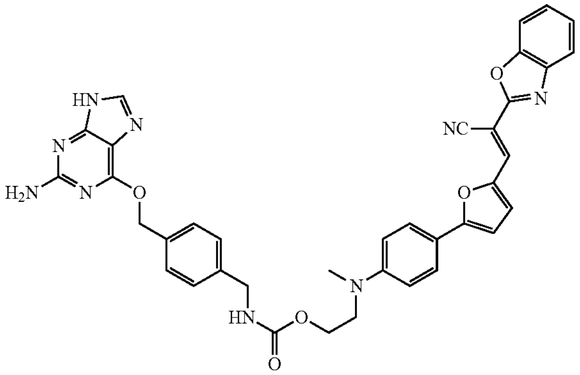
probe 8
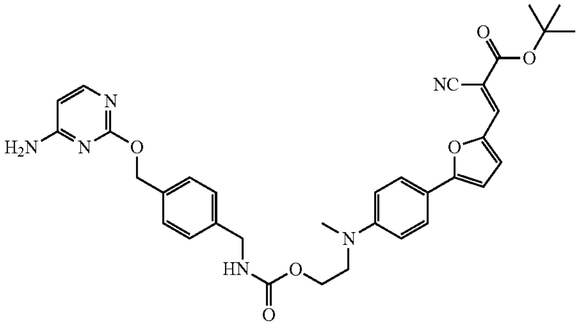
8
-continued
probe 9
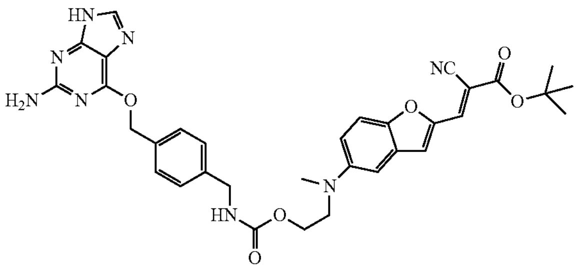
9
probe 10
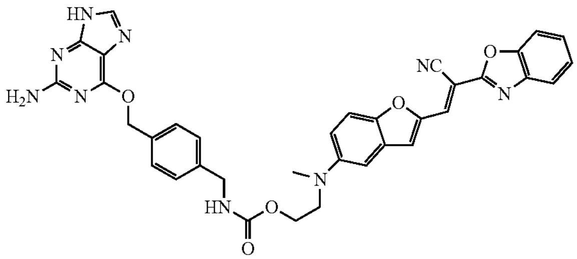
probe 11
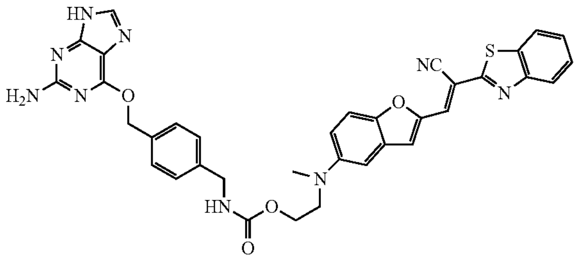
probe 12
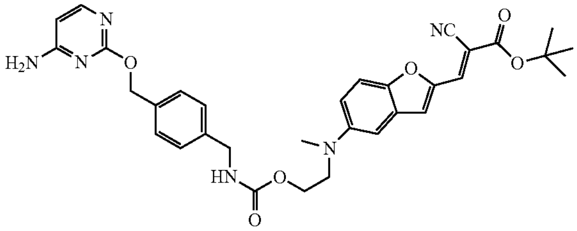
probe 13
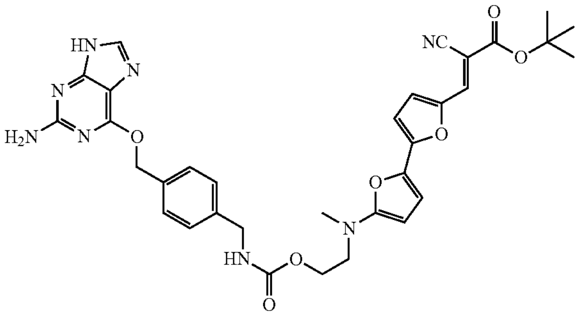
13

-continued
probe 14
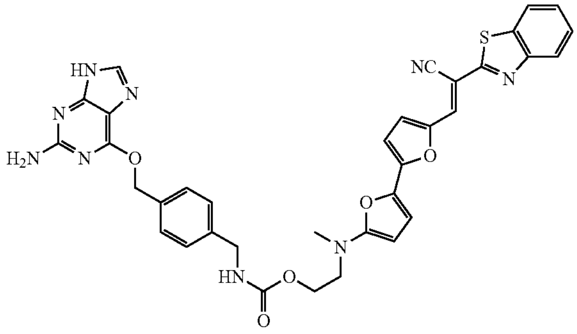
14
probe 15
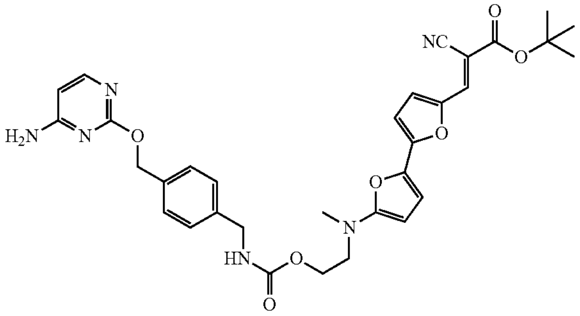
15
probe 16
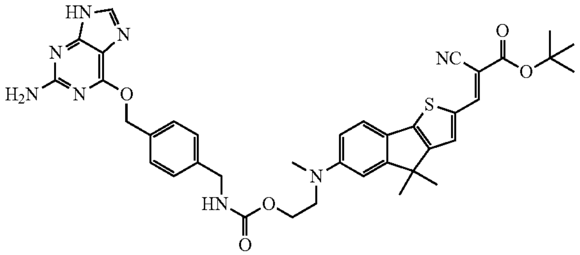
probe 17
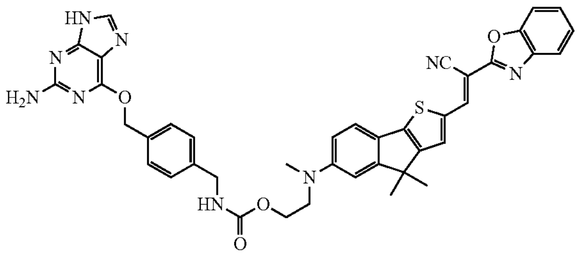
probe 18
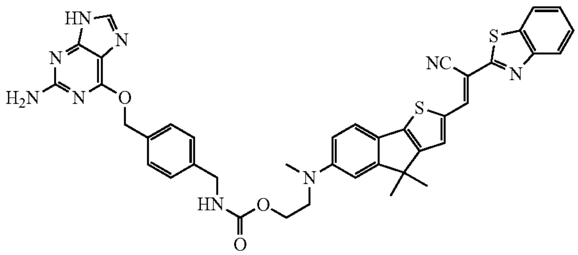
-continued
probe 19
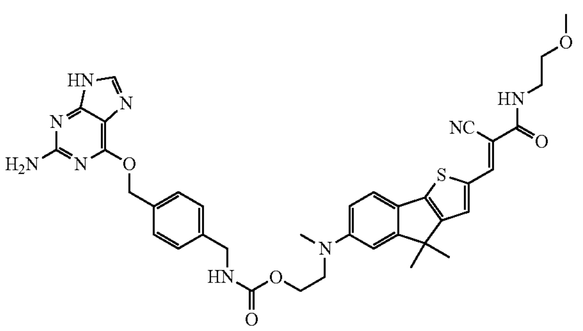
probe 20
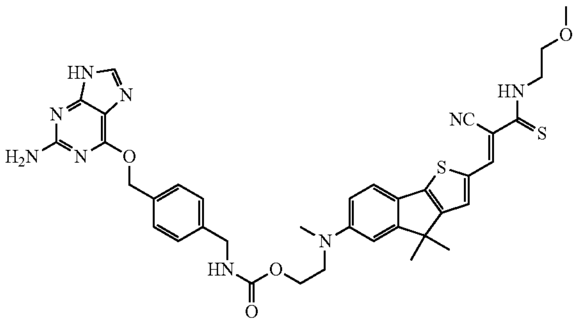
probe 21
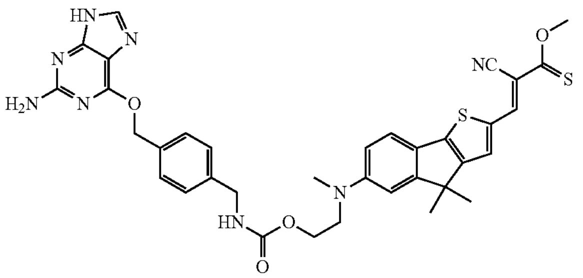
probe 22
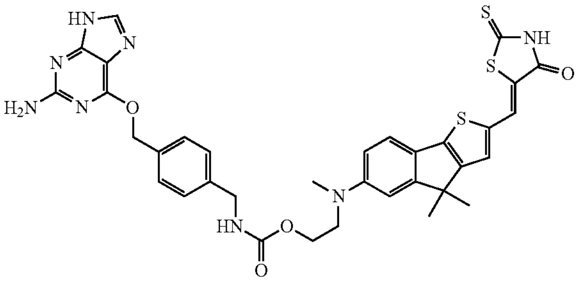
probe 23
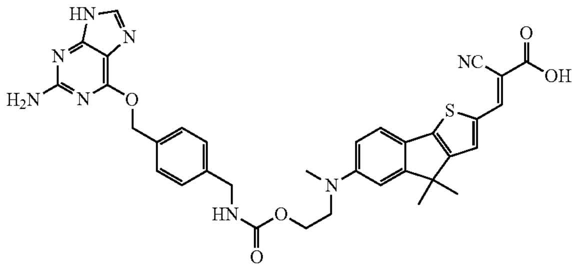

-continued probe 24

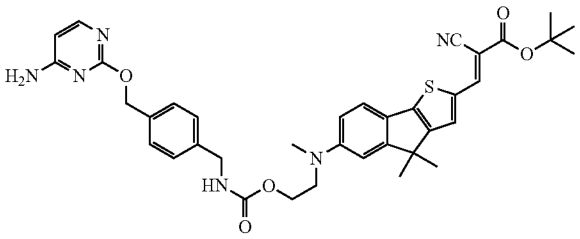

probe 25

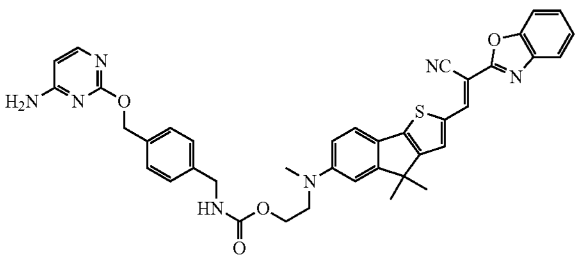

probe 26

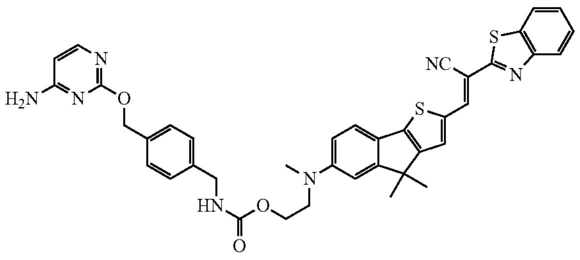

probe 27

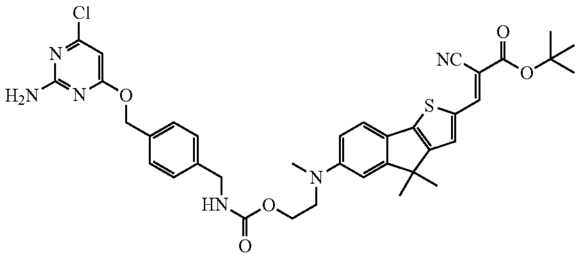

probe 28

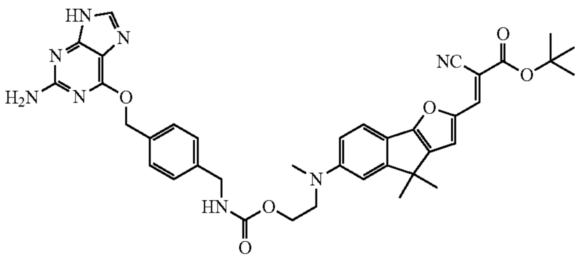

-continued probe 29

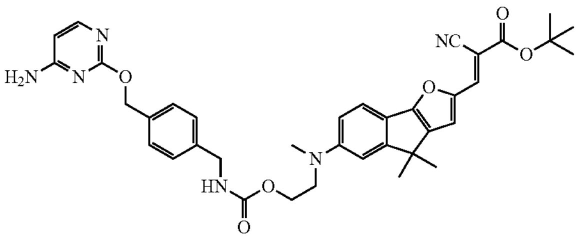

probe 30

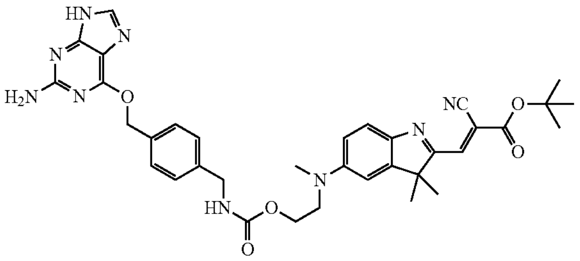

probe 31

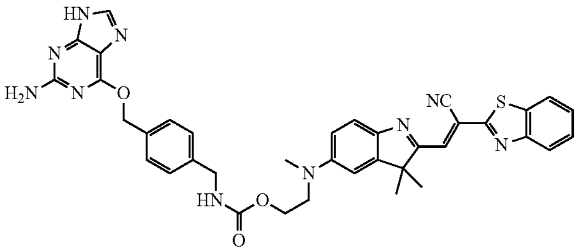

probe 32

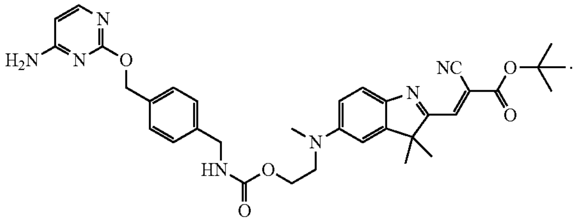

In another aspect, a method for preparing said fluorescent probe is also provided, which comprises a step of reacting the fluorescent dye represented by formula (II) with a ligand and an optional linker:

(II)

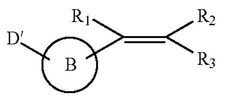

wherein, after reaction D- group is formed from D' and is bound to a linking group or a ligand. The present invention also provides a fluorescent activated protein specific labeling method, comprising steps of: contacting the said fluorescent probe with a target protein of a protein tag or a fusion protein tag; performing labeling reaction between the ligand moiety of the fluorescent probe and the protein tag to label the protein tag with the fluorescent probe; optionally, the labeling of the protein tag with the fluorescent probe is covalently labeling;

optionally, a reaction medium of said labeling reaction is selected from a pure protein solution, a cell lysate or an in situ medium in which the target protein of a protein tag or a fusion protein tag is located; optionally, the in situ medium is intracellular media, organelle media, living tissue media, blood or body fluids.

In another aspect, The present invention also provides use of the above-mentioned fluorescent probe for fluorescent labeling, quantification, detection or kinetic studies of proteins, and for imaging of cells, tissues, and living bodies.

In another aspect, the present invention also provides a probe kit comprising said fluorescent probe. Optionally, said probe kit further comprises a biocompatible medium; optionally, said biocompatible medium is at least one selected from dimethyl sulfoxide, a buffer, and physiological saline; optionally, said buffer includes phosphate buffer.

Said target protein of a protein tag or a fusion protein tag can be prepared by the existing genetic engineering techniques.

Said viscosity-responsive fluorescent dye means that the fluorescence intensity of the dye responds to the viscosity of the solution. As the viscosity of the solution increases, the fluorescence intensity is strengthened. Optionally, said viscosity-responsive fluorescent dye is an organic dye molecule which, under the same concentration and excitation wavelength, at 25° C. has a ratio of the maximum fluorescence emission intensity of the dye in glycerol to the fluorescence intensity in methanol is greater than 2, preferably greater than 5, and more preferably greater than 10. The concentration of the viscosity-responsive dye ranges from $1\times10^{-7}$ M to $1\times10^{-5}$ M.

Depending on the specific situation, the person skilled in the art can select the corresponding tags and ligands as needed.

Those skilled in the art can track and monitor the target protein of a protein tag or a fusion protein tag with equipment having corresponding configuration. The equipment used, as needed, includes devices and facilities capable of testing or displaying fluorescence, such as fluorescence spectrometers, fluorescence Microscopes, confocal fluorescence microscopes, microplate readers, flow cytometers, and in vivo imagers.

Depending on the needs, the operator can choose different types of dyes with different emission/excitation wavelengths.

According to an embodiment of one aspect, the fluorescent probe has a wide range of fluorescence emission wavelengths.

According to an embodiment of one aspect, the fluorescence intensity of the fluorescent probe increases as the environmental viscosity increases, is sensitive to viscosity and has viscosity responsiveness.

According to an embodiment of one aspect, the fluorescent probe can be used for specific labeling of a protein tag of a protein tag or a fusion protein tag. After the fluorescent probe is bound to the protein tag, fluorescence can be activated, the fluorescent probe has good fluorescent molecular switching properties, and the fluorescence activation multiple is high, and the fluorescence activation brightness is high.

According to an embodiment of one aspect, the fluorescent probe has a very fast speed of labeling the protein.

According to an embodiment of one aspect, the fluorescent probe has a good linear relationship between the fluorescence intensity and the protein tag concentration and can be used for the quantitative detection of a target protein.

According to an embodiment of one aspect, the fluorescent probe can achieve specific labeling of intracellular protein tags, and achieve fluorescence-specific lighting, and, at the same time, the probe fluorescence is not affected by the intracellular environment.

According to an embodiment of one aspect, a fluorescent probe can be used as a powerful tool for labeling cell subcellular organelle, such as labeling nucleus, mitochondria, Golgi apparatus, endoplasmic reticulum, whole cells, cytoskeleton, extracellular membrane, lysosome, intracellular membrane, or the like.

According to an embodiment of one aspect, the spectra of fluorophores of different fluorescent probes do not interfere with each other, and fluorescent probes of different colors can be used for multi-color labeling of samples, and can simultaneously perform orthogonal label imaging.

According to an embodiment of one aspect, the fluorescence of the fluorescent probe is not affected by the internal environment of the animal, and can be applied to a living animal, for example, to specifically label a SNAP-tag protein tag expressed in the liver and generate a strong fluorescent signal.

According to an embodiment of one aspect, a fluorescent probe can be used to track and monitor the degradation process of a target protein.

According to an embodiment of one aspect, the fluorescent probe monitors the assembly and degradation process of biological macromolecules in mammalian cells in real time.

According to an embodiment of one aspect, the fluorescent probe can perform rapid contrast imaging on a sample that is not suitable for washing, such as tissues, living bodies, and the like. According to an embodiment of one aspect, the fluorescent probe has excellent bleaching resistance and better photostability.

According to an embodiment of one aspect, the fluorescent probe does not exhibit any detection signal when the fluorescent probe does not label the target protein of the protein tag or the fusion protein tag, and does not interfere with the detection of the sample, and can realize rapid quantitative detection of target protein in complex samples, and can also track the dynamics of the labeling reaction process.

EMBODIMENTS

Figure 1:
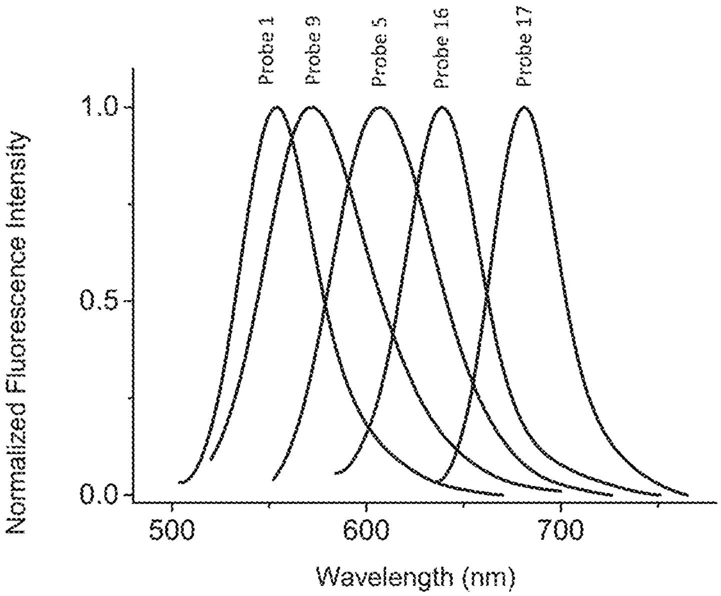
FIG. 1 is a fluorescence emission spectra of various probes that were excited by different wavelengths after combined with protein tags.
Figure 2:
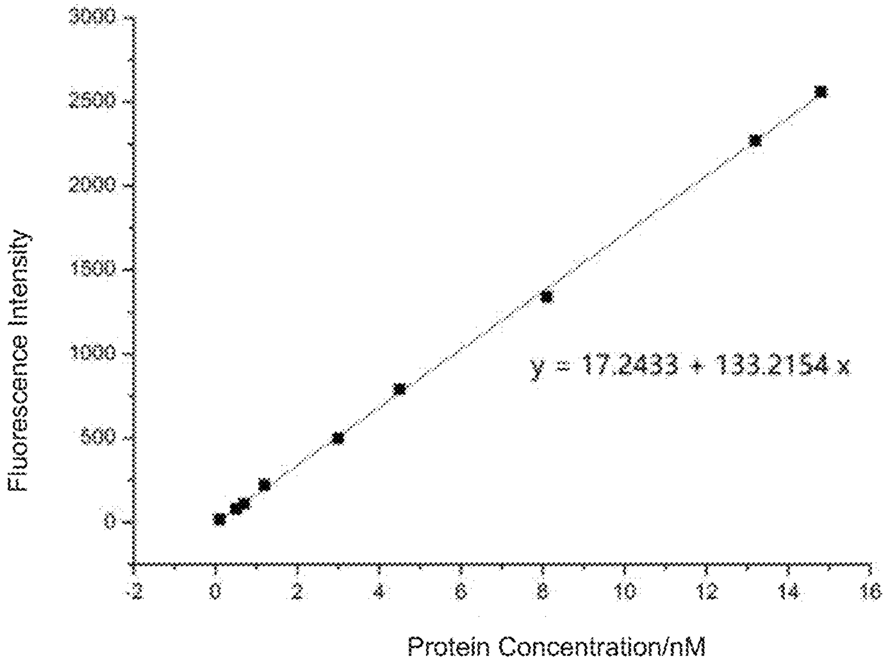
FIG. 2 is a standard curve of fluorescence intensity of probe 1 with different snap protein tag concentrations.
Figure 3:
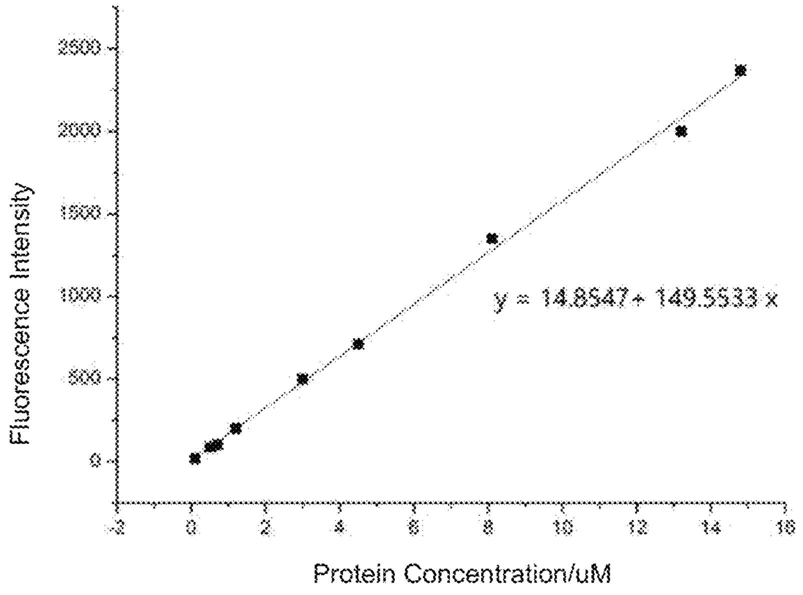
FIG. 3 is a standard curve of fluorescence intensity of probe 5 with different snap protein tag concentrations.
Figure 4:
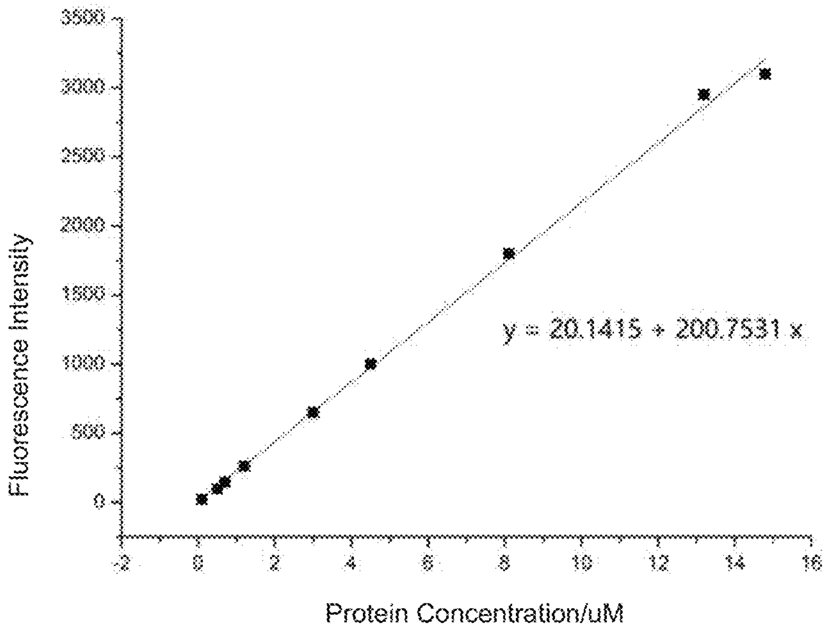
FIG. 4 is a standard curve of fluorescence intensity of probe 13 with different snap protein tag concentrations.
Figure 5:
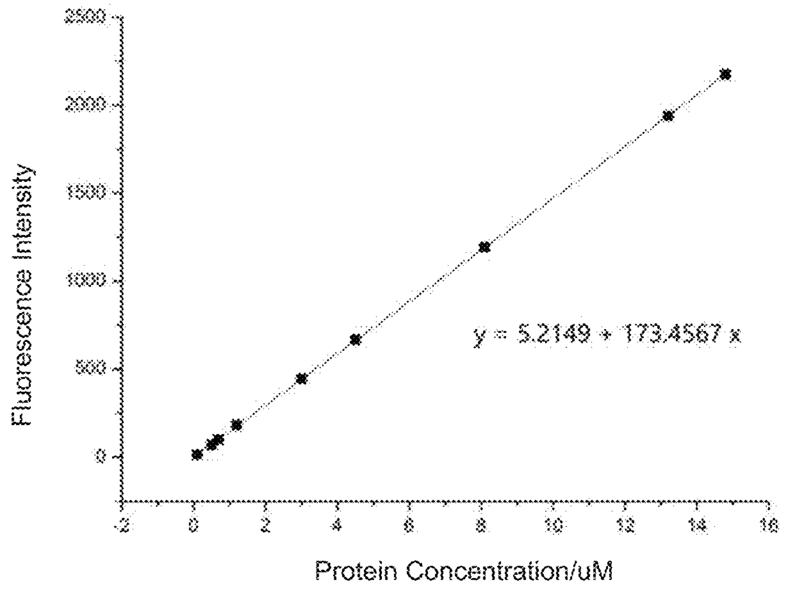
FIG. 5 is a standard curve of fluorescence intensity of probe 16 with different snap protein tag concentrations.
Figure 6:
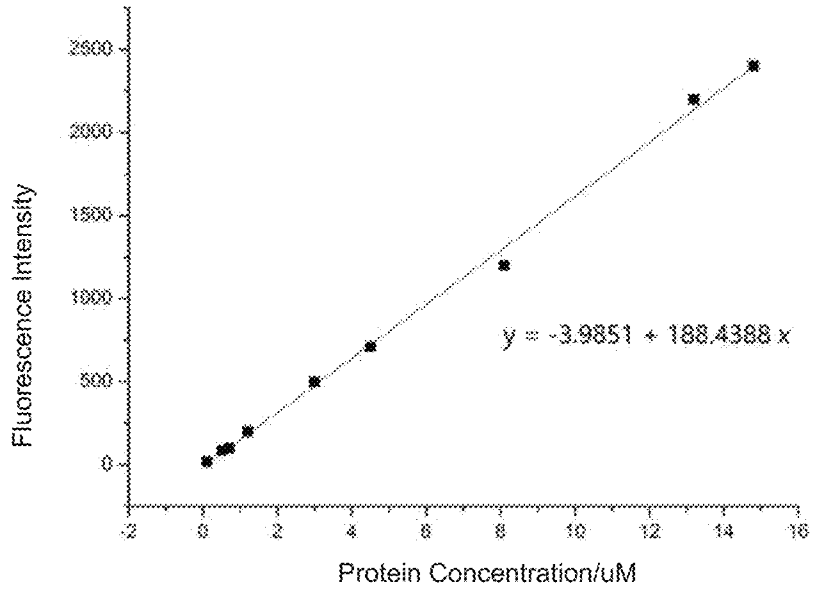
FIG. 6 is a standard curve of fluorescence intensity of probe 28 with different snap protein tag concentrations.

The embodiments of the present invention are described in detail below. It should be understood that the specific embodiments described herein are merely exemplary explanations of the present invention, and are not used for limiting the present invention.

Example 1

Utilizing molecular motor as a viscosity responsive fluorescent dye, a fluorescent activated covalent probe 1 was constructed for SNAP protein taging:

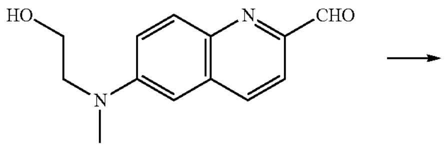

compound 1

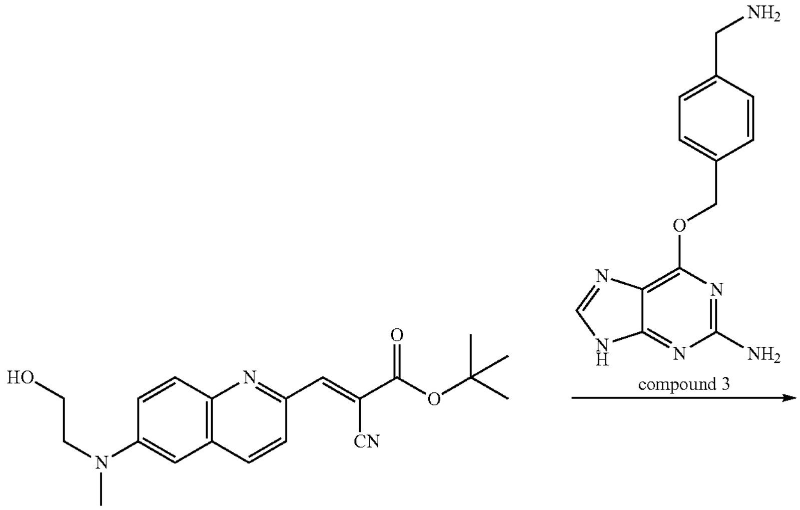

compound 3 compound 2

-continued

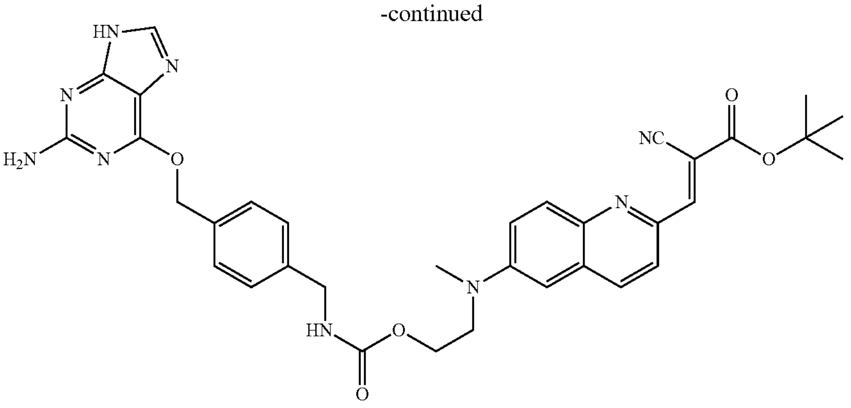

probe 1

Compound 1:

The compound was prepared according to the previously reported procedure (Hwan Myung Kim et al. ANAL CHEM. 2014, 86, 308-311). $^1$H-NMR (400 MHz, $CDCl_3$): δ=10.13 (s, 1H), 7.83-7.89 (m, 2H), 7.25-7.34 (m, 1H), 7.13 (d, 1H), 6.73 (d, 1H), 3.68 (t, 2H, J=5.6 Hz), 3.53 (t, 2H, J=5.6 Hz), 3.08 (s, 3H).

Compound 2:

Compound 1 (0.461 g, 2 mmol) and tert-Butyl Cyanoacetate (0.338 g, 2.4 mmol) were dissolved in 50 mL of anhydrous ethanol with the catalytic amount of anhydrous zinc chloride and. The mixture were heated for 5 h under an argon atmosphere. When naturally cooled to ambient temperature, part of solvent was removed under vacuum and a large amount of solid precipitates. After filtration and washed twice with cold ethanol, pure yellow compound 2 (0.41 g, 88%) was dried in vacuum to obtain with a yield of 82%. $^1$H-NMR (400 MHz, $CDCl_3$): δ=8.07 (s, 1H), 7.83-7.89 (m, 2H), 7.25-7.34 (m, 1H), 7.13 (d, 1H), 6.73 (d, 1H), 3.68 (t, 2H, J=5.6 Hz), 3.53 (t, 2H, J=5.6 Hz), 3.08 (s, 3H), 1.52 (s, 9H).

Compound 3:

The compound 3 was prepared according to the previously reported procedure (Antje Keppler et. al. Nat Biotechnology. 2002, 21, 86-89). $^1$H-NMR (400 MHz, DMSO-$d_6$): δ=7.82 (s, 1H), 7.39 (m, 4H), 6.27 (s, 2H), 5.45 (s, 2H), 3.71 (s, 2H).

Probe 1:

Compound 2 (0.353 g, 1.0 mmol) and 4-Dimethylaminopyridine (0.146 g, 1.2 mmol) were dissolved in 20 mL of anhydrous dichloromethane (DCM). 4-Nitrophenyl chloroformate (0.242 g, 1.2 mmol) was dissolved in 10 mL of DCM and added dropwise to the above solution and stirred for 1 h at room temperature. After the solvent was removed under vacuum, the residue was collected and dissolved in 10 mL of anhydrous N,N-Dimethylformamide (DMF). Compound 3 (0.324 g, 1.2 mmol) and anhydrous triethylamine (0.16 mL, 1.2 mmol) were added into above solution and stirred for 30 min at room temperature under protection of Ar. After the solvent was removed under vacuum, the residue was collected for and purified using a silica gel column to afford pure probe 1 (0.32 g) with a yield of 90%. $^1$H-NMR (400 MHz, DMSO-$d_6$): δ=12.03 (s, 1H), 8.55 (t, J=5.8 Hz, 1H), 8.12 (s, 1H), 7.83-7.89 (m, 2H), 7.79 (s, 1H), 7.44 (d, J=7.9 Hz, 2H), 7.25-7.34 (m, 3H), 7.13 (d, 1H), 6.73 (d, 1H), 6.27 (s, 2H), 5.44 (s, 2H), 4.89 (t, J=5.6 Hz, 1H), 4.37 (d, J=5.8 Hz, 2H), 3.65 (t, J=5.6 Hz, 2H), 3.48 (t, J=5.6 Hz, 2H), 3.09 (s, 3H), 1.49 (s, 9H).

Example 2

Utilizing molecular motor as a viscosity responsive fluorescent dye, a fluorescent activated covalent probe 2 was constructed for SNAP protein taging:

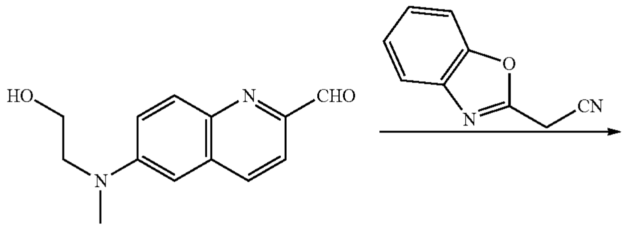

-continued

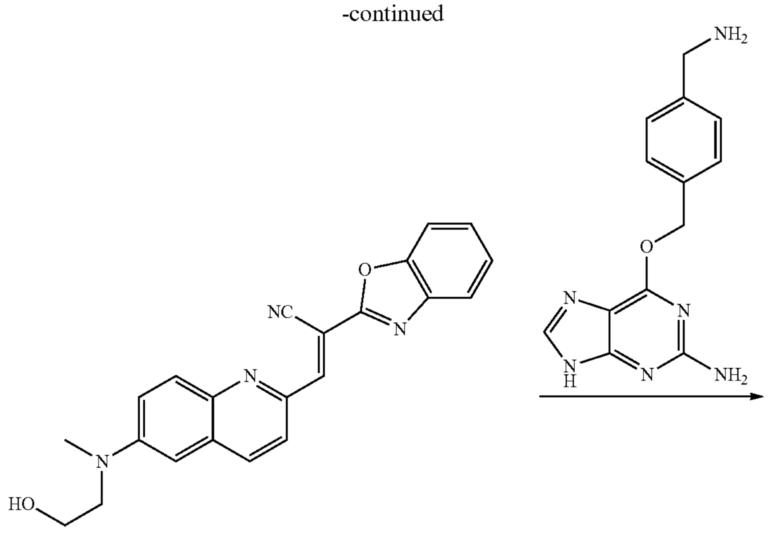

compound 4

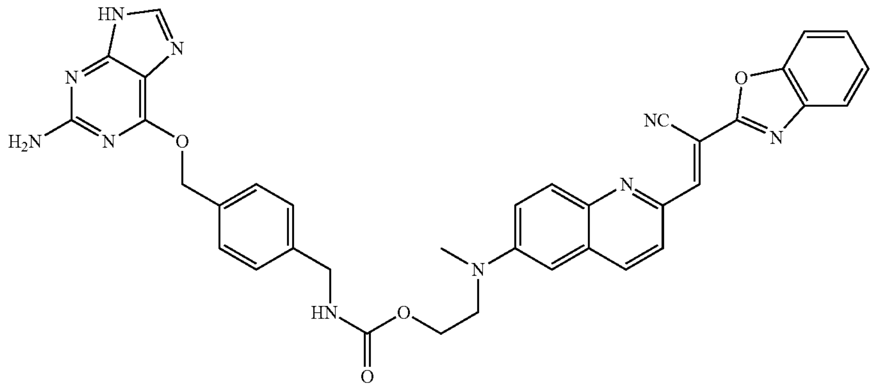

probe 2

Compound 4:

The compound 4 was synthesized according to the procedure of compound 2 with a field of 86%. $^1$H-NMR (400 MHz, $CDCl_3$): δ=8.08 (s, 1H), 7.83-7.89 (m, 2H), 7.49 (d, 1H, J=8.4 Hz), 7.36-7.42 (m, 3H), 7.25-7.34 (m, 1H), 7.13 (d, 1H), 6.73 (d, 1H), 3.61 (t, 2H, J=8.0 Hz), 3.34 (t, 2H, J=8.0 Hz), 3.11 (s, 3H).

Probe 2:

The probe 2 was synthesized according to the procedure of probe 1 with a field of 82%. $^1$H-NMR (400 MHz, DMSO-$d_6$): δ=12.31 (s, 1H), 8.52 (t, J=5.8 Hz, 1H), 8.31 (s, 1H), 8.04 (d, J=7.8 Hz, 1H), 7.89 (d, J=8.1 Hz, 1H), 7.83-7.89 (m, 2H), 7.79 (s, 1H), 7.48 (t, J=7.6 Hz, 1H), 7.44 (d, J=7.9 Hz, 2H), 7.37 (t, J=7.5 Hz, 1H), 7.25-7.34 (m, 3H), 7.13 (d, 1H), 6.73 (d, 1H), 6.27 (s, 2H), 5.76 (s, 1H), 5.44 (s, 2H), 4.88 (d, J=4.8 Hz, 2H), 4.37 (d, J=5.8 Hz, 2H), 3.65 (d, J=4.7 Hz, 2H), 3.45 (s, 2H), 3.08 (s, 3H).

Example 3

Utilizing molecular motor as a viscosity responsive fluorescent dye, a fluorescent activated covalent probe 3 was constructed for CLIP protein taging:

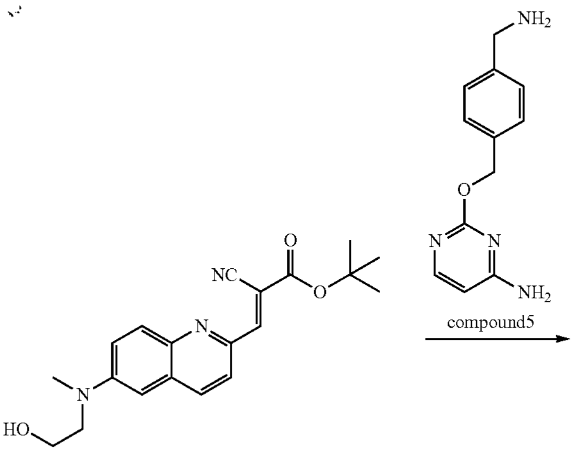

-continued

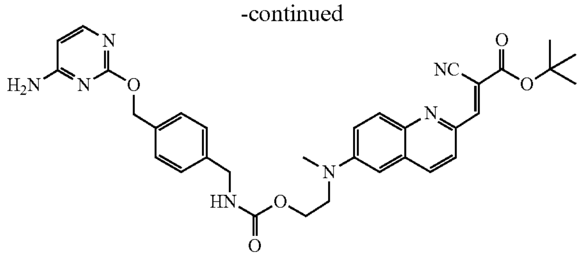

probe 3

Compound 5:

The compound 5 was synthesized according to the procedure. $^1$H-NMR (400 MHz, $CD_3OD$): δ=7.84 (d, 1H, J=6.0 Hz), 7.40 (d, 2H, J=8.0 Hz), 7.31 (d, 2H, J=8.0 Hz), 6.14 (d, 1H, J=6.0 Hz), 5.29 (s, 2H), 3.78 (s, 2H).

Probe 3:

The probe 3 was synthesized according to the procedure of probe 1 with a field of 62%. $^1$H-NMR (400 MHz, DMSO-$d_6$): δ=8.03 (s, 1H), 7.86 (d, 1H), 7.79 (d, 2H), 7.74 (t, 1H), 7.62 (d, 1H), 7.36 (d, 2H, J=6.0 Hz), 7.26 (d, 2H, J=6.0 Hz), 7.22 (d, 1H), 6.92 (d, 1H), 6.85 (s, 2H), 6.08 (d, 1H), 5.20 (s, 2H), 4.24 (t, 2H), 4.15 (d, 2H), 3.66 (t, 2H), 3.14 (s, 3H), 1.54 (s, 9H).

Example 4

Utilizing molecular motor as a viscosity responsive fluorescent dye, a fluorescent activated covalent probe 4 was constructed for SNAP protein taging:

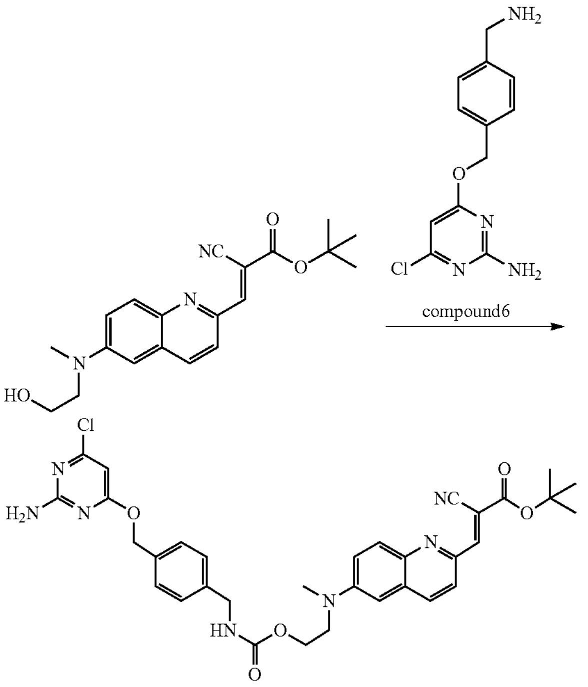

probe 4

Compound 6:

The compound was prepared according to the previously reported procedure (Srikun D K et. al. JACS 2010, 132, 4455-4465). $^1$H-NMR (400 MHz, DMSO-$d_6$): =7.33 (d, 2H, J=8.0 Hz), 7.31 (d, 2H, J=8.0 Hz), 7.10 (s, 2H), 6.10 (s, 1H), 5.25 (s, 2H), 3.68 (s, 2H).

Probe 4:

The probe 4 was synthesized according to the procedure of probe 1 with a field of 62%. $^1$H-NMR (400 MHz, DMSO-$d_6$): δ=9.99 (s, 1H), 8.01 (s, 1H), 7.83-7.89 (m, 2H), 7.72 (t, 1H), 7.39 (d, 2H), 7.25-7.34 (m, 3H), 7.13 (d, 1H), 6.73 (d, 1H), 5.26 (s, 2H), 4.36 (d, 2H), 3.55-3.59 (m, 4H), 3.08 (s, 3H), 1.50 (s, 9H).

Example 5

Utilizing molecular motor as a viscosity responsive fluorescent dye, a fluorescent activated covalent probe 5 was constructed for SNAP protein taging:

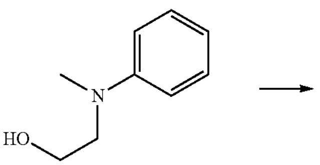

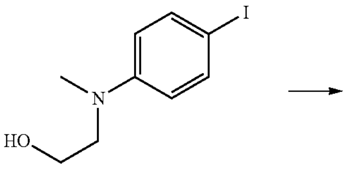

compound 7

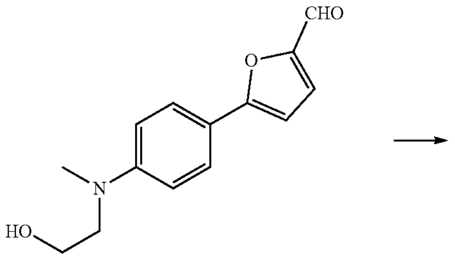

compound 8

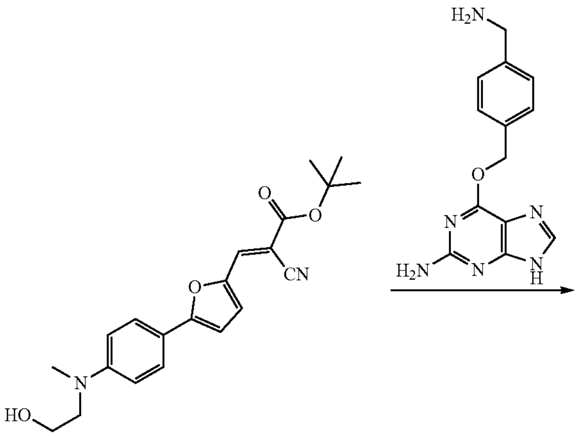

compound 9

-continued

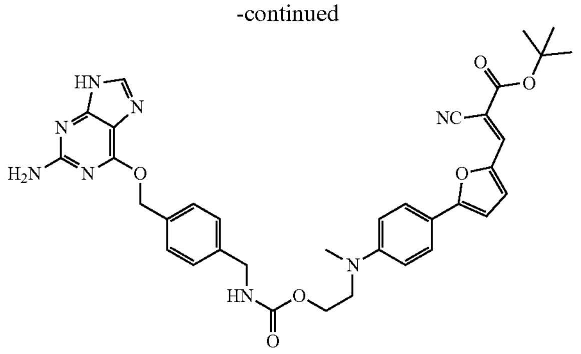

probe 5

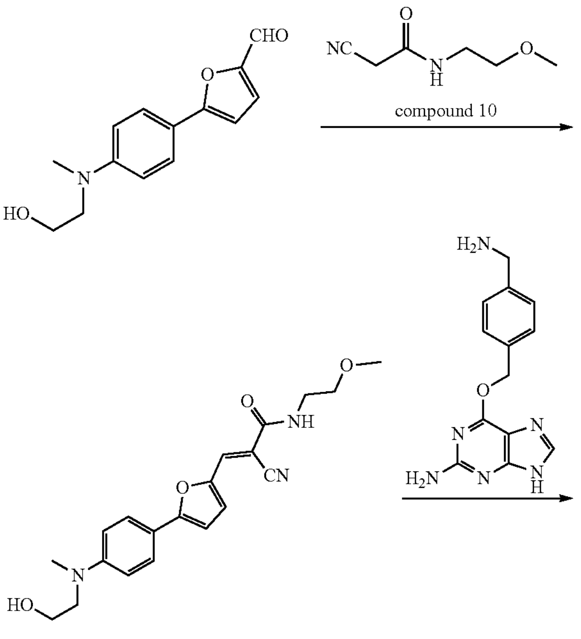

compound 11

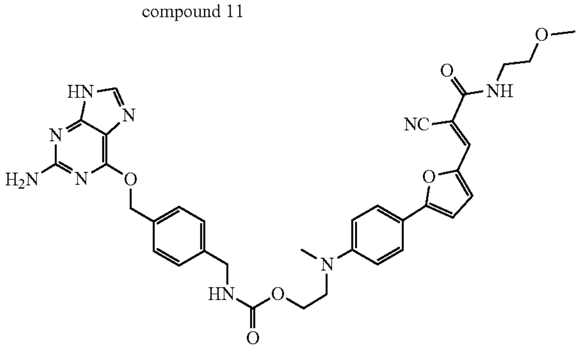

probe 6

Compound 7:

2-(N-Methylphenylamino)ethanol (1.88 g, 12.5 mmol) and $NaHCO_3$ (1.57 g, 18.7 mmol) were dissolved in the mixture of 48 mL of DCM and 36 mL of water, and cooled to 0° C. With the gent addition of $I_2$ (3.0 g, 11.8 mmol), the temperature naturally warmed to ambient temperature and stirred the solution for 30 min. The system was diluted with 300 mL of DCM and 40 mL of water to separate out the organic phase, which was washed with water, sodium thiosulfate solution and salt water, and dried with anhydrous sodium sulfate and evaporated to dryness. The residue was collected and purified using a silica gel column to afford pure compound 7 (2.46 g, 92%). $^1$H-NMR (400 MHz, $CDCl_3$): δ=7.46 (d, 1H, J=7.60 Hz), 6.56 (d, 1H, J=7.60 Hz), 3.78 (t, 2H, J=4.80 Hz), 3.44 (t, 2H, J=4.80 Hz), 2.94 (s, 3H).

Compound 8:

Compound 7 (0.554 g, 2 mmol), 5-Formylthiophene-2-boronic acid (0.374 g, 2.4 mmol) and $K_2CO_3$ solution (2 mL, 2M) were dissolved in 10 mL of methylbenzene and 10 mL of ethanol stirred at 85° C. for 5 h under an argon atmosphere. When naturally cooled to ambient temperature, 10 mL of water was added to separate out the organic phase. The aqueous phase was extracted with DCM, combined with organic phase, washed with sodium chloride, dried with anhydrous sodium sulfate, and then evaporated to dryness. The residue was collected and purified using a silica gel column to afford pure compound 8 (0.339 g) with the yield of 65%. $^1$H-NMR (400 MHz, $CDCl_3$): δ=9.81 (s, 1H), 7.68 (s, 1H), 7.55 (d, 1H, J=8.00 Hz), 7.25 (d, 2H, J=8.00 Hz), 6.78 (d, 2H, J=8.00 Hz), 3.86 (t, 2H, J=4.80 Hz), 3.56 (t, 2H, J=4.80 Hz), 3.06 (s, 3H).

Compound 9:

The compound 9 was synthesized according to the procedure of compound 2 with a field of 98%. $^1$H-NMR (400 MHz, $CDCl_3$): δ=8.01 (s, 1H), 7.68 (d, 1H), 7.55 (d, 1H), 7.25 (d, 2H, J=8.00 Hz), 6.78 (d, 2H, J=8.00 Hz), 3.86 (t, 2H, J=4.80 Hz), 3.56 (t, 2H, J=4.80 Hz), 3.06 (s, 3H), 1.50 (s, 9H).

Probe 5:

The probe 5 was synthesized according to the procedure of probe 1 with a field of 54%. $^1$H-NMR (400 MHz, $CDCl_3$): δ=12.42 (s, 1H), 10.01 (s, 1H), 8.01 (s, 1H), 7.81 (s, 1H), 7.68 (s, 1H), 7.55 (d, 1H, J=8.00 Hz), 7.40 (m, 4H), 7.25 (d, 2H, J=8.00 Hz), 6.78 (d, 2H, J=8.00 Hz), 6.29 (s, 2H), 5.46 (s, 2H), 4.40 (d, 2H, J=4.8 Hz), 3.86 (t, 2H, J=4.80 Hz), 3.56 (t, 2H, J=4.80 Hz), 3.06 (s, 3H), 1.50 (s, 9H).

Example 6

Utilizing molecular motor as a viscosity responsive fluorescent dye, a fluorescent activated covalent probe 6 was constructed for SNAP protein taging:

Compound 10:

Cyanoacetic acid (1.0 g, 10 mmol) and 2-Methoxyethylamine were added into a 25 mL round-bottom flask and stirred at room temperature under the protection of Ar. 10 mL of anhydrous ether was added into the solution and dispersed by ultrasound and filtrated. Finally, a white solid was obtained by vacuum drying. $^1$H-NMR (400 MHz, $CDCl_3$) (s, 1H), 3.48-3.52 (m, 4H), 3.38 (s, 3H).

Compound 11:

The compound 11 was synthesized according to the procedure of compound 2 with a field of 91%. $^1$H-NMR (400 MHz, DMSO-$d_6$): δ=8.31 (s, 1H), 8.22 (t, 1H), 7.82 (d, 1H, J=4.00 Hz), 7.58 (d, 2H, J=8.80 Hz), 7.50 (d, 2H, J=4.00 Hz), 6.77 (d, 2H, J=8.80 Hz), 4.74 (t, 1H), 3.57 (t, 2H, J=5.20 Hz), 3.41-3.48 (m, 4H), 3.38 (t, 2H, J=5.20 Hz), 3.27 (s, 3H), 3.01 (s, 3H).

Probe 6:

The probe 6 was synthesized according to the procedure of probe 1 with a field of 45%. $^1$H-NMR (400 MHz, DMSO-$d_6$): δ=12.42 (s, 1H), 10.01 (s, 1H), 8.31 (s, 1H), 8.22 (t, 1H), 7.82 (m, 2H), 7.58 (d, 2H, J=8.80 Hz), 7.50 (d, 2H, J=4.00 Hz), 7.40 (m, 4H), 6.77 (d, 2H, J=8.80 Hz), 6.29 (s, 2H), 5.46 (s, 2H), 4.74 (t, 1H), 4.40 (d, 2H, J=4.8 Hz), 3.57 (t, 2H, J=5.20 Hz), 3.41-3.48 (m, 4H), 3.38 (t, 2H, J=5.20 Hz), 3.27 (s, 3H), 3.01 (s, 3H).

Example 7

Utilizing molecular motor as a viscosity responsive fluorescent dye, a fluorescent activated covalent probe 7 was constructed for SNAP protein taging:

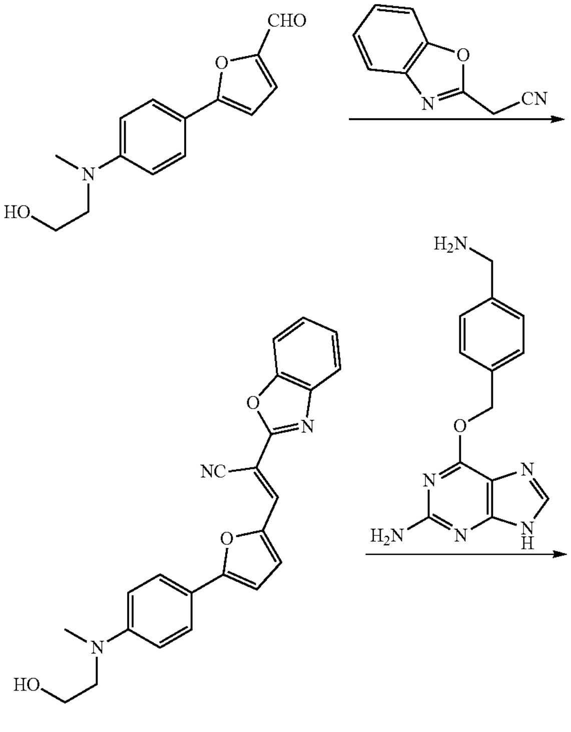

compound 12

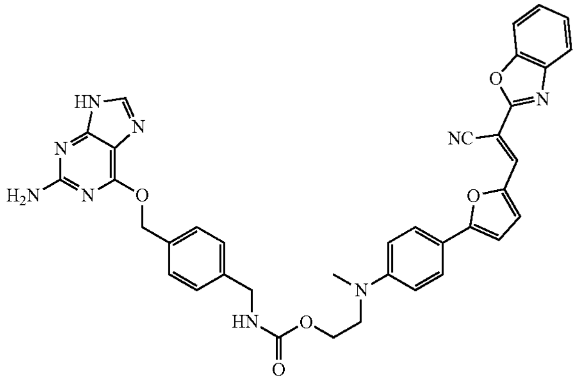

probe 7

Compound 12:

The compound 12 was synthesized according to the procedure of compound 2 with a field of 98%. $^1$H-NMR (400 MHz, $CDCl_3$): δ=7.81 (s, 1H), 7.64-7.71 (m, 3H), 7.55 (d, 1H), 7.30-7.38 (m, 2H), 7.25 (d, 2H, J=8.00 Hz), 6.78 (d, 2H, J=8.00 Hz), 4.90 (t, 1H, J=5.2 Hz), 3.66 (t, 2H, J=6.0 Hz), 3.47 (t, 2H, J=6.0 Hz), 3.10 (s, 3H).

Probe 7:

The probe 7 was synthesized according to the procedure of probe 1 with a field of 55%. $^1$H-NMR (400 MHz, DMSO-$d_6$): δ=8.55 (t, 1H, J=5.8 Hz), 8.37 (s, 1H), 7.81 (s, 1H), 7.64-7.71 (m, 3H), 7.55 (d, 1H), 7.44 (d, 2H, J=7.9 Hz), 7.30-7.38 (m, 4H), 7.25 (d, 2H, J=8.00 Hz), 6.78 (d, 2H, J=8.00 Hz), 6.27 (s, 2H), 5.44 (s, 2H), 4.90 (t, 1H, J=5.2 Hz), 4.37 (d, 2H, J=5.8 Hz), 3.66 (t, 2H, J=6.0 Hz), 3.47 (t, 2H, J=6.0 Hz), 3.10 (s, 3H).

Example 8

Utilizing molecular motor as a viscosity responsive fluorescent dye, a fluorescent activated covalent probe 8 was constructed for CLIP protein taging:

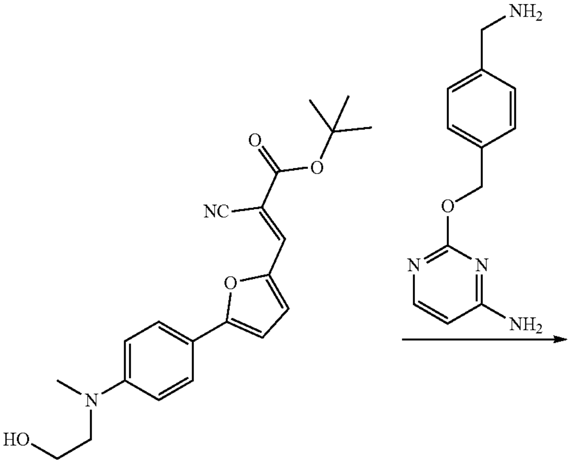

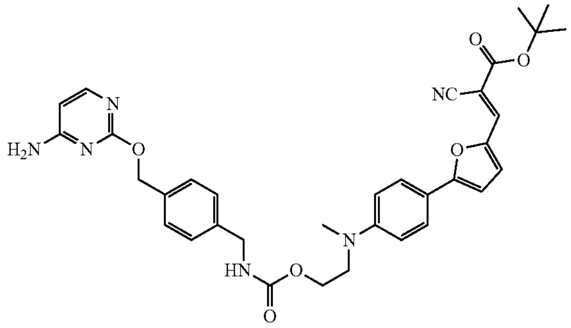

probe 8

Probe 8:

The probe 8 was synthesized according to the procedure of probe 1 with a field of 73%. $^1$H-NMR (400 MHz, DMSO-$d_6$): δ=8.03 (s, 1H), 7.86 (d, 1H), 7.74 (t, 3H), 7.68 (d, 1H), 7.55 (d, 1H), 7.36 (d, 2H, J=6.0 Hz), 7.26 (d, 2H, J=6.0 Hz), 7.25 (d, 2H, J=8.00 Hz), 6.85 (s, 2H), 6.78 (d, 2H, J=8.00 Hz), 6.08 (d, 1H), 5.20 (s, 2H), 4.24 (t, 2H), 4.15 (d, 2H), 3.66 (t, 2H), 3.14 (s, 3H), 1.54 (s, 9H).

Example 9

Utilizing molecular motor as a viscosity responsive fluorescent dye, a fluorescent activated covalent probe 9 was constructed for SNAP protein taging:

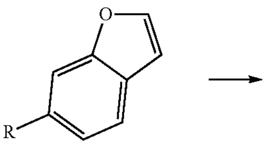

-continued

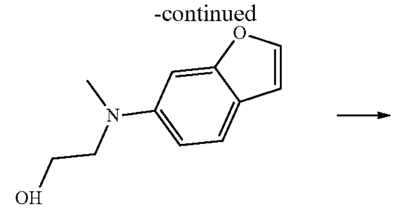

compound 13

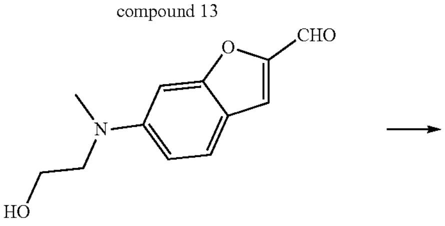

compound 14

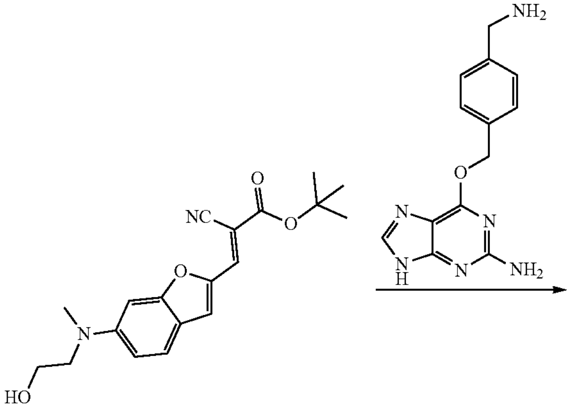

compound 15

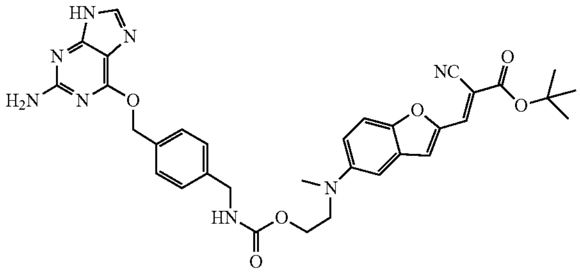

probe 9

Compound 13:

6-Bromo-1-benzofuran (0.4 g, 2 mmol) was dissolved in 15 mL of 2-(N-Methylphenylamino)ethanol with the addition of copper powder (6.4 mg, 0.01 mmol), cuprous iodide (19 mg, 0.01 mmol) and tripotassium phosphate (0.850 g, 4 mmol). The solution was stirred at 80° C. overnight under the protection of Ar. When naturally cooled to ambient temperature, the system was added into 50 mL of water, DCM (50 mL) was added for extraction three times, and the organic phase was collected and then evaporated to dryness. The residue was collected and purified using a silica gel column to afford pure yellow compound 13 (0.362 g) with the yield of 87%. $^1$H-NMR (400 MHz, $CDCl_3$): δ=8.02 (s, 1H), 7.66 (d, 1H, J=8.4 Hz), 7.44-7.48 (m, 1H), 7.41 (m, 1H), 7.29 (m, 1H), 3.60 (t, 2H, J=5.6 Hz), 3.34 (t, 3H, J=8.0 Hz), 3.10 (s, 3H).

Compound 14:

Compound 13 (0.382 g, 2 mmol) and 1 mL of triethylamine was dissolved in 50 mL of anhydrous dichloromethane (DCM). Then, acetic anhydride (0.3 mL, 3 mmol) was added dropwise to the above solution in an ice bath and stirred for 3 h at room temperature. Then the system was added into 100 mL of water. DCM (50 mL) was added for extraction twice, and the organic phase was collected, dried by anhydrous sodium sulfate and then evaporated to dryness.

The residue was dissolved in 50 mL of DCM with the addition of 5 mL of DME 2 mL of phosphorus oxychloride was added in an ice bath and stirred for 0.5 h under an Ar atmosphere. When naturally cooled to ambient temperature, the system was stirred for 5 h again. The solution was titrated to a pH of 10.0 with saturated sodium carbonate solution and then stirred overnight at room temperature. The organic phase was separated out and the aqueous phase was extracted three times with DCM. The organic phase was collected, washed with sodium chloride and dried by anhydrous sodium sulfate. After the solvent was removed under vacuum, the residue was collected and purified using a silica gel column to afford pure yellow compound 14 (0.235 g) with the yield of 56%.

$^1$H-NMR (400 MHz, $CDCl_3$): δ=9.92 (s, 1H), 7.81 (s, 1H), 7.68 (d, 1H, J=9.0 Hz), 6.92 (d, 1H, J=2.0 Hz), 6.82 (d, 1H, J=9.1, 2.3 Hz), 3.61 (t, 3H, J=8.0 Hz), 3.34 (t, 3H, J=8.0 Hz), 3.10 (s, 3H).

Compound 15:

The compound 15 was synthesized according to the procedure of compound 2 with a field of 91%. $^1$H-NMR (400 MHz, $CDCl_3$): δ=8.22 (s, 1H), 8.02 (s, 1H), 6.43 (s, 1H), 3.61 (t, 3H, J=8.0 Hz), 3.34 (t, 3H, J=8.0 Hz), 3.11 (s, 3H), 1.48 (s, 9H).

Probe 9:

The probe 9 was synthesized according to the procedure of probe 1 with a field of 66%. $^1$H-NMR (400 MHz, $CDCl_3$): δ=12.42 (s, 1H), 10.01 (s, 1H), 8.20 (s, 1H), 7.81 (s, 2H), 7.68 (d, 1H, J=9.0 Hz), 7.40 (m, 4H), 6.92 (d, 1H, J=2.0 Hz), 6.82 (d, 1H, J=9.1, 2.3 Hz), 6.29 (s, 2H), 5.46 (s, 2H), 4.40 (d, 2H, J=4.8 Hz), 3.61 (t, 3H, J=8.0 Hz), 3.34 (t, 3H, J=8.0 Hz), 3.11 (s, 3H), 1.51 (s, 9H).

Example 10

Utilizing molecular motor as a viscosity responsive fluorescent dye, a fluorescent activated covalent probe 10 was constructed for SNAP protein taging:

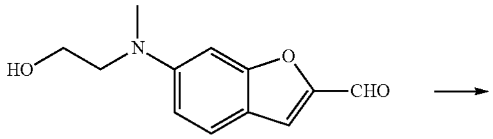

-continued

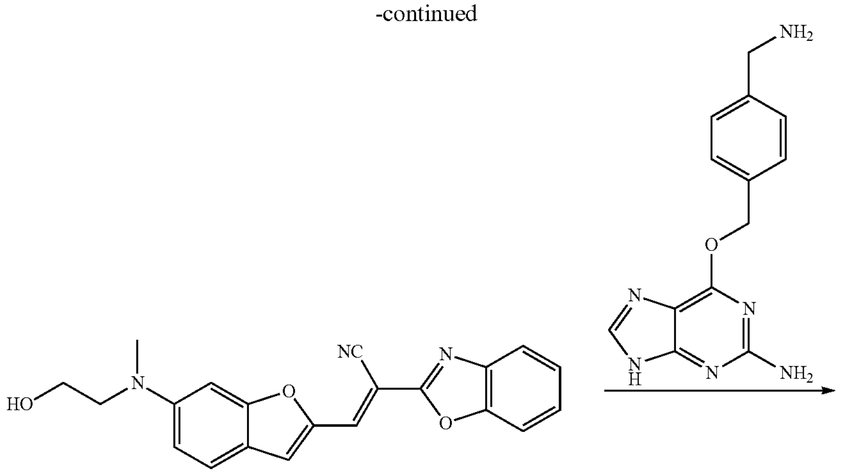

compound 16

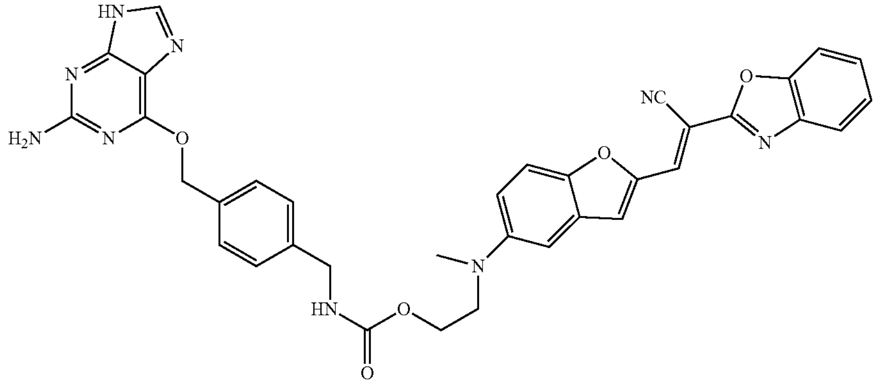

probe 10

Compound 16:

The compound 16 was synthesized according to the procedure of compound 2 with a field of 93%. $^1H$-NMR (400 MHz, DMSO-$d_6$): δ=8.45 (s, 1H), 8.09 (d, 2H, J=8.00 Hz), 8.07 (s, 1H), 7.94 (d, 2H, J=8.00 Hz), 7.51 (m, 1H), 7.41 (m, 1H), 6.45 (s, 1H), 3.61 (t, 3H, J=8.0 Hz), 3.34 (t, 3H, J=8.0 Hz), 3.21 (s, 3H).

Probe 10:

The probe 10 was synthesized according to the procedure of probe 1 with a field of 71%. $^1H$-NMR (400 MHz, DMSO-$d_6$): δ=12.42 (s, 1H), 10.01 (s, 1H), 8.45 (s, 1H), 8.09 (d, 2H, J=8.00 Hz), 8.07 (s, 1H), 7.94 (d, 2H, J=8.00 Hz), 7.81 (s, 1H), 7.51 (m, 1H), 7.41 (m, 5H), 6.45 (s, 1H), 6.29 (s, 2H), 5.46 (s, 2H), 4.40 (d, 2H, J=4.8 Hz), 3.61 (t, 3H, J=8.0 Hz), 3.34 (t, 3H, J=8.0 Hz), 3.21 (s, 3H).

Example 11

Utilizing molecular motor as a viscosity responsive fluorescent dye, a fluorescent activated covalent probe 11 was constructed for SNAP protein taging:

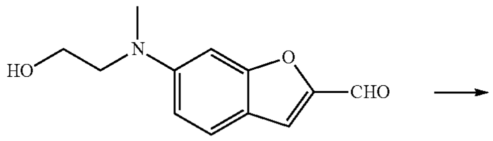

-continued

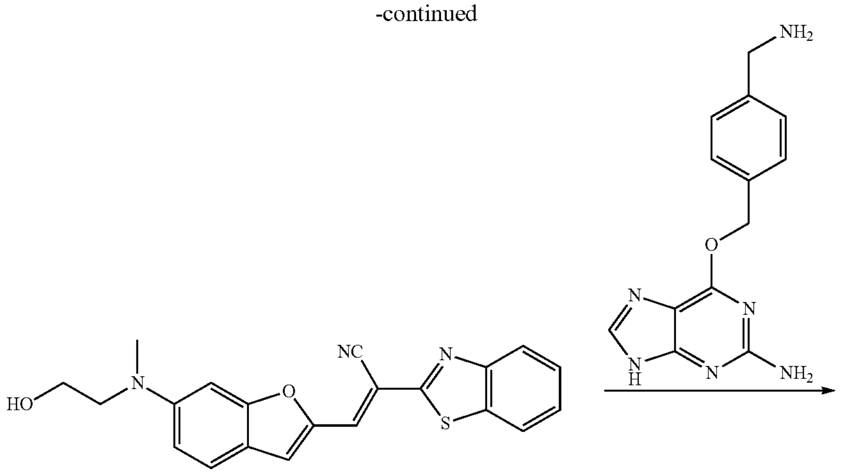

compound 17

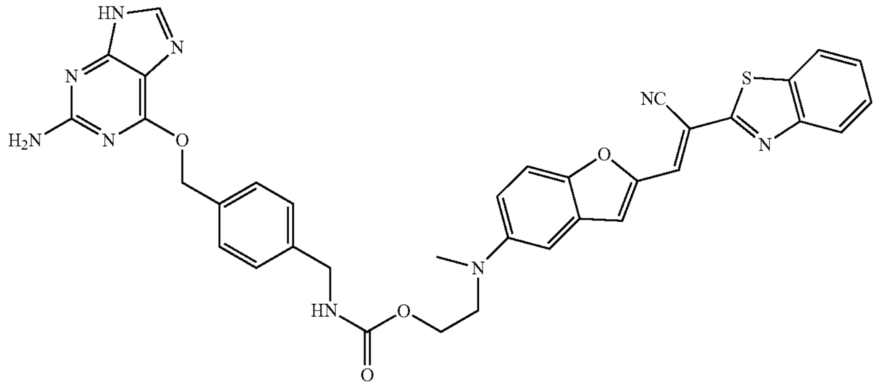

probe 11

Compound 17:

The compound 17 was synthesized according to the procedure of compound 2 with a field of 89%. $^1$H-NMR (400 MHz, DMSO-$d_6$): δ=8.09 (d, 1H, J=8.00 Hz), 7.94 (d, 1H, J=8.00 Hz), 7.81 (s, 1H), 7.68 (d, 1H, J=9.0 Hz), 7.51 (m, 1H), 7.41 (m, 1H), 6.92 (d, 1H, J=2.0 Hz), 6.82 (d, 1H, J=9.1, 2.3 Hz), 6.45 (s, 1H), 3.61 (t, 2H, J=8.0 Hz), 3.34 (t, 2H, J=8.0 Hz), 3.21 (s, 3H).

Probe 11:

The probe 11 was synthesized according to the procedure of probe 1 with a field of 66%. $^1$H-NMR (400 MHz, DMSO-$d_6$): δ=12.33 (s, 1H), 10.12 (s, 1H), 8.03 (d, 1H, J=8.00 Hz), 7.94 (d, 1H, J=8.00 Hz), 7.81 (s, 2H), 7.68 (d, 1H, J=9.0 Hz), 7.51 (m, 1H), 7.41 (m, 5H), 6.92 (d, 1H, J=2.0 Hz), 6.82 (d, 1H, J=9.1, 2.3 Hz), 6.45 (s, 1H), 6.29 (s, 2H), 5.46 (s, 2H), 4.40 (d, 2H, J=4.8 Hz), 3.62 (t, 2H, J=8.0 Hz), 3.36 (t, 2H, J=8.0 Hz), 3.21 (s, 3H).

Example 12

Utilizing molecular motor as a viscosity responsive fluorescent dye, a fluorescent activated covalent probe 12 was constructed for SNAP protein taging:

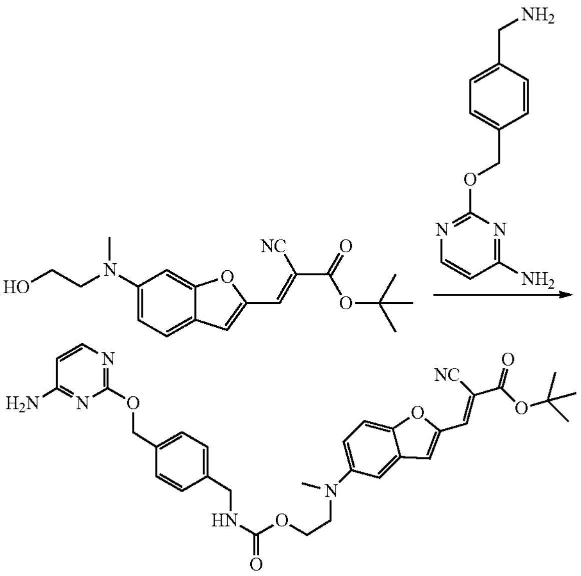

probe 12

Probe 12:

The probe 12 was synthesized according to the procedure of probe 1 with a field of 61%. $^1$H-NMR (400 MHz, $CDCl_3$):

δ=8.22 (s, 1H), 8.02 (s, 1H), 7.93 (d, 1H, J=5.6 Hz), 7.75 (s, 1H), 7.33 (d, 2H, J=8.0 Hz), 7.19 (d, 2H, J=8.0 Hz), 6.43 (s, 1H), 6.06 (d, 1H, J=5.6 Hz), 5.27 (s, 2H), 5.16 (s, 2H), 4.45 (d, 2H, J=5.6 Hz), 3.62 (t, 3H, J=8.0 Hz), 3.35 (t, 3H, J=8.0 Hz), 3.21 (s, 3H), 1.48 (s, 9H).

Example 13

Utilizing molecular motor as a viscosity responsive fluorescent dye, a fluorescent activated covalent probe 13 was constructed for SNAP protein taging:

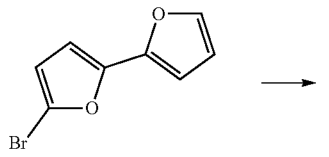

compound 18

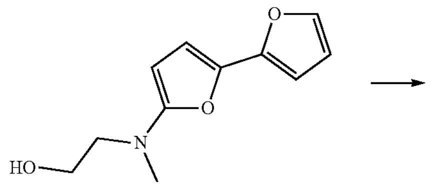

compound 19

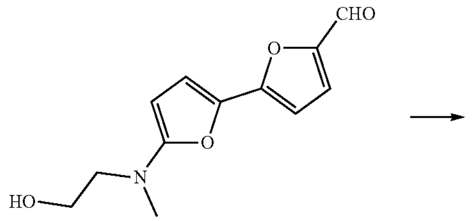

compound 20

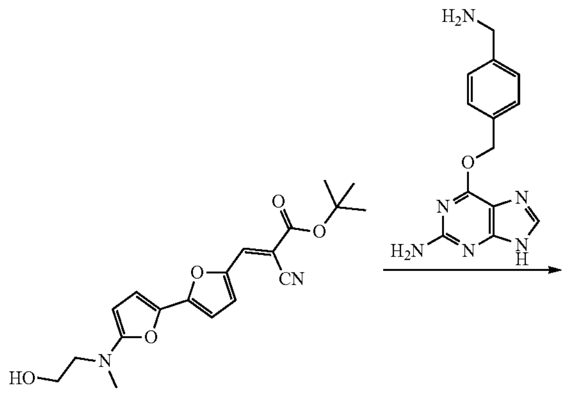

compound 21

-continued

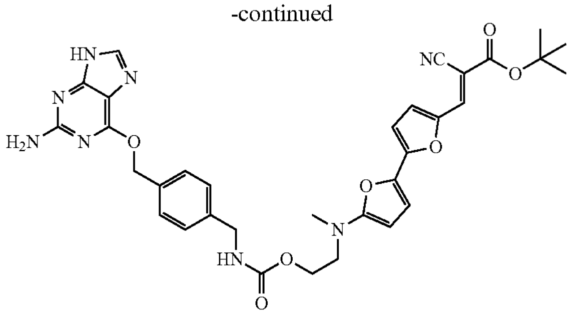

probe 13

Compound 18:

The compound 18 was prepared according to the previously reported procedure (Martinez M. et al. Org. Biomol. Chem. 2012.10.3892-3898). $^{1}$H-NMR (400 MHz, $CDCl_3$): δ=7.24 (dd, 1H, $J_1$=5.2 Hz, $J_2$=1.2 Hz), 7.13 (dd, 1H, $J_1$=3.6 Hz, $J_2$=1.2 Hz), 7.03 (dd, 1H, $J_1$=5.2 Hz, $J_2$=1.2 Hz), 6.99 (d, 1H, J=3.8 Hz), 6.93 (d, 1H, J=3.6 Hz).

Compound 19:

The compound 19 was synthesized according to the procedure of compound 13 with a field of 78%. $^{1}$H-NMR (400 MHz, $CDCl_3$): δ=7.25 (dd, 1H, $J_1$=5.2 Hz, $J_2$=1.2 Hz), 7.13 (dd, 1H, $J_1$=3.6 Hz, $J_2$=1.2 Hz), 7.03 (dd, 1H, $J_1$=5.2 Hz, $J_2$=1.2 Hz), 6.99 (d, 1H, J=3.8 Hz), 6.93 (d, 1H, J=3.6 Hz), 3.85 (t, 2H, J=4.80 Hz), 3.46 (t, 2H, J=4.80 Hz), 3.10 (s, 3H).

Compound 20:

The compound 20 was synthesized according to the procedure of compound 14 with a field of 65%. $^{1}$H-NMR (400 MHz, DMSO-$d_6$): δ=9.75 (s, 1H), 7.57 (d, 1H, J=4.00 Hz), 7.13 (d, 1H, J=4.00 Hz), 6.95 (d, 1H, J=4.00 Hz), 5.81 (d, 1H, J=4.00 Hz), 3.67 (t, 2H, J=5.60 Hz), 3.35 (t, 2H, J=5.60 Hz), 3.27 (s, 3H), 3.13 (s, 3H).

Compound 21:

The compound 21 was synthesized according to the procedure of compound 2 with a field of 98%. $^{1}$H-NMR (400 MHz, DMSO-$d_6$): δ=8.00 (s, 1H), 7.57 (d, 1H, J=4.00 Hz), 7.13 (d, 1H, J=4.00 Hz), 6.95 (d, 1H, J=4.00 Hz), 5.81 (d, 1H, J=4.00 Hz), 3.67 (t, 2H, J=5.60 Hz), 3.35 (t, 2H, J=5.60 Hz), 3.13 (s, 3H), 1.50 (s, 9H).

Probe 13:

The probe 13 was synthesized according to the procedure of probe 1 with a field of 45%. $^{1}$H-NMR (400 MHz, DMSO-$d_6$): δ=11.52 (s, 1H), 10.01 (s, 1H), 8.00 (s, 1H), 7.57 (d, 1H, J=4.00 Hz), 7.81 (s, 1H), 7.40 (m, 4H), 7.13 (d, 1H, J=4.00 Hz), 6.95 (d, 1H, J=4.00 Hz), 6.29 (s, 2H), 5.81 (d, 1H, J=4.00 Hz), 5.46 (s, 2H), 4.40 (d, 2H, J=4.8 Hz), 3.67 (t, 2H, J=5.60 Hz), 3.35 (t, 2H, J=5.60 Hz), 3.27 (s, 3H), 3.13 (s, 3H), 1.50 (s, 9H).

Example 14

Utilizing molecular motor as a viscosity responsive fluorescent dye, a fluorescent activated covalent probe 14 was constructed for SNAP protein taging:

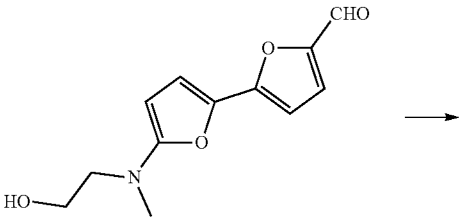

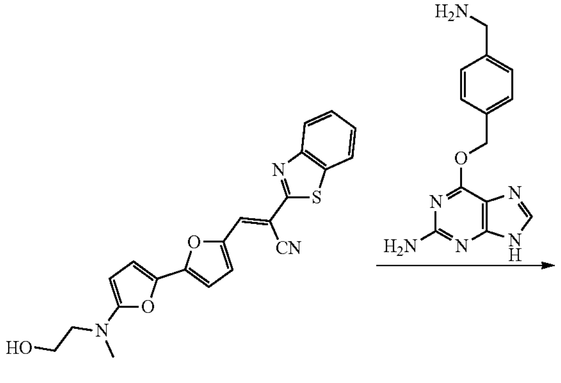

compound 22

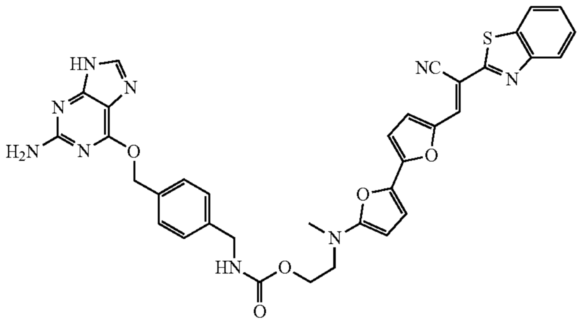

probe 14

Compound 22:

The compound 22 was synthesized according to the procedure of compound 2 with a field of 98%. $^1$H-NMR (400 MHz, DMSO-$d_6$): δ=8.04 (d, 1H, J=8.0 Hz), 7.94 (d, 1H, J=8.0 Hz), 7.89 (s, 1H), 7.57 (d, 1H, J=4.00 Hz), 7.53 (t, 1H, J=8.0 Hz), 7.45 (t, 1H, J=8.0 Hz), 7.13 (d, 1H, J=4.00 Hz), 6.95 (d, 1H, J=4.00 Hz), 5.81 (d, 1H, J=4.00 Hz), 3.67 (t, 2H, J=5.60 Hz), 3.35 (t, 2H, J=5.60 Hz), 3.13 (s, 3H).

Probe 14:

The probe 14 was synthesized according to the procedure of probe 1 with a field of 48%. $^1$H-NMR (400 MHz, DMSO-$d_6$): δ=11.82 (s, 1H), 10.21 (s, 1H), 8.04 (d, 1H, J=8.0 Hz), 7.94 (d, 1H, J=8.0 Hz), 7.89 (s, 1H), 7.81 (s, 1H), 7.57 (d, 1H, J=4.00 Hz), 7.53 (t, 1H, J=8.0 Hz), 7.45 (t, 1H, J=8.0 Hz), 7.40 (m, 4H), 7.13 (d, 1H, J=4.00 Hz), 6.95 (d, 1H, J=4.00 Hz), 6.29 (s, 2H), 5.81 (d, 1H, J=4.00 Hz), 5.46 (s, 2H), 4.40 (d, 2H, J=4.8 Hz), 3.67 (t, 2H, J=5.60 Hz), 3.35 (t, 2H, J=5.60 Hz), 3.13 (s, 3H).

Example 15

Utilizing molecular motor as a viscosity responsive fluorescent dye, a fluorescent activated covalent probe 15 was constructed for CLIP protein taging:

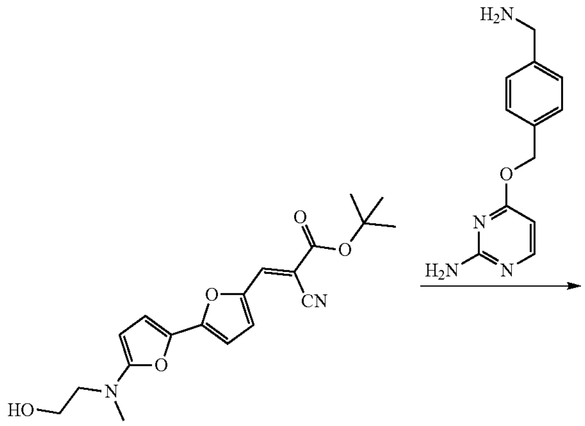

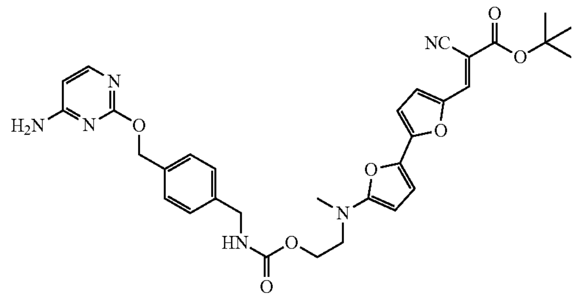

probe 15

Probe 15:

The probe 15 was synthesized according to the procedure of probe 1 with a field of 56%. $^1$H-NMR (400 MHz, DMSO-$d_6$): δ=8.00 (s, 1H), 7.93 (d, 1H, J=5.6 Hz), 7.75 (s, 1H), 7.57 (d, 1H, J=4.00 Hz), 7.33 (d, 2H, J=8.0 Hz), 7.19 (d, 2H, J=8.0 Hz), 7.13 (d, 1H, J=4.00 Hz), 6.95 (d, 1H, J=4.00 Hz), 6.06 (d, 1H, J=5.6 Hz), 5.81 (d, 1H, J=4.00 Hz), 5.27 (s, 2H), 5.16 (s, 2H), 4.45 (d, 2H, J=5.6 Hz), 3.67 (t, 2H, J=5.60 Hz), 3.35 (t, 2H, J=5.60 Hz), 3.13 (s, 3H), 1.50 (s, 9H).

Example 16

Utilizing molecular motor as a viscosity responsive fluorescent dye, a fluorescent activated covalent probe 16 was constructed for SNAP protein taging:

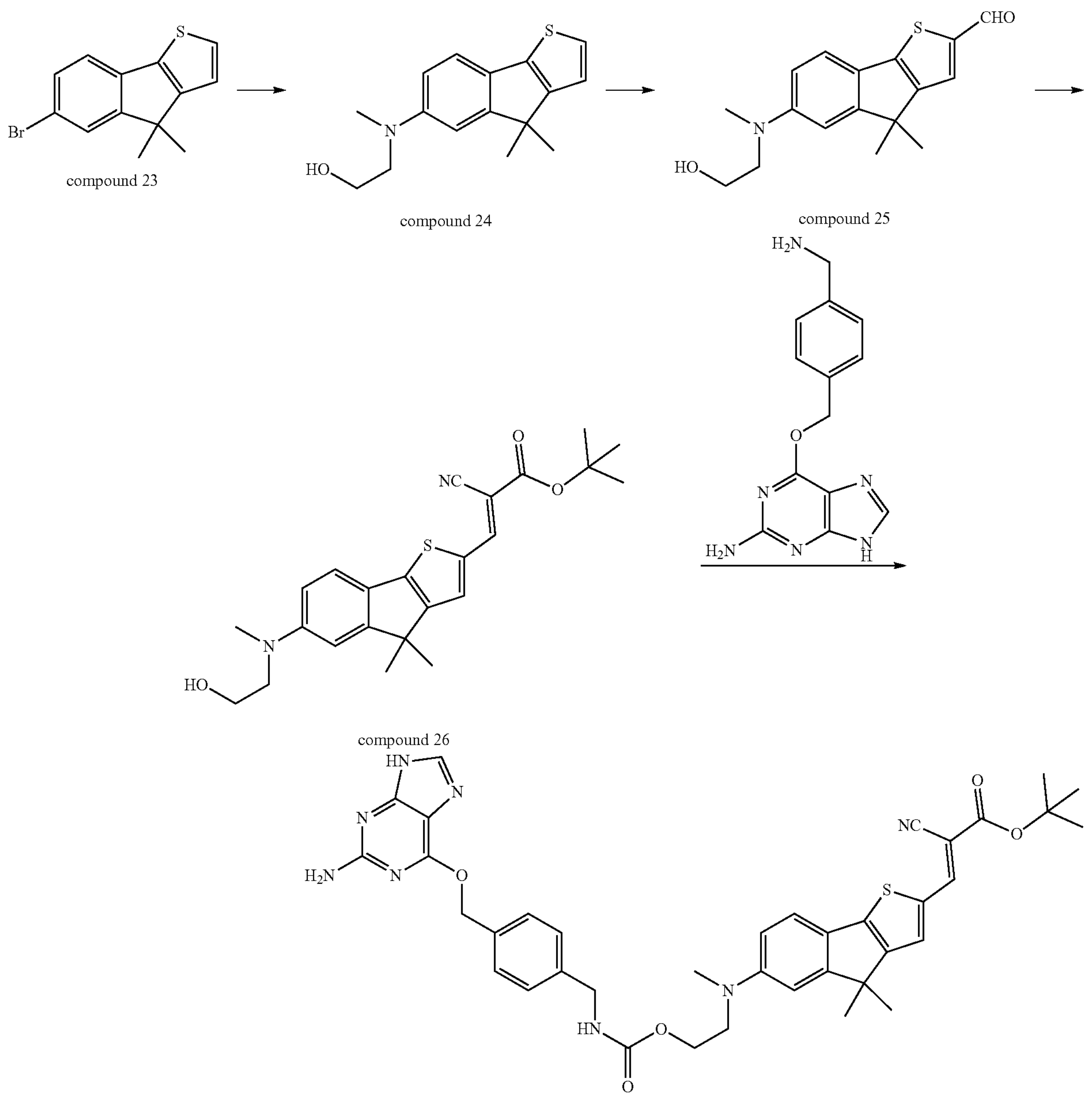

compound 23 compound 24 compound 25 compound 26 probe 16

Compound 23:

The compound 23 was prepared according to the previously reported procedure (Kimin Lim et al. J. Phys. Chem. C. 201, 115, 22640-22646). $^{1}$H-NMR (400 MHz, $CDCl_3$): δ=7.48 (s, 1H), 7.41 (d, 1H, J=8.1 Hz), 7.32 (d, 1H, J=5.1 Hz), 7.30 (d, 1H, J=7.8 Hz), 7.11 (d, 1H, J=4.5 Hz), 1.46 (s, 6H).

Compound 24:

The compound 24 was synthesized according to the procedure of compound 13 with a field of 66%. $^{1}$H-NMR (400 MHz, $CDCl_3$): δ=7.48 (s, 1H), 7.41 (d, 1H), 7.32 (d, 1H), 7.30 (d, 1H), 7.11 (d, 1H), 3.85 (t, 2H), 3.46 (t, 2H), 3.10 (s, 3H), 1.46 (s, 6H).

Compound 25:

The compound 25 was synthesized according to the procedure of compound 14 with a field of 75%. $^{1}$H-NMR (400 MHz, $CDCl_3$): δ=9.84 (s, 1H), 7.48 (s, 1H), 7.41 (d, 1H), 7.32 (d, 1H), 7.30 (s, 1H), 3.85 (t, 2H), 3.46 (t, 2H), 3.10 (s, 3H), 1.46 (s, 6H).

Compound 26:

The compound 26 was synthesized according to the procedure of compound 2 with a field of 95%. $^{1}$H-NMR (400 MHz, $CDCl_3$): δ=8.03 (s, 1H), 7.48 (s, 1H), 7.41 (d, 1H), 7.32 (d, 1H), 7.30 (s, 1H), 3.85 (t, 2H), 3.46 (t, 2H), 3.10 (s, 3H), 1.50 (s, 9H), 1.46 (s, 6H).

Probe 16:

The probe 16 was synthesized according to the procedure of probe 1 with a field of 45%. $^{1}$H-NMR (400 MHz, DMSO-$d_6$): 5=12.03 (s, 1H), 8.55 (t, 1H, J=5.8 Hz), 8.12 (s, 1H), 7.79 (s, 1H), 7.48 (s, 1H), 7.44 (d, 2H, J=7.9 Hz), 7.41 (d, 1H), 7.32 (d, 1H), 7.31 (s, 1H), 7.30 (d, 2H, J=7.9 Hz), 6.27 (s, 2H), 5.44 (s, 2H), 4.89 (t, 1H, J=5.6 Hz), 4.37 (d, 2H, J=5.8 Hz), 3.65 (t, 2H, J=5.6 Hz), 3.48 (t, 2H, J=5.6 Hz), 3.09 (s, 3H), 1.49 (s, 9H).

Example 17

Utilizing molecular motor as a viscosity responsive fluorescent dye, a fluorescent activated covalent probe 17 was constructed for SNAP protein taging:

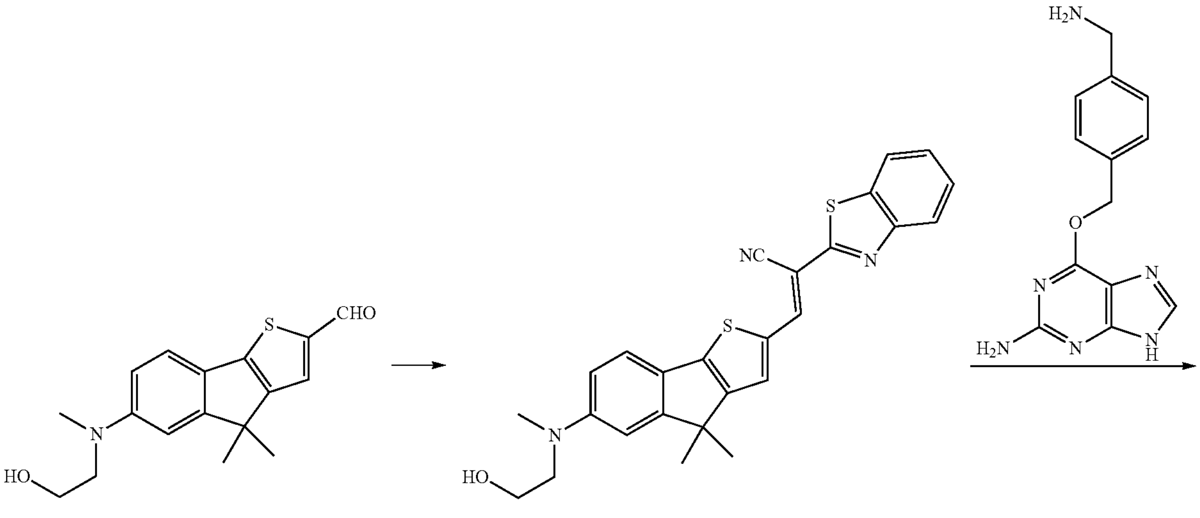

compound 27

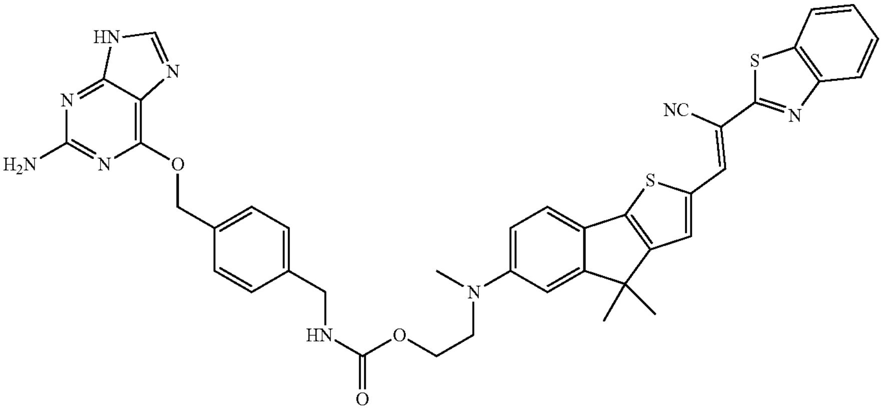

probe 17

Compound 27:

The compound 27 was synthesized according to the procedure of compound 2 with a field of 89%. $^1$H NMR (400 MHz, DMSO-$d_6$): δ=8.37 (s, 1H), 7.81 (s, 1H), 7.64-7.71 (m, 2H), 7.41 (d, 1H), 7.35-7.38 (m, 2H), 7.32 (d, 1H), 6.24 (s, 1H), 4.90 (t, 1H, J=5.2 Hz), 3.66 (t, 2H, J=6.0 Hz), 3.47 (t, 2H, J=6.0 Hz), 3.10 (s, 3H), 1.42 (s, 6H).

Probe 17:

The probe 17 was synthesized according to the procedure of probe 1 with a field of 56%. $^1$H NMR (400 MHz, DMSO-$d_6$): δ=8.55 (t, 1H, J=5.8 Hz), 8.37 (s, 1H), 7.79 (s, 1H), 7.81 (s, 1H), 7.64-7.71 (m, 2H), 7.44 (d, 2H, J=7.9 Hz), 7.41 (d, 1H), 7.35-7.38 (m, 4H), 7.32 (d, 1H), 6.27 (s, 2H), 6.24 (s, 1H), 5.44 (s, 2H), 4.90 (t, 1H, J=5.2 Hz), 4.37 (d, 2H, J=5.8 Hz), 3.66 (t, 2H, J=6.0 Hz), 3.47 (t, 2H, J=6.0 Hz), 3.10 (s, 3H), 1.42 (s, 6H).

Example 18

Utilizing molecular motor as a viscosity responsive fluorescent dye, a fluorescent activated covalent probe 18 was constructed for SNAP protein taging:

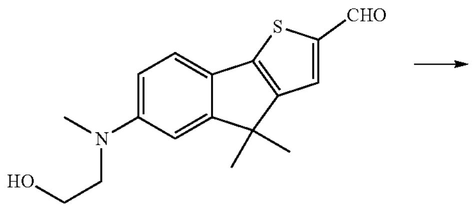

-continued

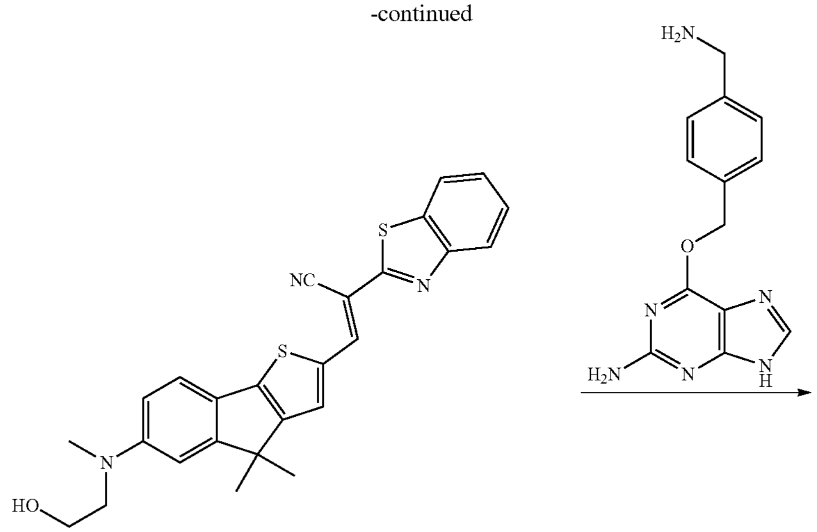

compound 28

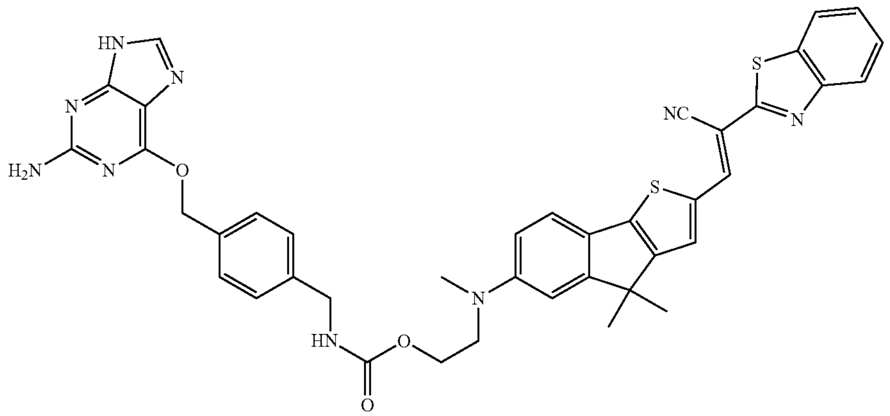

probe 18

Compound 28:

The compound 28 was synthesized according to the procedure of compound 2 with a field of 95%. $^1$H NMR (400 MHz, DMSO-$d_6$): δ=8.33 (s, 1H), 7.74 (s, 1H), 7.64-7.71 (m, 2H), 7.41 (d, 1H), 7.35-7.38 (m, 2H), 7.22 (d, 1H), 6.24 (s, 1H), 4.90 (t, 1H, J=5.2 Hz), 3.66 (t, 2H, J=6.0 Hz), 3.47 (t, 2H, J=6.0 Hz), 3.10 (s, 3H), 1.41 (s, 6H).

Probe 18:

The probe 18 was synthesized according to the procedure of probe 1 with a field of 54%. $^1$H NMR (400 MHz, DMSO-$d_6$): δ=8.45 (t, 1H, J=5.8 Hz), 8.20 (s, 1H), 7.79 (s, 1H), 7.73 (s, 1H), 7.64-7.71 (m, 2H), 7.44 (d, 2H, J=7.9 Hz), 7.41 (d, 1H), 7.35-7.38 (m, 4H), 7.32 (d, 1H), 6.27 (s, 2H), 6.24 (s, 1H), 5.44 (s, 2H), 4.90 (t, 1H, J=5.2 Hz), 4.37 (d, 2H, J=5.8 Hz), 3.66 (t, 2H, J=6.0 Hz), 3.47 (t, 2H, J=6.0 Hz), 3.10 (s, 3H), 1.41 (s, 6H).

Example 19

Utilizing molecular motor as a viscosity responsive fluorescent dye, a fluorescent activated covalent probe 19 was constructed for SNAP protein taging:

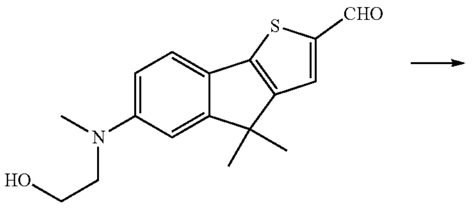

-continued

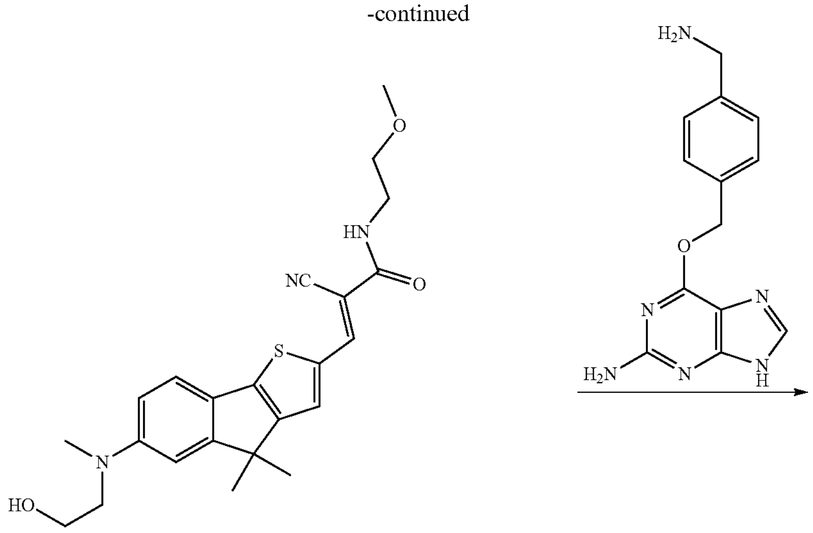

compound 29

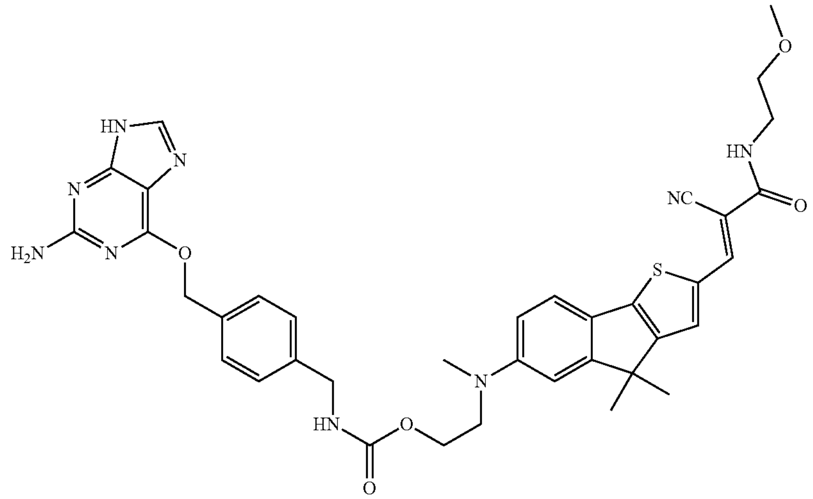

probe 19

Compound 29:

The compound 29 was synthesized according to the procedure of compound 11 with a field of 87%. $^1$H-NMR (400 MHz, $CDCl_3$): δ=8.03 (s, 1H), 7.48 (s, 1H), 7.45 (t, 1H), 7.41 (d, 1H), 7.32 (d, 1H), 7.30 (s, 1H), 3.85 (t, 2H), 3.48-3.52 (m, 4H), 3.46 (t, 2H), 3.27 (s, 3H), 3.10 (s, 3H), 1.46 (s, 6H).

Probe 19:

The probe 19 was synthesized according to the procedure of probe 1 with a field of 67%. $^1$H-NMR (400 MHz, DMSO-$d_6$): δ=8.57 (t, 1H), 8.55 (s, 1H), 8.42 (t, 1H), 8.03 (s, 1H), 7.53 (m, 2H), 7.16 (t, 2H), 7.11 (t, 2H), 6.99 (s, 2H), 6.81 (s, 1H), 6.64 (d, 1H), 5.16 (s, 2H), 4.48 (t, 2H), 4.29 (m, 2H), 4.23 (d, 2H), 3.76 (t, 2H), 3.30 (s, 3H), 3.04 (t, 2H), 2.75 (s, 3H), 1.72 (s, 6H).

Example 20

Utilizing molecular motor as a viscosity responsive fluorescent dye, a fluorescent activated covalent probe 20 was constructed for SNAP protein taging:

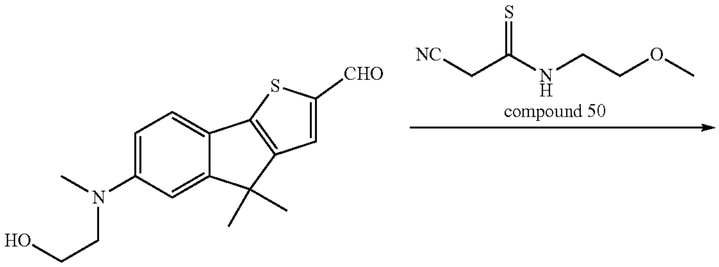

-continued

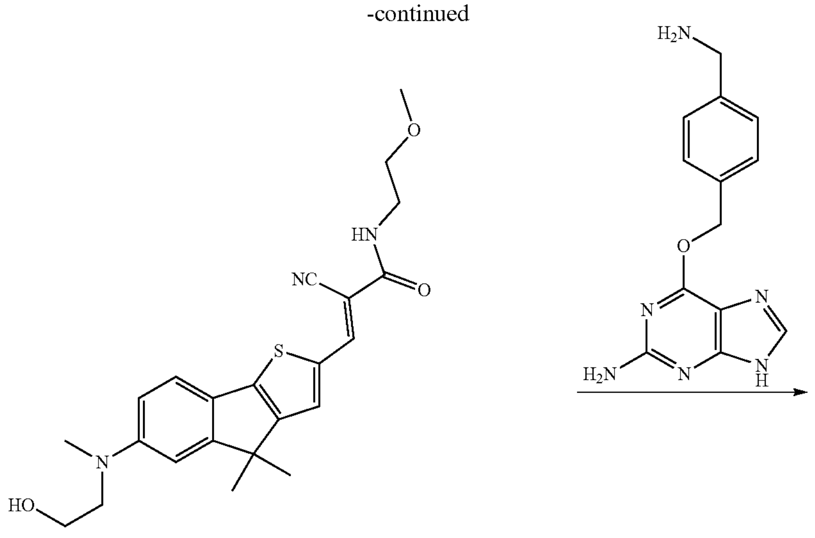

compound 31

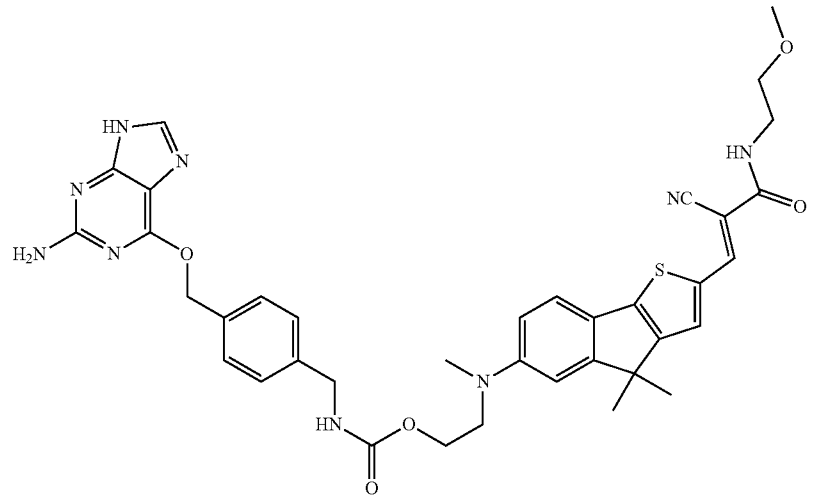

probe 20

Compound 30:

The compound 30 was prepared according to the previously reported procedure (Gamba-Sánchez. et. al. Tetrahedron Lett. 2015, 56, 4308-4311). $^1$H-NMR (400 MHz, $CDCl_3$): δ=6.52 (s, 2H), 3.48-3.52 (m, 4H), 3.38 (s, 3H).

Compound 31:

The compound 31 was synthesized according to the procedure of compound 11 with a field of 73%. $^1$H-NMR (400 MHz, $CDCl_3$): δ=8.03 (s, 1H), 7.48 (s, 1H), 7.41 (d, 1H), 7.32 (d, 1H), 7.30 (s, 1H), 7.01 (t, 1H), 3.85 (t, 2H), 3.48-3.52 (m, 4H), 3.46 (t, 2H), 3.27 (s, 3H), 3.10 (s, 3H), 1.46 (s, 6H).

Probe 20:

The probe 20 was synthesized according to the procedure of probe 1 with a field of 70%. $^1$H-NMR (400 MHz, DMSO-$d_6$): δ=8.57 (s, 1H), 8.03 (s, 1H), 7.63 (s, 1H), 7.53 (d, 2H), 7.25 (s, 1H), 7.16 (t, 2H), 7.11 (t, 2H), 6.99 (s, 2H), 6.83 (d, 1H), 6.81 (d, 1H), 6.64 (d, 1H), 5.16 (s, 2H), 4.48 (t, 2H), 4.29 (m, 2H), 4.23 (d, 2H), 3.76 (t, 2H), 3.30 (s, 3H), 2.75 (s, 1H), 2.73 (t, 2H), 2.0 (s, 1H), 1.72 (s, 6H).

Example 21

Utilizing molecular motor as a viscosity responsive fluorescent dye, a fluorescent activated covalent probe 20 was constructed for SNAP protein taging:

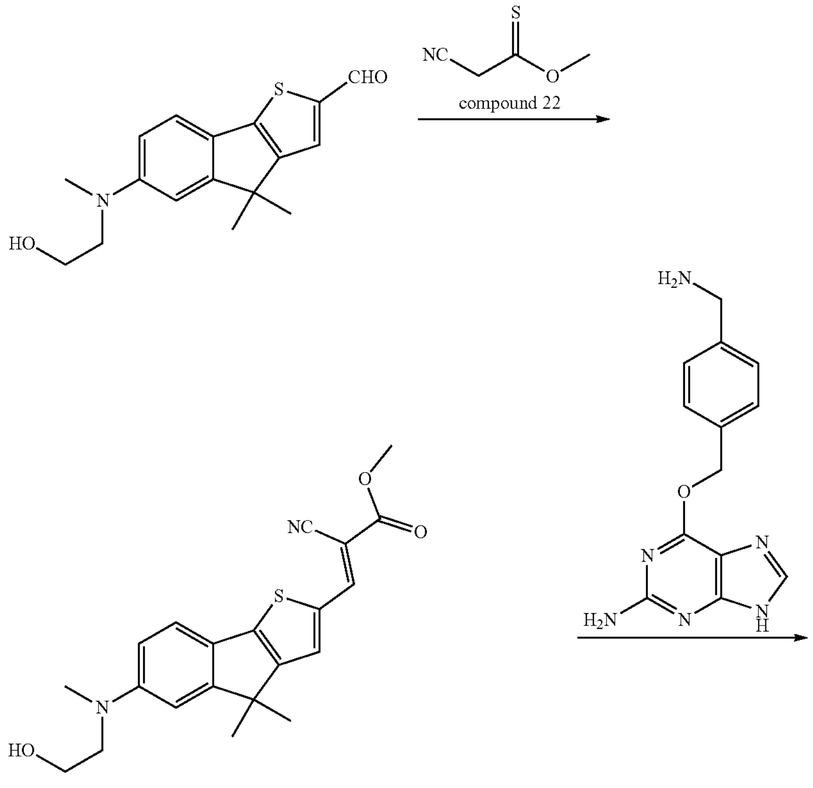

compound 33

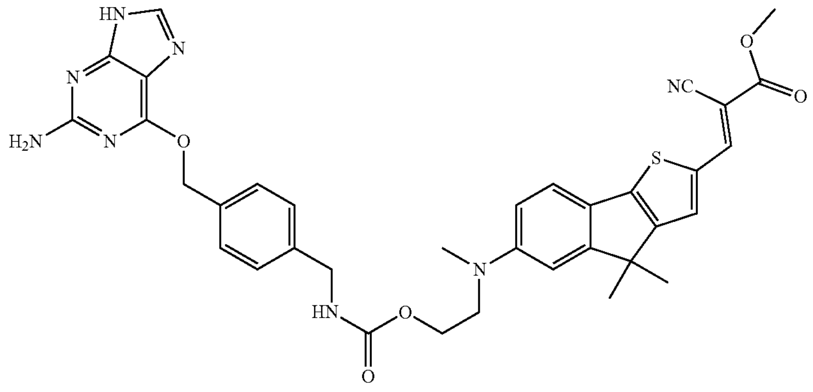

probe 21

Compound 32:

The compound 32 was prepared according to the previously reported procedure (Gamba-Sánchez. et. al. Tetrahedron Lett. 2015, 56, 4308-4311). $^1$H-NMR (400 MHz, $CDCl_3$): δ=6.56 (s, 2H), 3.42 (s, 3H).

Compound 33:

The compound 33 was synthesized according to the procedure of compound 2 with a field of 65%. $^1$H-NMR (400 MHz, $CDCl_3$): δ=8.03 (s, 1H), 7.48 (s, 1H), 7.41 (d, 1H), 7.32 (d, 1H), 7.30 (s, 1H), 3.85 (t, 2H), 3.46 (t, 2H), 3.22 (s, 3H), 3.10 (s, 3H), 1.46 (s, 6H).

Probe 21:

The probe 21 was synthesized according to the procedure of probe 1 with a field of 33%. $^1$H-NMR (400 MHz, DMSO-$d_6$): δ=12.03 (s, 1H), 8.55 (t, 1H, J=5.8 Hz), 8.12 (s, 1H), 7.79 (s, 1H), 7.48 (s, 1H), 7.44 (d, 2H, J=7.9 Hz), 7.41 (d, 1H), 7.32 (d, 1H), 7.31 (s, 1H), 7.30 (d, 2H, J=7.9 Hz), 6.27 (s, 2H), 5.44 (s, 2H), 4.89 (t, 1H, J=5.6 Hz), 4.37 (d, 2H, J=5.8 Hz), 3.65 (t, 2H, J=5.6 Hz), 3.48 (t, 2H, J=5.6 Hz), 3.21 (s, 3H), 3.09 (s, 3H).

Example 22

Utilizing molecular motor as a viscosity responsive fluorescent dye, a fluorescent activated covalent probe 22 was constructed for SNAP protein taging:

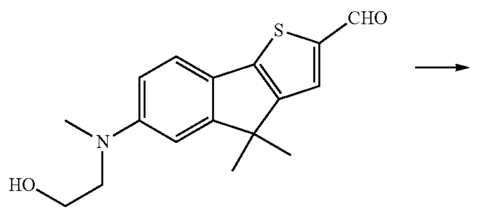

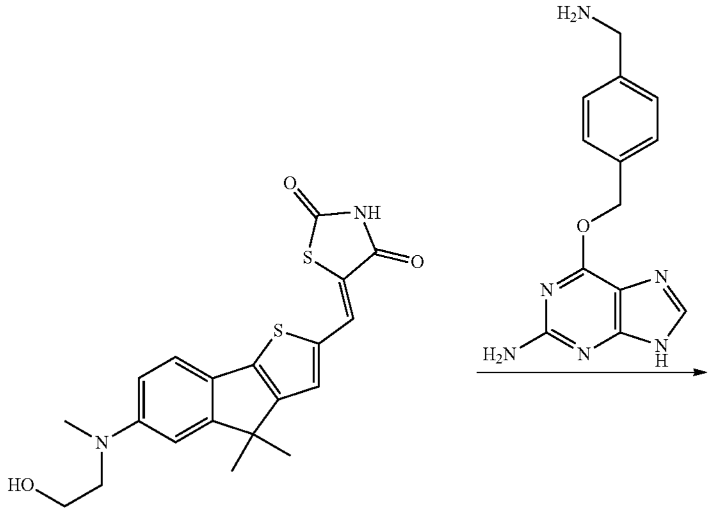

compound 34

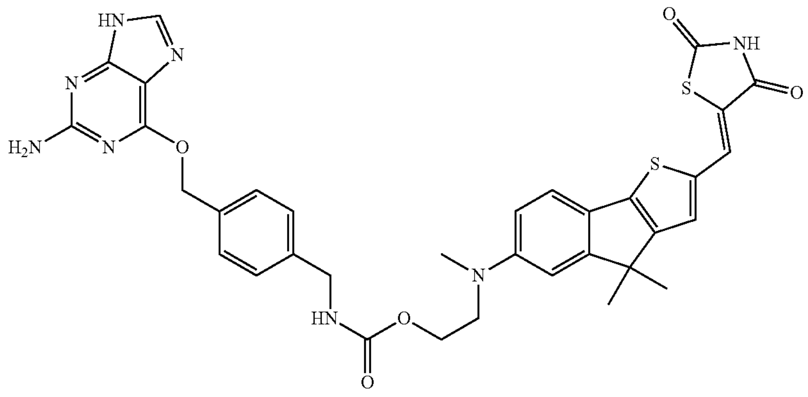

probe 22

Compound 34:

The compound 34 was synthesized according to the procedure of compound 2 with a field of 67%. $^1$H-NMR (400 MHz, $CDCl_3$): δ=11.03 (s, 1H), 8.03 (s, 1H), 7.48 (s, 1H), 7.41 (d, 1H), 7.32 (d, 1H), 7.30 (s, 1H), 3.85 (t, 2H), 3.46 (t, 2H), 3.10 (s, 3H), 1.46 (s, 6H).

Probe 22:

The probe 22 was synthesized according to the procedure of probe 1 with a field of 85%. $^1$H-NMR (400 MHz, DMSO-$d_6$): δ=12.03 (s, 1H), 11.22 (s, 1H). 8.55 (t, 1H, J=5.8 Hz), 8.12 (s, 1H), 7.79 (s, 1H), 7.48 (s, 1H), 7.44 (d, 2H, J=7.9 Hz), 7.41 (d, 1H), 7.32 (d, 1H), 7.31 (s, 1H), 7.30 (d, 2H, J=7.9 Hz), 6.27 (s, 2H), 5.44 (s, 2H), 4.89 (t, 1H, J=5.6 Hz), 4.37 (d, 2H, J=5.8 Hz), 3.65 (t, 2H, J=5.6 Hz), 3.48 (t, 2H, J=5.6 Hz), 3.09 (s, 3H).

Example 23

Utilizing molecular motor as a viscosity responsive fluorescent dye, a fluorescent activated covalent probe 23 was constructed for SNAP protein taging:

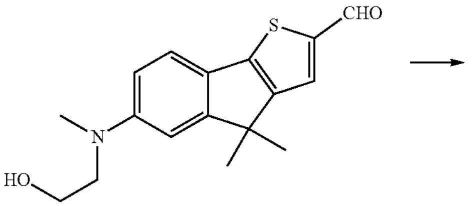

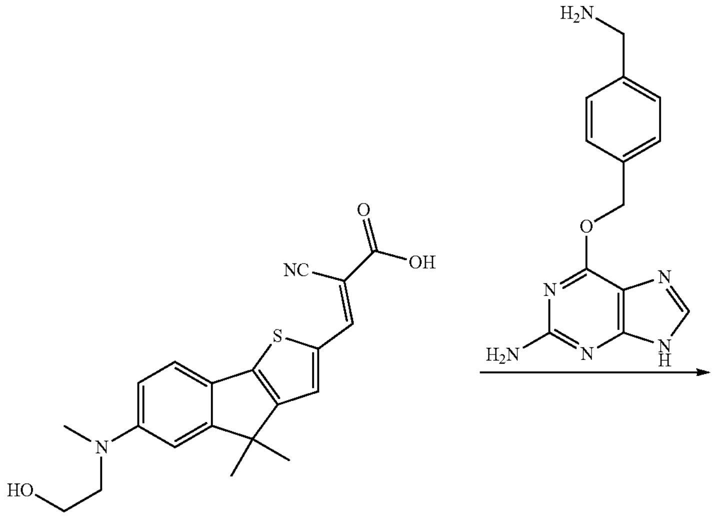

compound 35

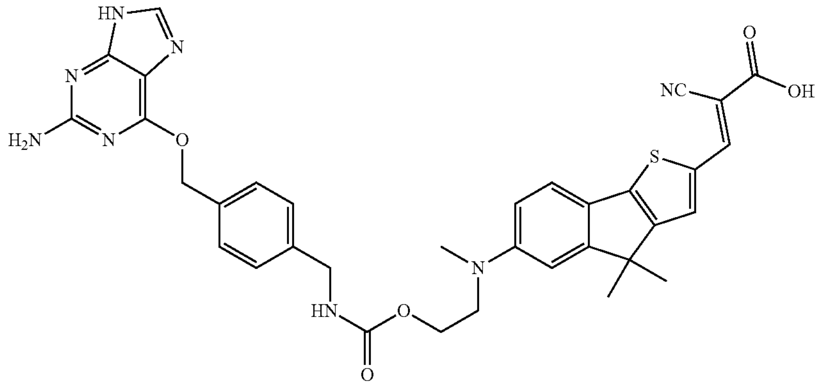

probe 23

Compound 35:

The compound 35 was synthesized according to the procedure of compound 2 with a field of 55%. $^1$H-NMR (400 MHz, $CDCl_3$): δ=8.03 (s, 1H), 7.48 (s, 1H), 7.41 (d, 1H), 7.32 (d, 1H), 7.30 (s, 1H), 3.85 (t, 2H), 3.46 (t, 2H), 3.10 (s, 3H), 1.46 (s, 6H).

Probe 23:

The probe 23 was synthesized according to the procedure of probe 1 with a field of 58%. $^1$H-NMR (400 MHz, DMSO-$d_6$): δ=13.58 (s, 1H), 12.22 (s, 1H), 8.55 (t, J=5.8 Hz, 1H), 8.12 (s, 1H), 7.79 (s, 1H), 7.48 (s, 1H), 7.44 (d, 2H, J=7.9 Hz), 7.41 (d, 1H), 7.32 (d, 1H), 7.31 (s, 1H), 7.30 (d, 2H, J=7.9 Hz), 6.27 (s, 2H), 5.44 (s, 2H), 4.89 (t, 1H, J=5.6 Hz), 4.37 (d, 2H, J=5.8 Hz), 3.65 (t, 2H, J=5.6 Hz), 3.48 (t, 2H, J=5.6 Hz), 3.09 (s, 3H).

Example 24

Utilizing molecular motor as a viscosity responsive fluorescent dye, a fluorescent activated covalent probe 24 was constructed for CLIP protein taging:

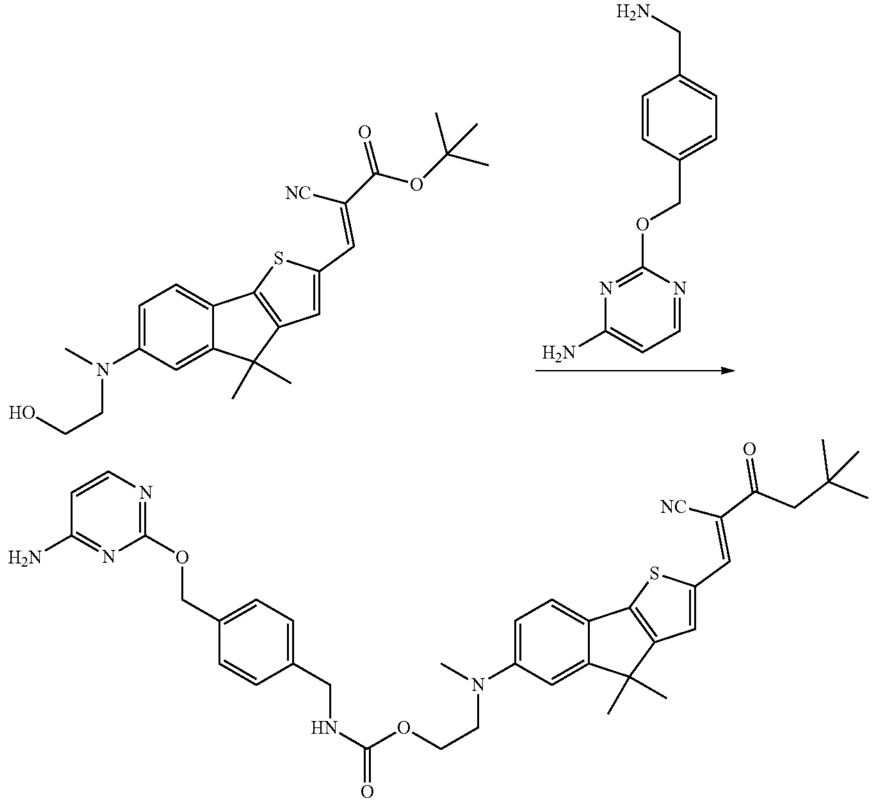
probe 24
Probe 24:
The probe 24 was synthesized according to the procedure of probe 1 with a field of 85%. $^1$H-NMR (400 MHz, DMSO-$d_6$): δ=8.03 (s, 1H), 7.86 (d, 1H), 7.74 (t, 3H), 7.48 (s, 1H), 7.41 (d, 1H), 7.36 (d, 2H, J=6.0 Hz), 7.32 (d, 1H), 7.30 (s, 1H), 7.26 (d, 2H, J=6.0 Hz), 6.85 (s, 2H), 6.08 (d, 1H), 5.20 (s, 2H), 4.24 (t, 2H), 4.15 (d, 2H), 3.66 (t, 2H), 3.14 (s, 3H), 1.54 (s, 9H), 1.42 (s, 6H).
Example 25
Utilizing molecular motor as a viscosity responsive fluorescent dye, a fluorescent activated covalent probe 25 was constructed for CLIP protein taging:
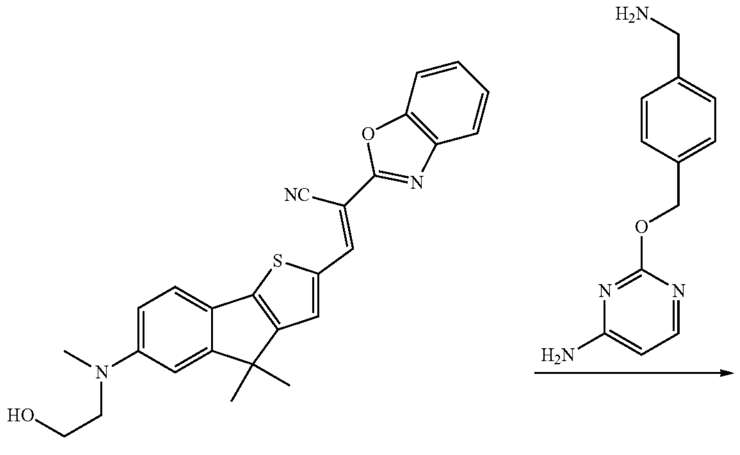

-continued

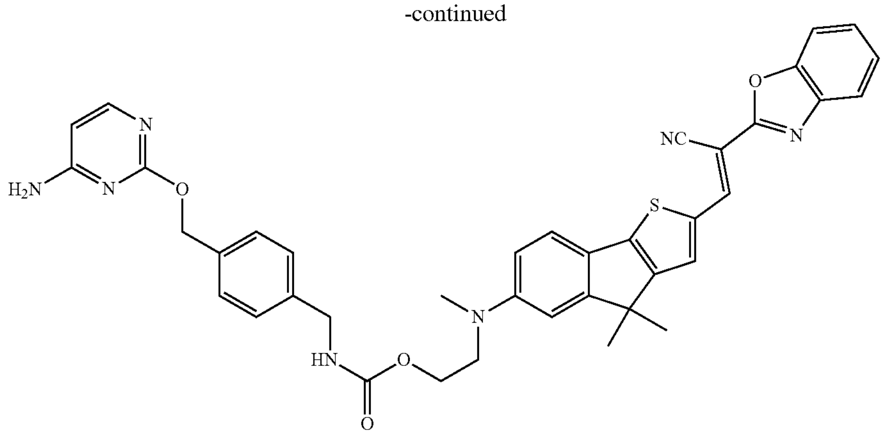

probe 25

Probe 25:

The probe 25 was synthesized according to the procedure of probe 1 with a field of 88%. $^{1}$H-NMR (400 MHz, DMSO-$d_6$): δ=7.93 (d, 1H, J=7.2 Hz), 7.89 (s, 1H), 7.79 (s, 1H), 7.74 (d, 1H, J=4.0 Hz), 7.55 (d, 1H, J=4.0 Hz), 7.42 (m, 2H), 7.41 (d, 1H), 7.32 (d, 1H), 7.31 (d, 2H, J=8.0 Hz), 7.18 (m, 3H), 6.96 (d, 2H, J=5.6 Hz), 6.06 (d, 1H, J=5.6 Hz), 5.27 (s, 2H), 5.15 (s, 2H), 4.45 (d, 2H, J=5.6 Hz), 3.85 (t, 2H, J=5.6 Hz), 4.12 (s, 2H), 3.60 (t, 2H, J=5.6 Hz), 3.10 (s, 3H), 1.50 (s, 6H).

Example 26

Utilizing molecular motor as a viscosity responsive fluorescent dye, a fluorescent activated covalent probe 26 was constructed for CLIP protein taging:

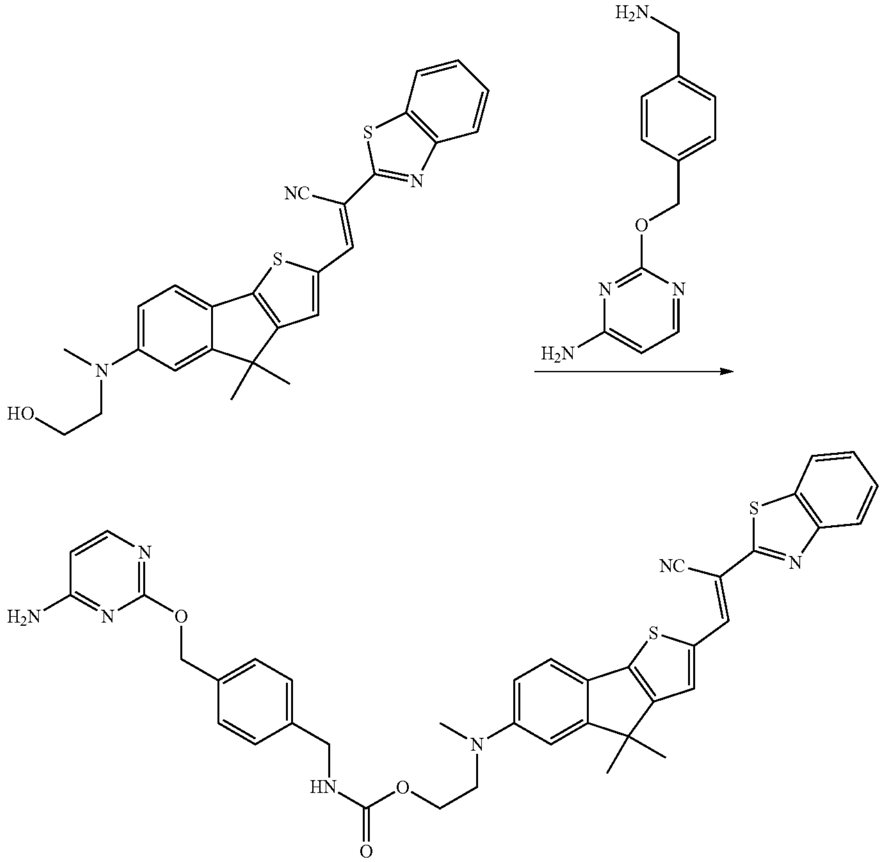

probe 26

Probe 26:

The probe 26 was synthesized according to the procedure of probe 1 with a field of 88%. $^1$H-NMR (400 MHz, DMSO-$d_6$): δ=8.18 (m, 1H), 8.03 (t, 1H), 8.01 (m, 1H), 7.94 (d, 1H), 7.74 (s, 2H), 7.54 (m, 1H), 7.53 (m, 3H), 7.16 (t, 2H), 7.11 (t, 2H), 6.83 (d, 1H), 6.81 (d, 1H), 6.64 (d, 1H), 6.19 (d, 1H), 5.16 (s, 2H), 4.48 (t, 2H), 4.29 (t, 2H), 4.23 (d, 2H), 2.75 (s, 3H), 1.72 (s, 6H).

Example 27

Utilizing molecular motor as a viscosity responsive fluorescent dye, a fluorescent activated covalent probe 27 was constructed for SNAP protein taging:

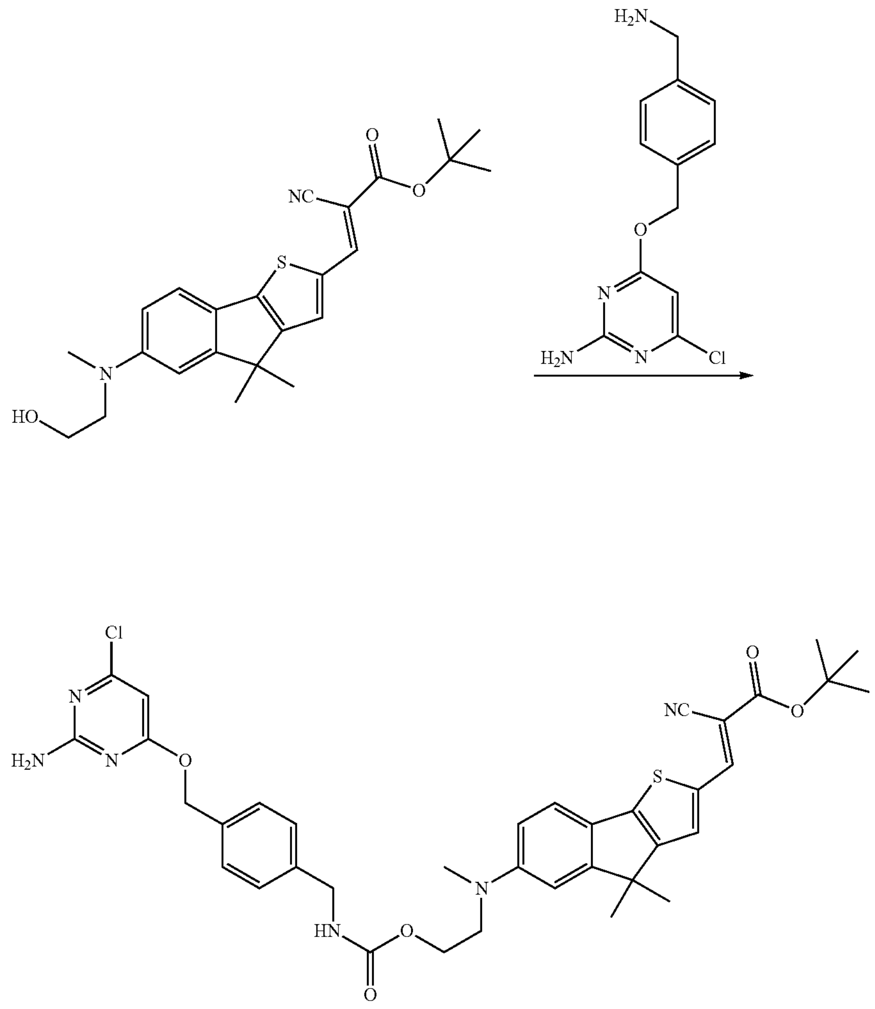

probe 27

Probe 27:

The probe 27 was synthesized according to the procedure of probe 1 with a field of 86%. $^1$H-NMR (400 MHz, DMSO-$d_6$): δ=8.18 (m, 1H), 8.03 (t, 1H), 8.01 (m, 1H), 7.94 (d, 1H), 7.74 (s, 2H), 7.54 (m, 1H), 7.53 (m, 3H), 7.48 (s, 1H), 7.41 (d, 1H), 7.32 (d, 1H), 7.30 (s, 1H), 7.16 (t, 2H), 7.11 (t, 2H), 6.83 (d, 1H), 6.81 (d, 1H), 6.64 (d, 1H), 6.19 (d, 1H) 5.16 (s, 2H), 4.48 (t, 2H), 4.29 (t, 2H), 4.23 (d, 2H), 2.75 (s, 3H), 1.72 (s, 6H).

Example 28

Utilizing molecular motor as a viscosity responsive fluorescent dye, a fluorescent activated covalent probe 28 was constructed for SNAP protein taging:

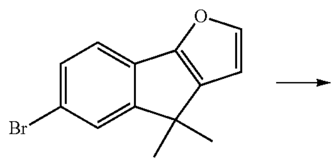

compound 36

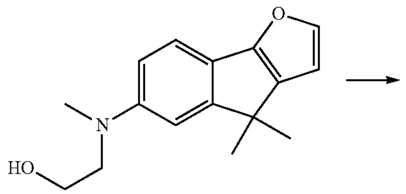

compound 37

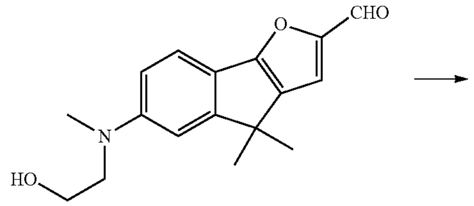

compound 38

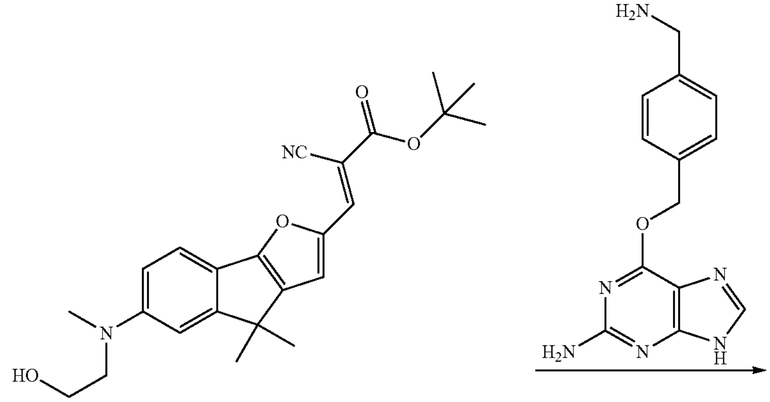

compound 39

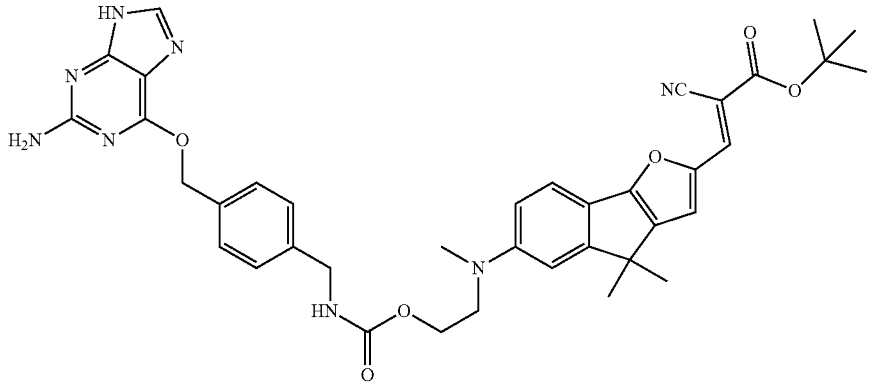

probe 28

Compound 36:

The compound 36 was prepared according to the previously reported procedure (Kimin Lim et al. J. Phys. Chem. C. 201, 115, 22640-22646). $^1$H-NMR (400 MHz, $CDCl_3$): δ=7.51 (s, 1H), 7.43 (d, 1H, J=8.1 Hz), 7.31 (d, 1H, J=5.1 Hz), 7.27 (d, 1H, J=7.8 Hz), 7.18 (d, 1H, J=4.5 Hz), 1.44 (s, 6H).

Compound 37:

The compound 37 was synthesized according to the procedure of compound 13 with a field of 56%. $^1$H-NMR (400 MHz, $CDCl_3$): δ=7.52 (s, 1H), 7.41 (d, 1H), 7.32 (d, 1H), 7.22 (d, 1H), 7.11 (d, 1H), 3.85 (t, 2H), 3.46 (t, 2H), 3.10 (s, 3H), 1.45 (s, 6H).

Compound 38:

The compound 38 was synthesized according to the procedure of compound 14 with a field of 70%. $^1$H-NMR (400 MHz, $CDCl_3$): δ=9.88 (s, 1H), 7.53 (s, 1H), 7.40 (d, 1H), 7.32 (d, 1H), 7.30 (s, 1H), 3.85 (t, 2H), 3.46 (t, 2H), 3.10 (s, 3H), 1.46 (s, 6H).

Compound 39:

The compound 39 was synthesized according to the procedure of compound 2 with a field of 95%. $^1$H-NMR (400 MHz, $CDCl_3$): δ=8.03 (s, 1H), 7.51 (s, 1H), 7.44 (d, 1H), 7.32 (d, 1H), 7.21 (s, 1H), 3.85 (t, 2H), 3.46 (t, 2H), 3.10 (s, 3H), 1.50 (s, 9H), 1.45 (s, 6H).

Probe 28:

The probe 28 was synthesized according to the procedure of probe 1 with a field of 75%. $^1$H-NMR (400 MHz, DMSO-$d_6$): δ=12.05 (s, 1H), 8.55 (t, 1H, J=5.8 Hz), 8.12 (s, 1H), 7.79 (s, 1H), 7.48 (s, 1H), 7.44 (d, 2H, J=7.9 Hz), 7.41 (d, 1H), 7.32 (d, 1H), 7.31 (s, 1H), 7.30 (d, 2H, J=7.9 Hz), 6.27 (s, 2H), 5.44 (s, 2H), 4.89 (t, 1H, J=5.6 Hz), 4.37 (d, 2H, J=5.8 Hz), 3.65 (t, 2H, J=5.6 Hz), 3.48 (t, 2H, J=5.6 Hz), 3.09 (s, 3H), 1.49 (s, 9H).

Example 29

Utilizing molecular motor as a viscosity responsive fluorescent dye, a fluorescent activated covalent probe 29 was constructed for CLIP protein taging:

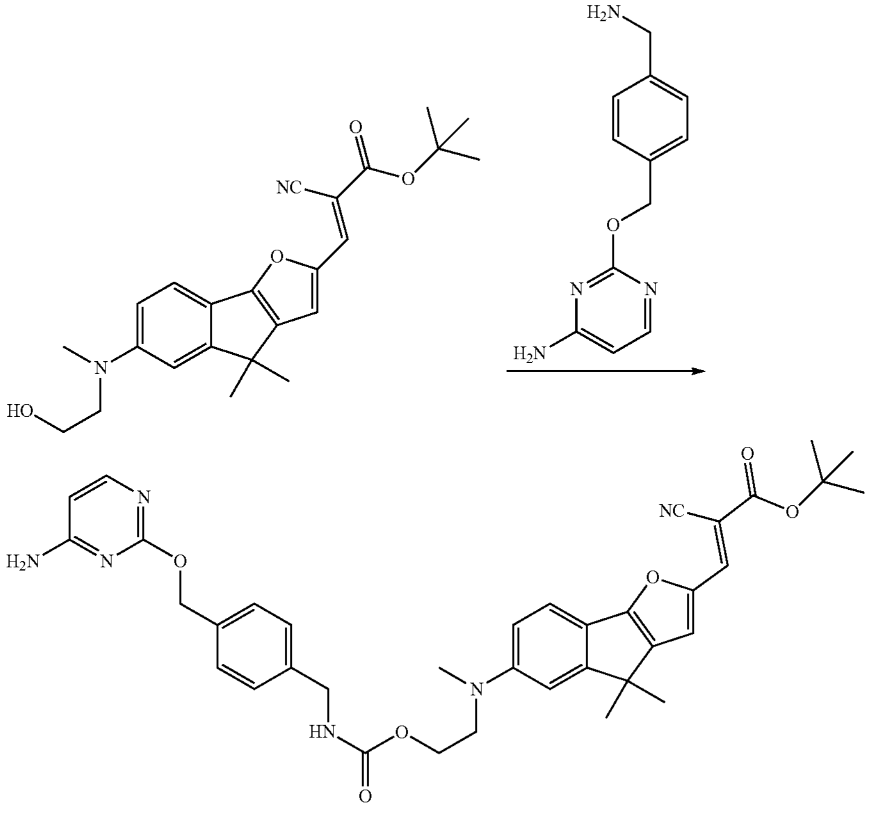

probe 29

Probe 29:

The probe 29 was synthesized according to the procedure of probe 1 with a field of 74%. $^1$H-NMR (400 MHz, DMSO-$d_6$): δ=8.05 (s, 1H), 7.68 (d, 1H), 7.58 (t, 3H), 7.45 (s, 1H), 7.43 (d, 1H), 7.29 (d, 2H, J=6.0 Hz), 7.27 (d, 1H), 7.24 (s, 1H), 7.11 (d, 2H, J=6.0 Hz), 6.85 (s, 2H), 6.08 (d, 1H), 5.20 (s, 2H), 4.24 (t, 2H), 4.15 (d, 2H), 3.66 (t, 2H), 3.15 (s, 3H), 1.46 (s, 9H).

Example 30

Utilizing molecular motor as a viscosity responsive fluorescent dye, a fluorescent activated covalent probe 30 was constructed for SNAP protein taging:

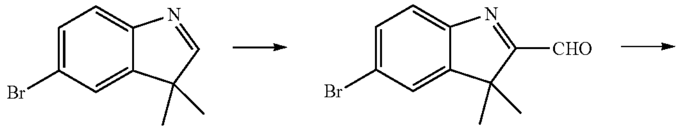

compound 40 compound 41

-continued

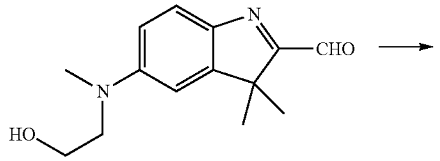

compound 42

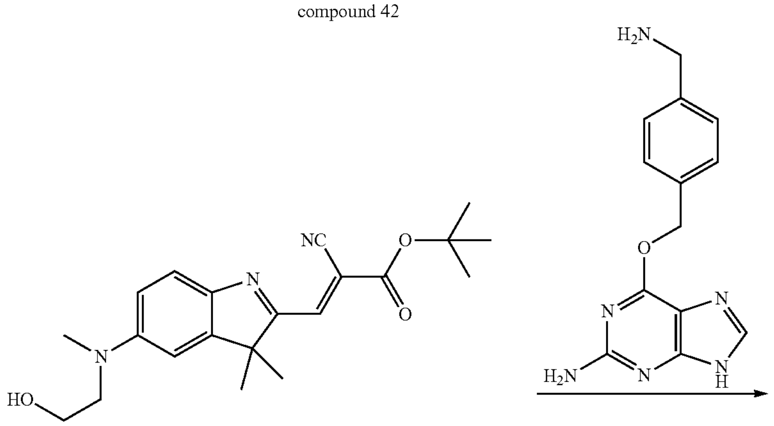

compound 43

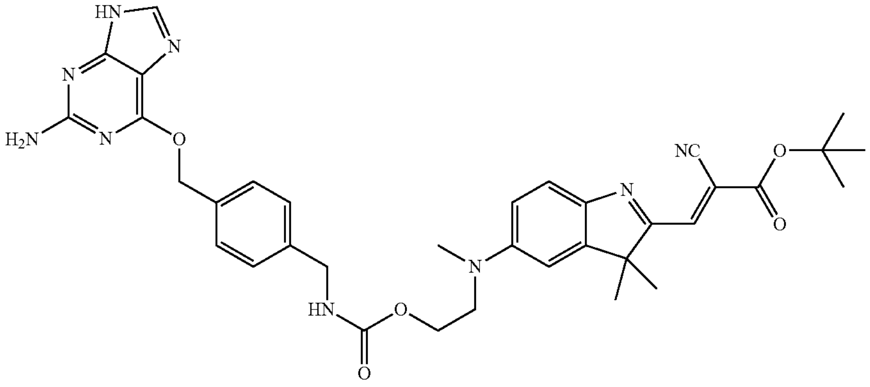

probe 30

Compound 40:

The compound 40 was prepared according to the previously reported procedure (Eric A. Owens et. al. Dyes and Pigments, 2015, 113, 27-37). $^1$H-NMR (400 MHz, $CDCl_3$): δ=7.76 (d, 1H), 7.60 (s, 1H), 7.03 (d, 1H), 2.34 (s, 3H), 1.42 (s, 6H).

Compound 41:

Compound 40 (0.474 g, 2 mmol) and stannic oxide (0.4 g) dissolved in 50 mL of 1,4-Dioxane and stirred at 80° C. for 3 h. After filtration, the system was added into 100 mL of water, and DCM (50 mL) was added for extraction twice. The organic phase was collected and dried by anhydrous sodium sulfate. After the solvent was removed under vacuum, the residue was collected and purified using a silica gel column to afford pure compound 41 (0.45 g) with the yield of 89%. $^1$H-NMR (400 MHz, $CDCl_3$): δ=9.74 (s, 1H), 7.76 (d, 1H), 7.60 (s, 1H), 7.03 (d, 1H), 1.42 (s, 6H).

Compound 42:

The compound 42 was synthesized according to the procedure of compound 13 with a field of 58%. $^1$H-NMR (400 MHz, $CDCl_3$): δ=9.74 (s, 1H), 7.76 (d, 1H), 7.60 (s, 1H), 7.03 (d, 1H), 3.85 (t, 2H, J=5.6 Hz), 3.60 (t, 2H, J=5.6 Hz), 3.10 (s, 3H), 1.42 (s, 6H).

Compound 43:

The compound 43 was synthesized according to the procedure of compound 2 with a field of 98%. $^1$H-NMR (400 MHz, $CDCl_3$): δ=8.05 (s, 1H), 7.76 (d, 1H), 7.60 (s, 1H), 7.03 (d, 1H), 3.85 (t, 2H, J=5.6 Hz), 3.60 (t, 2H, J=5.6 Hz), 3.10 (s, 3H), 1.45 (s, 9H), 1.42 (s, 6H).

Probe 30:

The probe 30 was synthesized according to the procedure of probe 1 with a field of 75%. $^1$H-NMR (400 MHz, DMSO-$d_6$): δ=12.10 (s, 1H), 8.55 (t, 1H, J=5.8 Hz), 8.12 (s, 1H), 7.79 (s, 1H), 7.76 (d, 1H), 7.60 (s, 1H), 7.44 (d, 2H, J=7.9 Hz), 7.30 (d, 2H, J=7.9 Hz), 7.03 (d, 1H), 6.27 (s, 2H), 5.44 (s, 2H), 4.89 (t, 1H, J=5.6 Hz), 4.37 (d, 2H, J=5.8 Hz), 3.65 (t, 2H, J=5.6 Hz), 3.48 (t, 2H, J=5.6 Hz), 3.09 (s, 3H), 1.49 (s, 9H), 1.42 (s, 6H).

Example 31

Utilizing molecular motor as a viscosity responsive fluorescent dye, a fluorescent activated covalent probe 31 was constructed for SNAP protein taging:

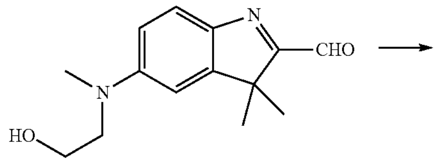

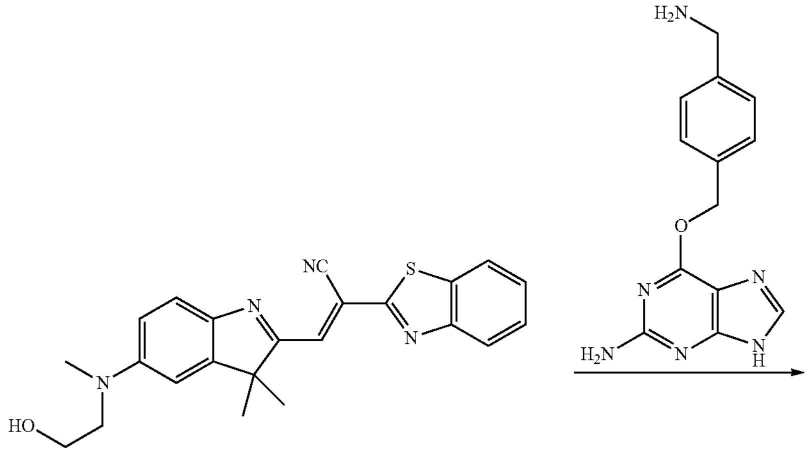

compound 44

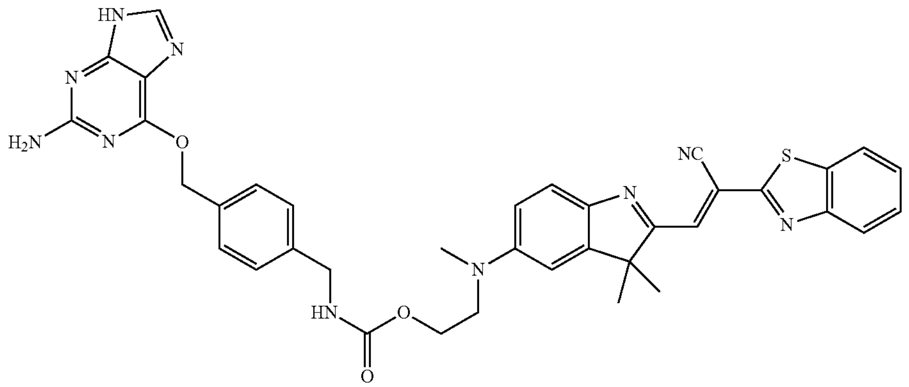

probe 31

Compound 44:

The compound 44 was synthesized according to the procedure of compound 2 with a field of 93%. $^{1}H$ NMR (400 MHz, DMSO-$d_6$): δ=8.33 (s, 1H), 7.74 (s, 1H), 7.64-7.71 (m, 2H), 7.41 (d, 1H), 7.35-7.38 (m, 2H), 7.22 (d, 1H), 4.90 (t, 1H, J=5.2 Hz), 3.66 (t, 2H, J=6.0 Hz), 3.47 (t, 2H, J=6.0 Hz), 3.10 (s, 3H), 1.41 (s, 6H).

Probe 31:

The probe 31 was synthesized according to the procedure of probe 1 with a field of 67%. $^{1}H$ NMR (400 MHz, DMSO-$d_6$): δ=8.45 (t, 1H, J=5.8 Hz), 8.20 (s, 1H), 7.79 (s, 1H), 7.73 (s, 1H), 7.64-7.71 (m, 2H), 7.44 (d, 2H, J=7.9 Hz), 7.41 (d, 1H), 7.35-7.38 (m, 4H), 7.32 (d, 1H), 6.27 (s, 2H), 5.44 (s, 2H), 4.90 (t, 1H, J=5.2 Hz), 4.37 (d, 2H, J=5.8 Hz), 3.66 (t, 2H, J=6.0 Hz), 3.47 (t, 2H, J=6.0 Hz), 3.10 (s, 3H), 1.41 (s, 6H).

Example 32

Utilizing molecular motor as a viscosity responsive fluorescent dye, a fluorescent activated covalent probe 32 was constructed for SNAP protein taging:

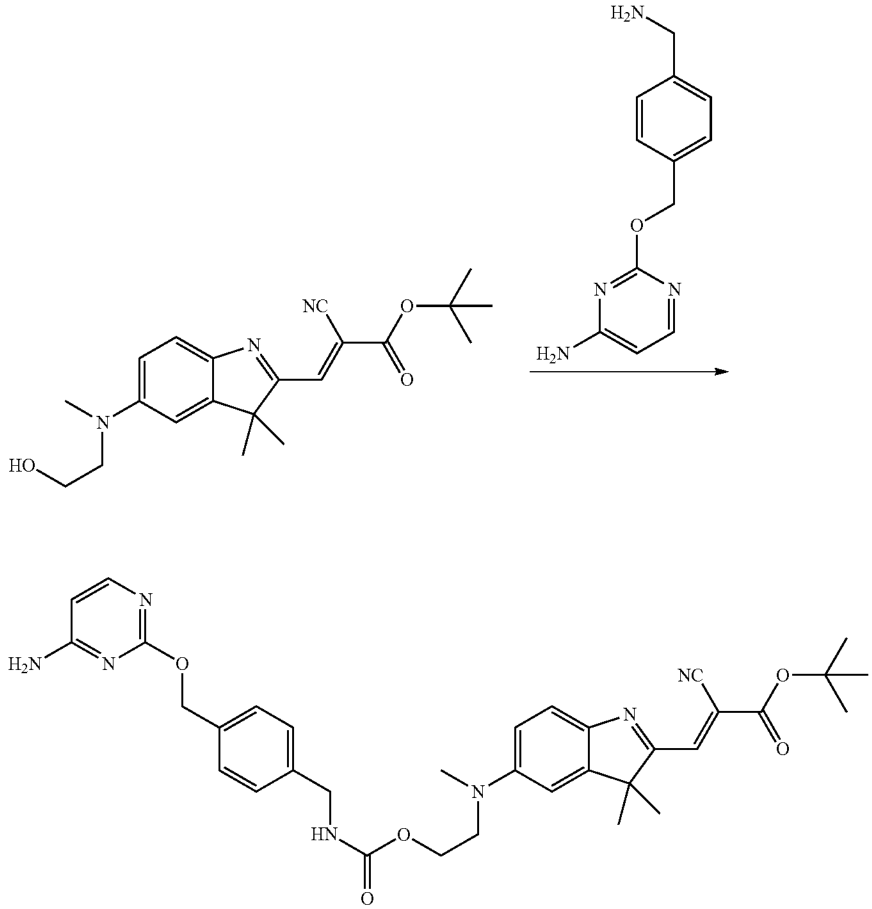

probe 32

Probe 32:

The probe 32 was synthesized according to the procedure of probe 1 with a field of 87%. $^1$H-NMR (400 MHz, DMSO-$d_6$): δ=8.03 (s, 1H), 7.86 (d, 1H), 7.74 (t, 3H), 7.48 (s, 1H), 7.41 (d, 1H), 7.36 (d, 2H, J=6.0 Hz), 7.32 (d, 1H), 7.26 (d, 2H, J=6.0 Hz), 6.85 (s, 2H), 6.08 (d, 1H), 5.20 (s, 2H), 4.24 (t, 2H), 4.15 (d, 2H), 3.66 (t, 2H), 3.14 (s, 3H), 1.54 (s, 9H), 1.42 (s, 6H).

Example 33

The Reference Probes BG-CCVJ and BG-Gly-CCVJ are prepared according to the method reported in literature (T. Y. Wang et. al. Chem Sci. 2016, 7, 301-307).

Respectively dissolve Probe 1-32 and Reference Probes BG-CCVJ and BG-Gly-CCVJ in dimethyl sulfoxide so as to prepare a mother liquid with a concentration of $1\times10^{-2}$M; add the mother liquid to glycerol and methanol respectively and mix them well to prepare a solution with a concentration of $1\times10^{-5}$ M. Based on different probes, the fluorescence emission spectrum of each probe are detected under the same conditions with maximum excitation wavelength of each probe. The results are shown in Table 1.

As shown in Table 1, the fluorescence emission wavelength ranges of the probes in Example 33 are wide, and their fluorescent intensities are quite different in glycerol and methanol. The probes are sensitive to the change of viscosity and have viscosity response.

Example 34

Mix the probe with corresponding protein tag to obtain the mixed sample, wherein the final concentration of probe in the mixed sample is 5 μM, and the final concentration of protein tags is 10 μM; hatch the mixed sample at 37° C. for 1 h, and detect its fluorescence intensity change by using the fluorescence spectrophotometer. The results are shown in Table 1.

According to the free probe quantum yield shown in Table 1, the fluorescence of the probes of and reference probes are extremely low before the reaction with the protein tag, and is close to the background fluorescence level of PBS buffer solution. It indicates that the fluorescence of the viscosity responsive fluorescent probe is not activated when the probe does not react with the protein tag. However, according to the quantum yield of the binding protein tag, the fluorescence signal enhancement can be detected in the corresponding excitation emission channel after the probe reacts with the protein tag with hundreds to one thousand fold fluorescence activation times and very high brightness; the reference probes also can activate fluorescence, but the fluorescence quantum yield and brightness after activation are quite low.

In summary, fluorescence can be activated after the probes in Example 34 are combined with the protein tag, and the probes have a fantastic fluorescence molecular switching property.

TABLE 1

The results of fluorescence emission spectra of various probes

| Name | Quantum yield of free probe | Quantum yield of binding protein tags | Emission wavelength/nm | Fluorescence activation multiple | Fluorescence ratio in glycerol methanol |
|---|---|---|---|---|---|
| Probe 1 | <0.001 | 0.41 | 550 | 490 | 562 |
| Probe2 | <0.001 | 0.44 | 630 | 556 | 790 |
| Probe 3 | <0.001 | 0.41 | 550 | 473 | 621 |
| Probe 4 | <0.001 | 0.39 | 550 | 567 | 601 |
| Probe 5 | <0.001 | 0.44 | 615 | 669 | 821 |
| Probe6 | <0.001 | 0.41 | 627 | 745 | 851 |
| Probe 7 | <0.001 | 0.45 | 666 | 701 | 814 |
| Probe 8 | <0.001 | 0.40 | 630 | 555 | 574 |
| Probe 9 | <0.001 | 0.61 | 580 | 911 | 890 |
| Probe 10 | <0.001 | 0.55 | 622 | 777 | 623 |
| Probe 11 | <0.001 | 0.56 | 627 | 771 | 560 |
| Probe 12 | <0.001 | 0.57 | 580 | 677 | 667 |
| Probe 13 | 0.0012 | 0.37 | 650 | 359 | 311 |
| Probe 14 | 0.001 | 0.35 | 725 | 498 | 402 |
| Probe 15 | 0.0012 | 0.35 | 651 | 265 | 301 |
| Probe 16 | <0.001 | 0.71 | 645 | 842 | 1421 |
| Probe 17 | <0.001 | 0.45 | 670 | 712 | 1084 |
| Probe 18 | <0.001 | 0.48 | 675 | 890 | 1123 |
| Probe 19 | <0.001 | 0.51 | 640 | 670 | 996 |
| Probe 20 | <0.001 | 0.44 | 665 | 910 | 1123 |
| Probe 21 | <0.001 | 0.39 | 680 | 451 | 542 |
| Probe 22 | <0.001 | 0.39 | 710 | 551 | 487 |
| Probe 23 | <0.001 | 0.33 | 643 | 433 | 512 |
| Probe 24 | <0.001 | 0.55 | 645 | 535 | 1125 |
| Probe 25 | <0.001 | 0.41 | 670 | 421 | 782 |
| Probe 26 | <0.001 | 0.46 | 675 | 478 | 522 |
| Probe 27 | <0.001 | 0.41 | 645 | 557 | 493 |
| Probe 28 | <0.001 | 0.67 | 651 | 857 | 1274 |
| Probe 29 | <0.001 | 0.57 | 652 | 933 | 1024 |
| Probe 30 | <0.001 | 0.41 | 675 | 503 | 412 |
| Probe 31 | <0.001 | 0.47 | 703 | 445 | 573 |
| Probe 32 | <0.001 | 0.41 | 675 | 421 | 553 |
| Reference probe BG-CCVJ | <0.001 | 0.02 | 501 | 170 | 260 |
| Reference probe BG-Gly-CCVJ | <0.001 | — | — | 60 | 260 |

Example 35

Add SNAP protein tag to the solution (30 μM) of Probe 1, Probe 5, Probe 13, Probe 16 and Probe 28 to prepare SNAP tags with final concentrations of 0.1 μM, 0.5 μM, 0.7 μM, 1.2 μM, 4.5 μM, 8.1 μM, 13.1 μM, and 14.8 μM; put the mixed sample solutions at 37° C. for 1 h, and detect the change of excitation emission spectrum of the sample by using the fluorescence spectrophotometer, and depict the relationship graph between SNAP protein tag concentration and fluorescence intensity according to the strength of emission spectrum. The results are shown in FIGS. 2-6.

As shown in FIGS. 2-6, there is a good linear relationship between the concentration of SNAP protein tag in a range of 0.1 μM to 14.8 μM and the probe fluorescence intensity. Thus the protein tag can be detected quantitatively according to the standard curve.

Example 36

Figure 7:
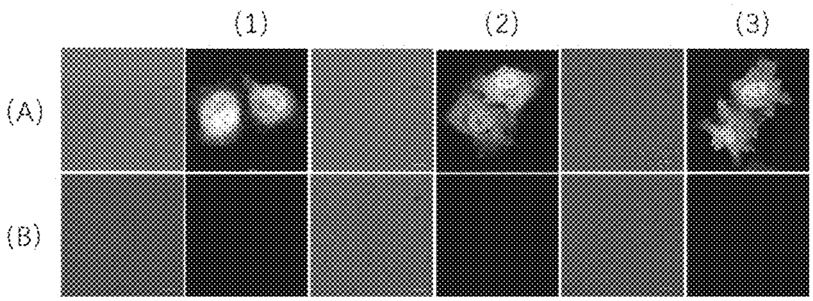
FIG. 7 is a fluorescence spectra of cells labeled with different probes, wherein (1)-(3) respectively correspond to Probe 16, Probe 17 and Probe 18, Group A are Hela cells with protein tags and Group B are Hela-WT cells (Hela primitive cells, without protein tags)

Take Hela cells as an example to detect the labeling effect of the compounds in mammalian cells. Hela cells and Hela-WT cells (Hela primitive cells without expressing protein tags), which can express protein tags stably, are planted in a glass bottom 96-well plate of 14 mm for 10 h. Add Probe 16, Probe 17 and Probe 18 into a culture medium respectively and dilute them to 5 μM. Hatch the cells in a carbon dioxide incubator at 37° C. for 2 h. Detect the fluorescence changes of labeled cells by using Leica TPS-8 confocal microscopy. As shown in FIG. 7B, no corresponding fluorescence signal is detected in Hela-WT cells after addition of the above probes, which indicates that the probe fluorescence is not affected by the intracellular environment; however, strong fluorescence signals are detected in Hela-WT cells expressing protein tags in group 7A, which are increased by nearly 700 times.

The above results indicate that the probe can specifically label the intracellular protein tag, and achieve fluorescence specific lighting. Meanwhile, the probe fluorescence is not affected by the intracellular environment.

Example 37

Figure 8:
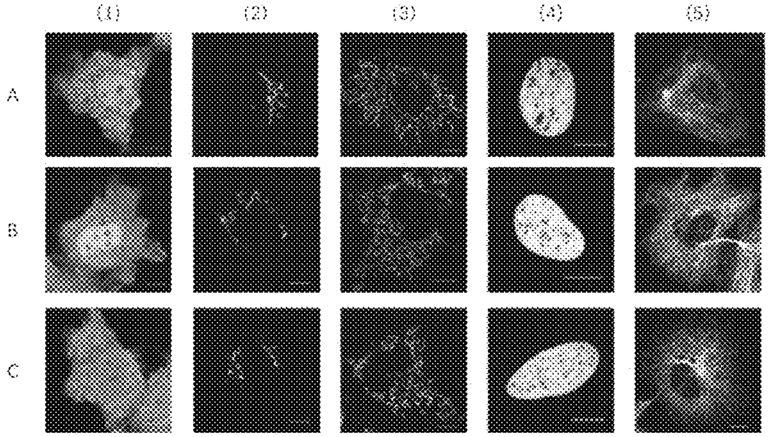
FIG. 8 is different organelles labeled by different probes, wherein Group A to C respectively correspond to Probe 16, Probe 17 and Probe 18, (1)-(5) are respectively matrix of cytoplasm, Golgi apparatus, mitochondria, chromosome and cytoskeleton.

In order to prove that Probe 16, Probe 17 and Probe 18 can be used to label target proteins located in different organelles, take Hela cells as an example to test the effect of different subcellular protein tags. Plant Hela cells (5000 cells/well) in a glass bottom plate of 96-well for 14 h, and then use Lipo2000 kit to transfect protein tags to locate plasmids in different organelles. After 24 h of transfection, remove the original culture medium, wash the culture medium twice with phenol free red DMEM culture medium, and hatch the cells with phenol free red medium containing probe (0.2 μM) for 2 h, and detect the effect of cell labeling by using Leica TCS-8 confocal microscopy imaging. As shown in FIG. 8, the probe can clearly display a variety of subcellular organelle structures without washing, including but not limited to matrix of cytoplasm, Golgi apparatus, mitochondria, chromosome and cytoskeleton.

These results indicate that the probe can serve as a powerful tool for subcellular organelle labeling.

Example 38

Figure 9:
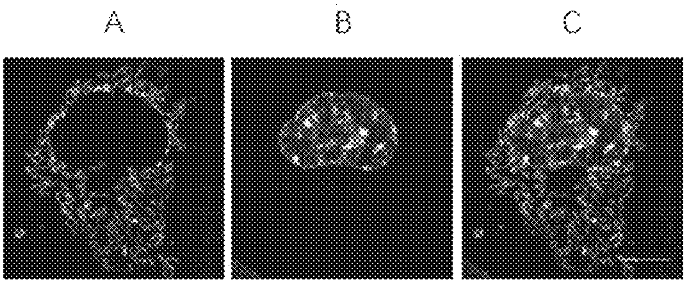
FIG. 9 is biocolor labels of the same cell by two different probes, wherein A is mitochondria labeled by Probe 16 and B is nucleus labeled by Probe 9, and C is the orthogonal imaging of A and B.

Plant Hela cells (5000 cells/well) in a glass bottom plate of 96-well for 14 h; transfect pcdna3.1-CLIP-histone (CLIP protein labeled chromosome localization plasmid) and pcdna3.1-mito-SNAP (SNAP protein labeled chromosome localization plasmid) by using Lipo2000 kit (0.1 μg/well). After 24 h of transfection, remove the original culture medium, and wash the culture medium twice with phenol free red DMEM culture medium, and hatch the cells respectively with phenol free red medium containing Probe 16 and Probe 9 (0.2 μM) for 2 h, and detect the effect of cell labeling by using Leica TCS-8 confocal microscopy imaging. As shown in FIG. 9, Probe 16 and Probe 9 can clearly and simultaneously display the structure of mitochondria and chromosomes without washing, and the co localization coefficient of chromosome fluorescence labeled by Probe 9 labeled and the mitochondrial fluorescence channel labeled by Probe 16 is less than 0.1, which indicates that there is no interference between two fluorescence channels.

The results show that the fluorescence spectra of different probes will not interfere with each other, and the orthogonal labeling imaging can be carried out simultaneously.

Example 39

Figure 10:
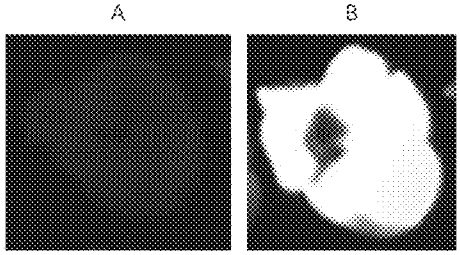
FIG. 10 is a label on the liver of living mice labeled by Probe 16, wherein A is the contrastive group and B is the sample group.

Firstly, introduce the plasmid pcdna3.1-SNAP (sample group) with SNAP protein expressing and the contrastive plasmid pcdna3.1-CAT (contrastive group) without SNAP protein expressing into mice. In this method, the plasmid is dissolved in a large volume of solution and rapidly injected into mice intravenously. The plasmid is absorbed by mouse liver, and then express the target protein. After 24 h of plasmid injection, inject the Probe 16 (0.4 μM) dissolved in 200 μL of PBS into mice intravenously to label SNAP protein tag. After 6 h, dissect the mice, and detect liver fluorescence differences by using Kodak multispectral vivo imaging system. As shown in FIG. 10, the liver fluorescence of mice injected with the contrastive plasmid pcdna3.1-CAT of Probe 16 is very low, while that of mice injected with the plasmid pcdna3.1-SNAP of Probe 16 have strong fluorescence with an intensity of more than 20 fold of the contrastive group.

So the fluorescence of the probe is not affected by the internal environment of animals, can be applied to live animals and can specifically label the SNAP protein tag expressed in the liver, and generate strong fluorescence signal.

Example 40

Figure 11:
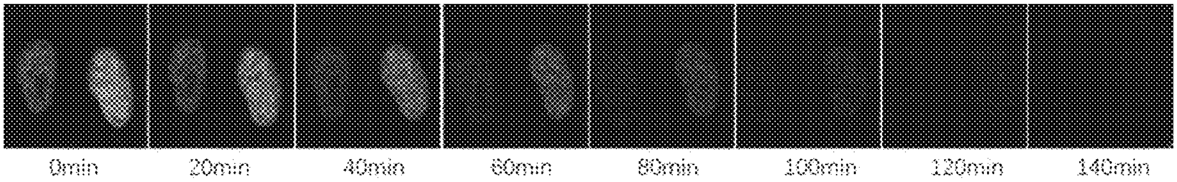
FIG. 11. is the fluorescence changes of Probe 16 with protein degradation in mammalian cells.

In order to verify that the fluorescence activation of the probe is related to the existence of protein, SNAP protein of mammalian cells is taken as an example, and AID degradation system is an example of detecting the fluorescence changes of probes combined with SNAP after protein degradation in Hela cells. Firstly, plant Hela cells (20000/$cm^2$) in a glass bottom cell culture medium of 20 mm for 14 h, and then transect the plasmids pcdna3.1-TIR1 and pcdna3.1-SNAP-IAA17-H2B by means of Lipofectmain2000 transfection reagent (Invertogen Co.). After the cells are transfected for 24 h, replace the cells labeled by the original cell culture medium with phenol red DMEM culture medium containing Probe 16 (1 μM), and hatch the cee sample in a carbon dioxide incubator at 37° C. for 1 h. After labeling, detect the fluorescence signal of the labeled cells by using Leica SP8 laser confocal microscopy imaging, and add indoleacetic acid (IAA) to induce the protein degradation of SNAP-IAA17-H2B, and detect the changes of cell fluorescence during protein degradation. As shown in FIG. 11, SNAP-IAA17-H2B protein is localized in the nucleus (0 min), and IAA is added to induce the protein degradation. As time goes by, the fluorescence signal of SNAP-IAA17-H2B protein gradually decreases, and is almost negligible after IAA has been added for 140 min, wherein the protein degradation rate is consistent with the results reported in literature. The above results show that the fluorescence properties of the probe in mammalian cells also depend on the presence of protein, The fluorescence is activated when the protein exists, and disappears when the protein is degraded, and this can be used to track and monitor the degradation process of the target protein.

Example 41

Figure 12:
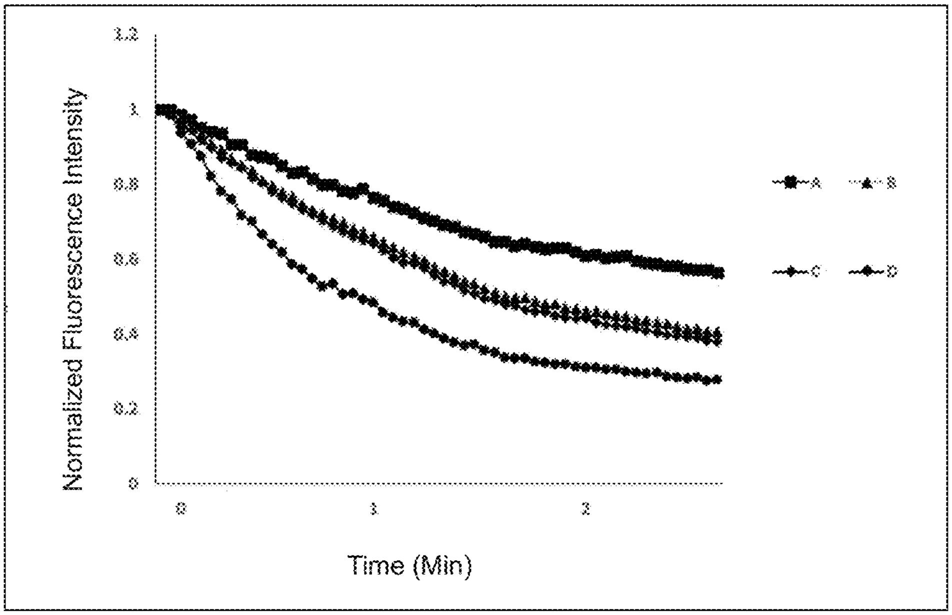
FIG. 12. is the contrast of photostability of SNAP protein and fluorescent protein IFP682 labeled by Probe 16, Probe 17 and Probe 18 in mammalian cells, wherein A-C are respectively Probe 16, Probe 17 and Probe 18, and D is IFP682.

To verify the excellent photo-bleaching resistance of the probes, SNAP protein of mammalian cells is taken as an example, and the photostabilities of Probe 16, Probe 17 and Probe 18 after labeling proteins in Hela cells are detected; meanwhile, the fluorescent protein IFP682 is expressed, and their photostabilities are contrasted under the same conditions. Plant Hela cells (5000 cells/well) in a glass bottom plate of 96-well for 12 h, and transect SNAP or fluorescent protein expressing histone specific, and use Leica SP8 laser confocal microscopy imaging after 36 h, and use 633 nm laser with an output power of 200 μW for shooting (2× zoom, 93 μm*93 μm, scanning voltage 600 V, 0.833 s/frame). FIG. 12 shows the variation of fluorescence intensity following the bleaching time, in which A to C are respectively Probe 16, Probe 17 and Probe 18, and D is fluorescent protein IFP682. It is shown in FIG. 12 that the bleaching resistance of Probe 16, Probe 17 and Probe 18 is significantly better than that of IFP682 reported in previous literature.

Example 42

Use molecular motor as a viscosity responsive fluorescent dye, and construct a fluorescent activated covalent Reference Probe 33 suitable for SNAP protein tagging (prepared according to the method in CN107641121A):

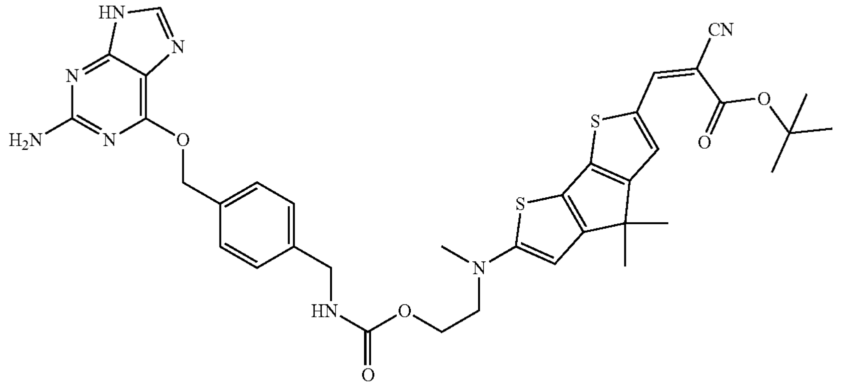

Reference Probe 33

The Reference Probe 33 is prepared according to the method disclosed in patent (CN107641121A) with a field of 45%. 1H-NMR (400 MHz, DMSO-$d_6$): δ=12.42 (s, 1H), 10.01 (s, 1H), 7.89 (s, 1H), 7.18 (s, 1H), 7.81 (s, 1H), 7.4 (m, 4H), 6.96 (d, 2H, J=5.6 Hz), 6.29 (s, 2H), 5.46 (s, 2H), 4.40 (d, 2H, J=4.8 Hz), 3.85 (t, 2H, J=5.6 Hz), 3.60 (t, 2H, J=5.6 Hz), 3.10 (s, 3H), 1.50 (m, 15H).

Figure 13:
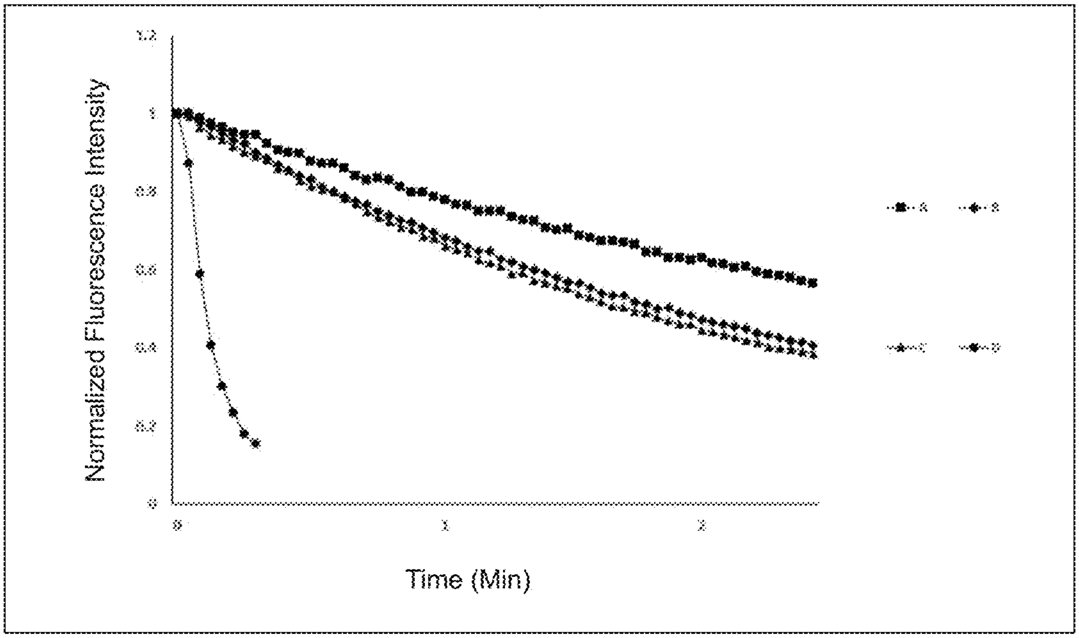
FIG. 13 is the contrast of photostability of SNAP protein labeled by Probe 16, Probe 17, Probe 18 and Reference Probe 33 in mammalian cells, wherein A-C are respectively Probe 16, Probe 17 and Probe 18, and D is Reference Probe 33.

To verify the excellent photo-bleaching resistance of Probe 16, Probe 17 and Probe 18, SNAP protein of mammalian cells is taken as an example, and the photostabilities of Probe 16, Probe 17, Probe 18 and Reference Probe 33 after labeling proteins in Hela cells are detected; meanwhile, and their photostabilities are contrasted under the same conditions. Plant Hela cells (5000 cells/well) in a glass bottom plate of 96-well for 12 h, and transect SNAP protein expressing histone specific, and use Leica SP8 laser confocal microscopy imaging after 36 h, and use 633 nm laser with an output power of 200 μW for shooting (2× zoom, 93 μm*93 μm, scanning voltage 600 V, 0.833 s/frame). FIG. 13 shows the variation of fluorescence intensity following the bleaching time, in which A to C are respectively Probe 16, Probe 17 and Probe 18, and D is Reference Probe 33. It is shown in FIG. 13 that the bleaching resistance of Probe 16, Probe 17 and Probe 18 is significantly better than that of Reference Probe 33 reported in the patent.

The above experiments show that the probe fluorescence of the present invention has excellent bleaching resistance, whose photostability is obviously better than that of the disclosed Reference Probe 33.

Example 43

Figure 14:
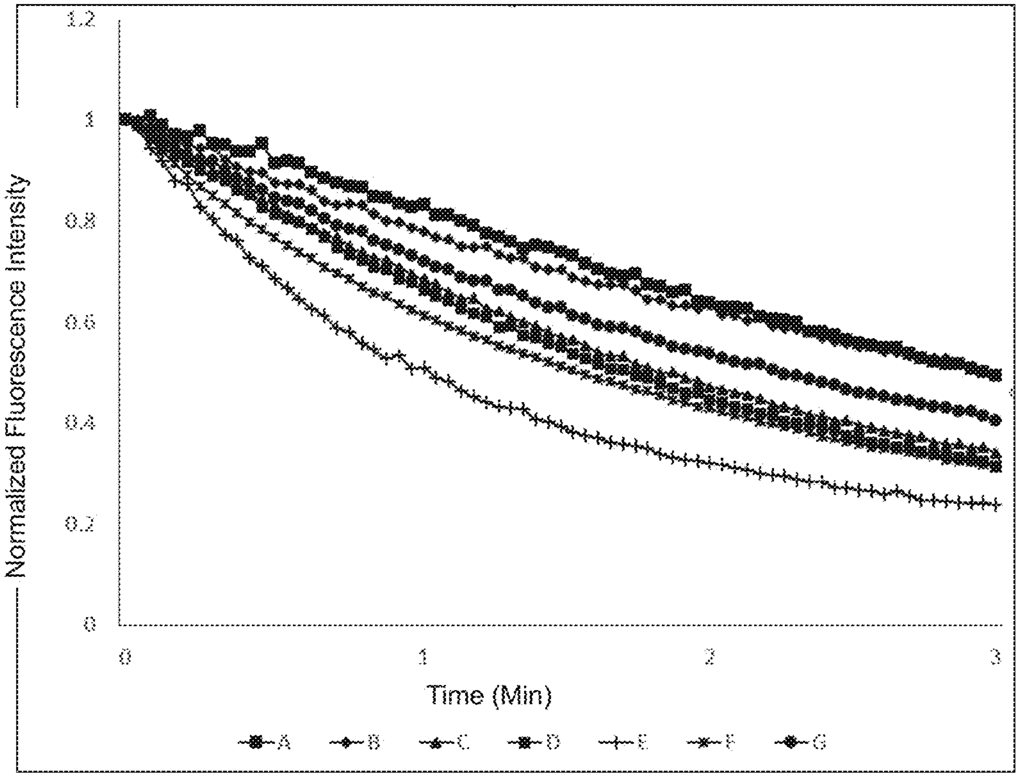
FIG. 14 is the contrast of photostability of SNAP protein labeled by Probe 2, Probe 5, Probe 11, Probe 13, Probe 16, Probe 28 and Probe 30 in mammalian cells, wherein A-G are respectively Probe 16, Probe 28, Probe 5, Probe 11, Probe 30, Probe 2 and Probe 13.

To verify the excellent photo-bleaching resistance of the probes formed by conjugation system B of formulae (I-1-1)-(I-1-7) with different electron acceptors, Probe 2, Probe 5, Probe 11, Probe 13, Probe 16, Probe 18 and Probe 30, as well as SNAP protein of mammalian cells are taken as an example, and the photostabilities of probes after labeling proteins in Hela cells are detected. Plant Hela cells (5000 cells/well) in a glass bottom plate of 96-well for 12 h, and transect SNAP or fluorescent protein expressing histone specific, and use Leica SP8 laser confocal microscopy imaging after 36 h, and use 633 nm laser with an output power of 200 μW for shooting (2× zoom, 93 μm*93 μm, scanning voltage 600 V, 0.833 s/frame). FIG. 14 shows the variation of fluorescence intensity following the bleaching time, in which A to G are respectively Probe 16, Probe 28, Probe 5, Probe 11, Probe 30, Probe 2 and Probe 13. It is shown in FIG. 14 that the probes have strong bleaching resistance after labeling protein.

The above experiments show that the probe fluorescence of the invention has excellent bleaching resistance.

What is claimed is:

1. A fluorescent probe having a structure represented by formula (I):

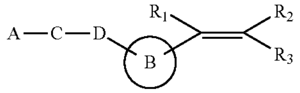

(I)

wherein:

the A is selected from the following structures:

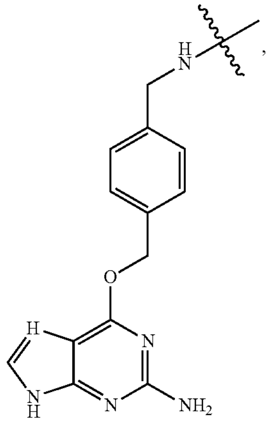

,

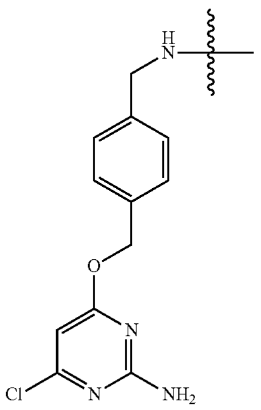

and

-continued
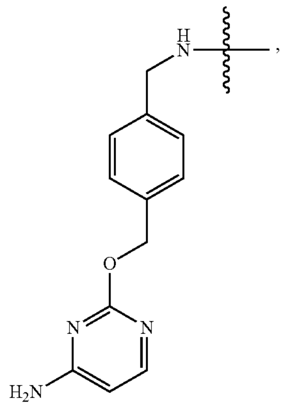
the C is —(C═O)—O—$CH_2$—;
the D is
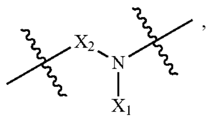
$X_1$ is selected from hydrogen and a $C_1$-$C_{30}$ linear or branched alkyl, $X_2$ is a $C_1$-$C_{30}$ linear or branched alkylene;
the B has any one of structures represented by formula (I-1-1) to (I-1-2) and formula (I-1-4) to (I-1-7):
(I-1-1)
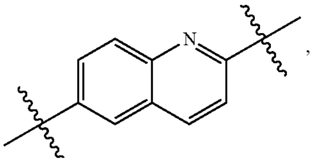
(I-1-2)
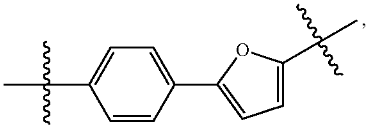
(I-1-4)
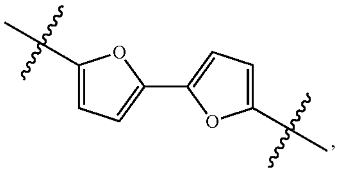
(I-1-5)
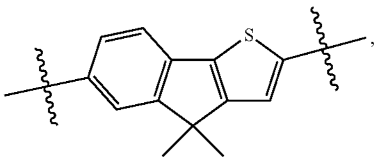
-continued
(I-1-6)
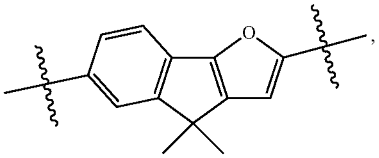
(I-1-7)
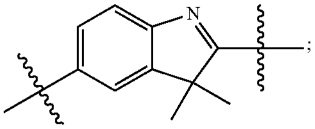
a structural part of formula (I) as shown in formula (I-2) has any one of the following formula (I-2-1) to (I-2-11), (I-2-13), (I-2-15) and (I-2-18):
(I-2)
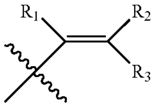
(I-2-1)
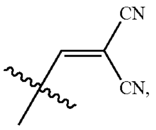
(I-2-2)
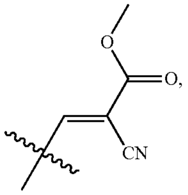
(I-2-3)
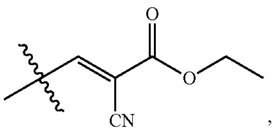
,
(I-2-4)
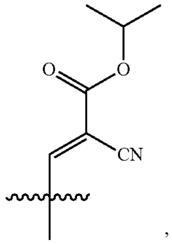
,
(I-2-5)
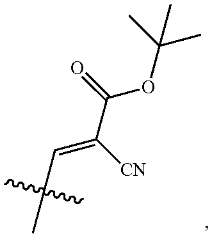
, -continued
(I-2-6)
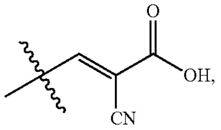
(I-2-7)
(I-2-8)
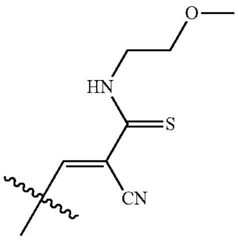
,
(I-2-9)
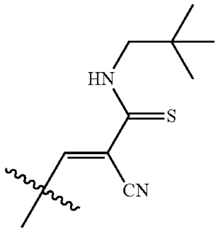
,
(I-2-10)
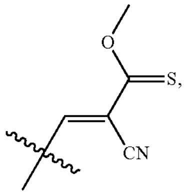
-continued
(I-2-11)
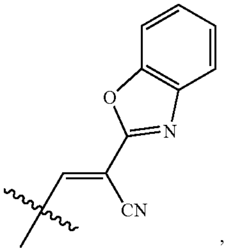
,
(I-2-13)
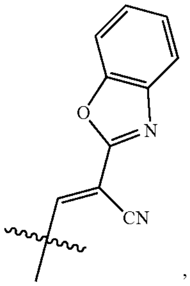
,
(I-2-15)
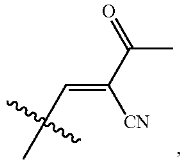
,
(I-2-18)
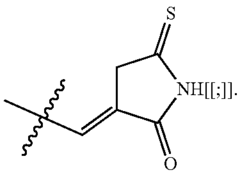
2. The fluorescent probe according to claim 1, wherein the fluorescent probe has a structure selected from a group consisting of
probe 1
1
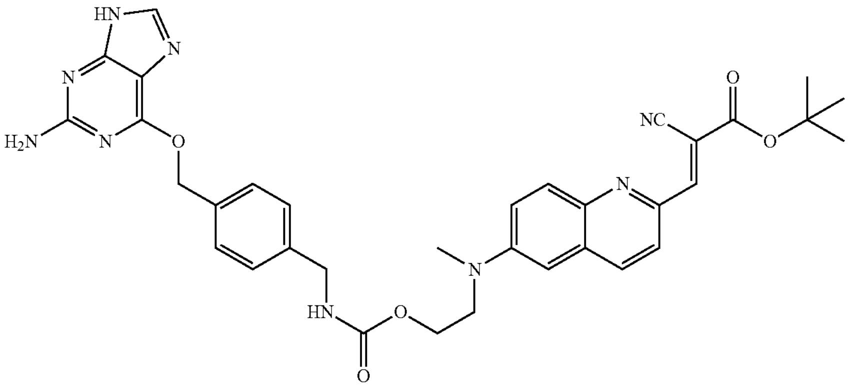

-continued
probe 2
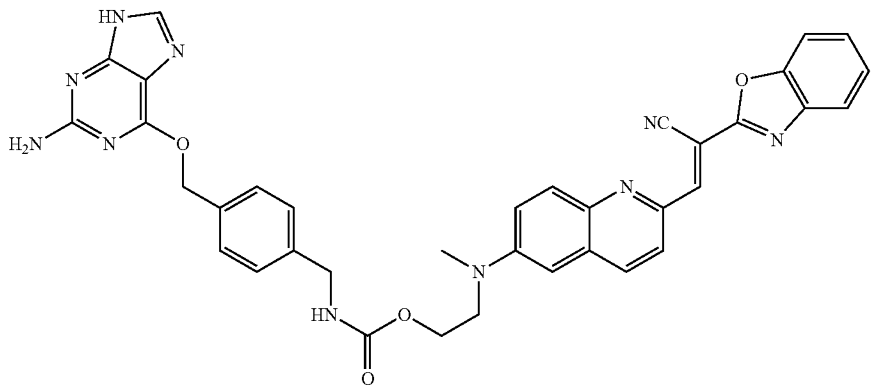
2
probe 3
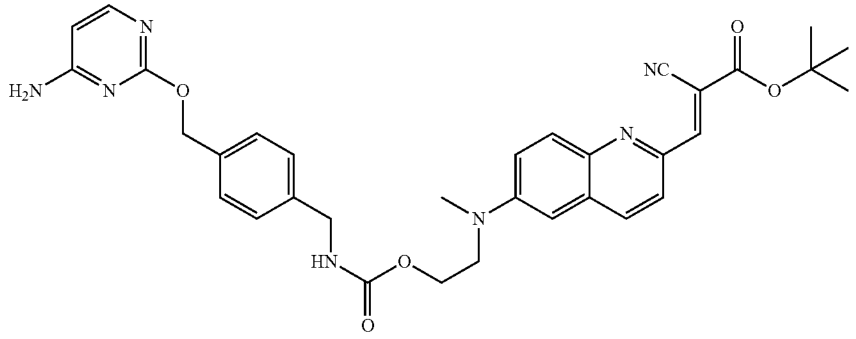
3
probe 4
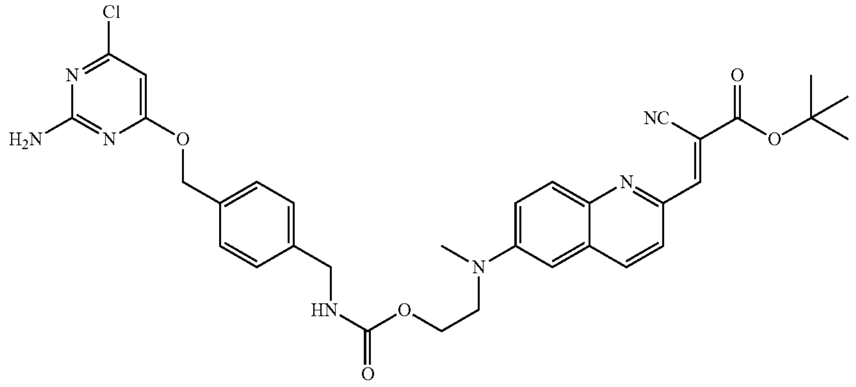
4

-continued
probe 5
5
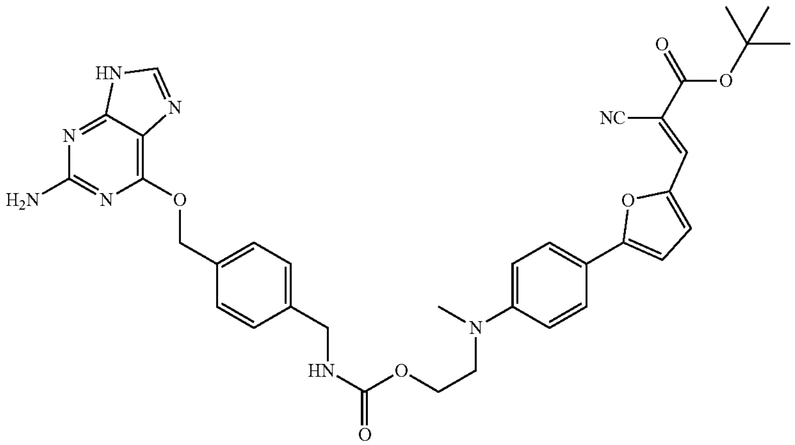
probe 6
6
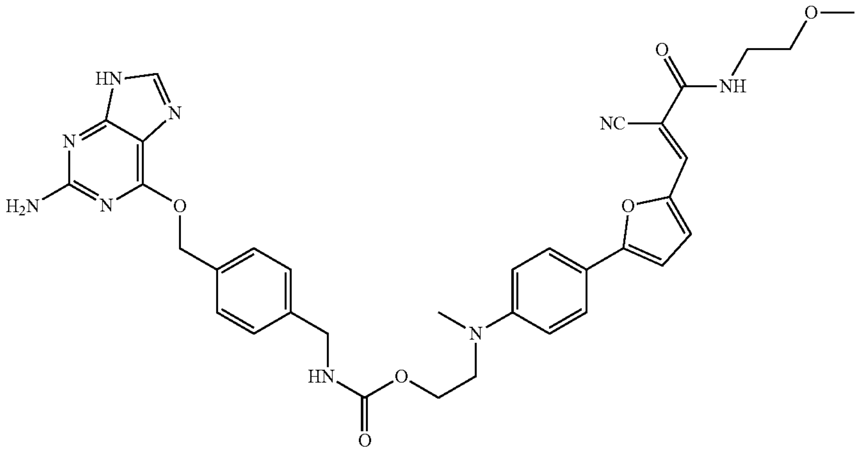
probe 7
7
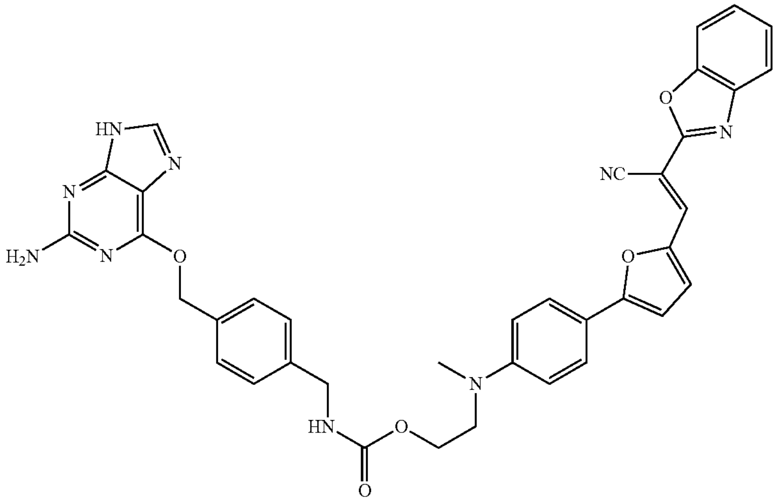

-continued
probe 8
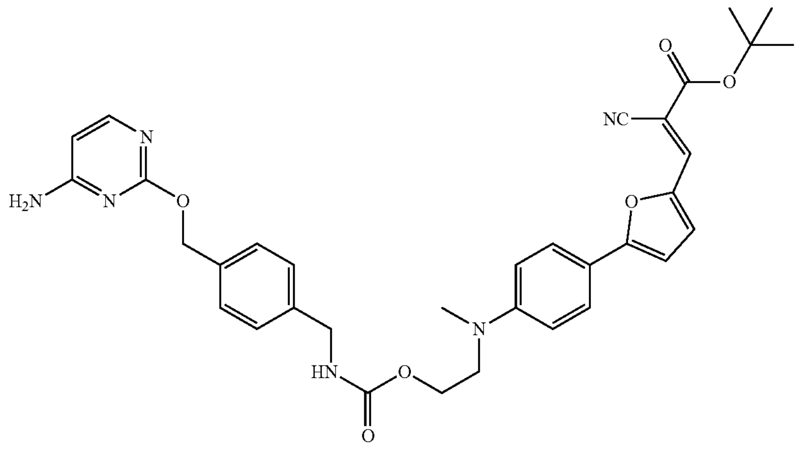
8
probe 13
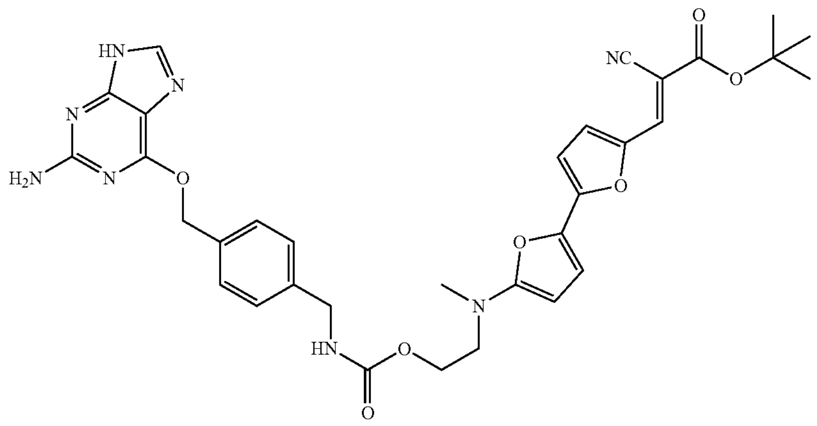
13
probe 14
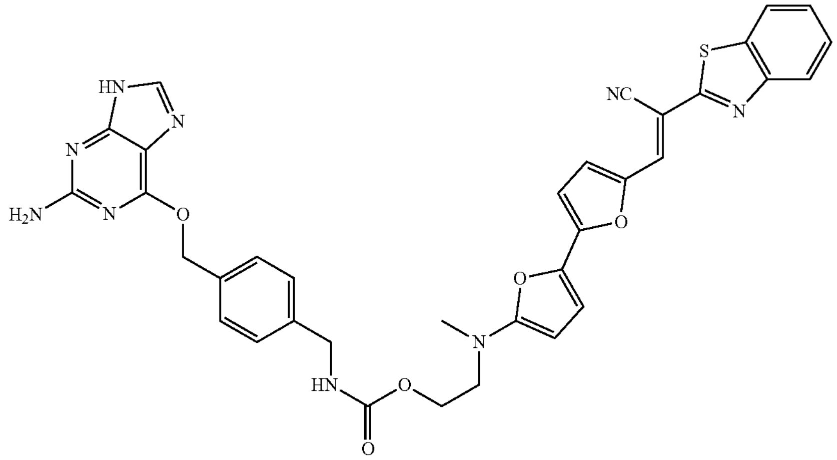
14

-continued
probe 15
15
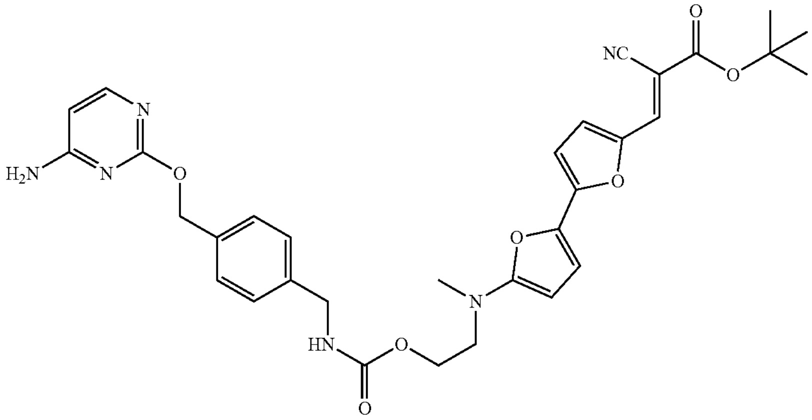
probe 16
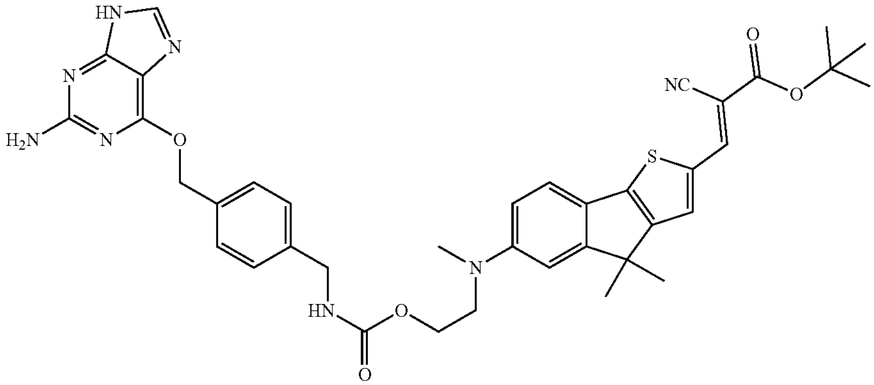
probe 17
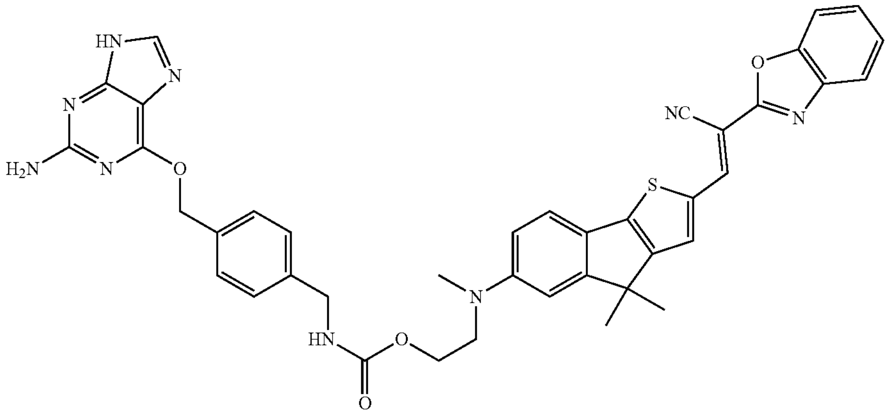

-continued
probe 18
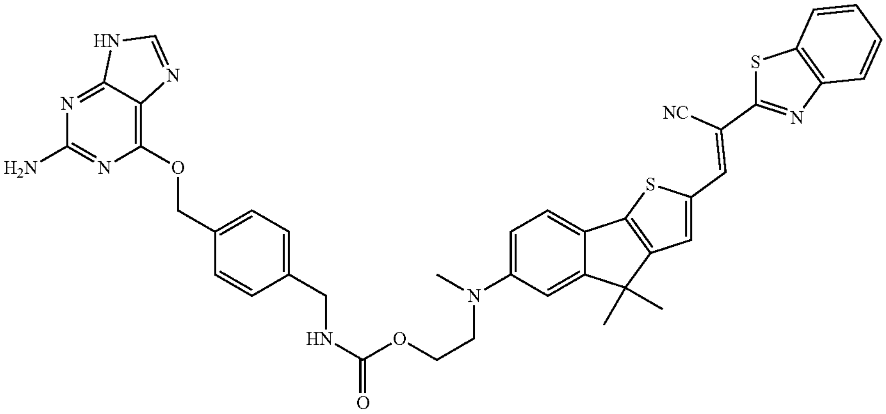
probe 19
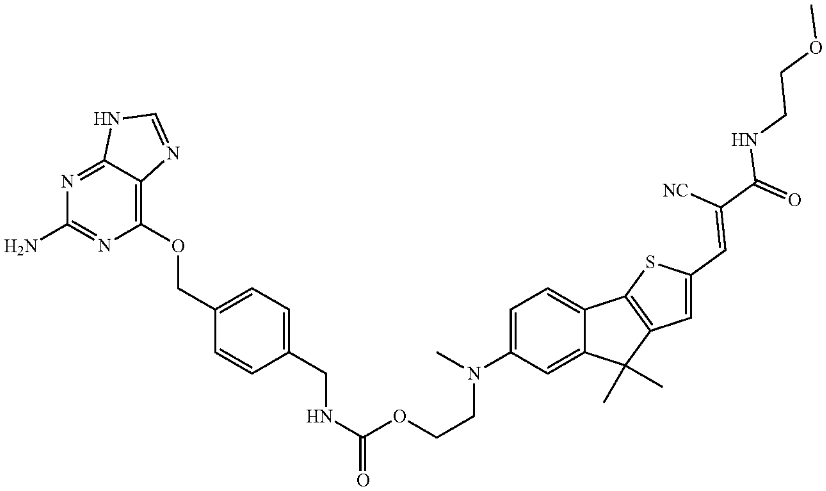
probe 20
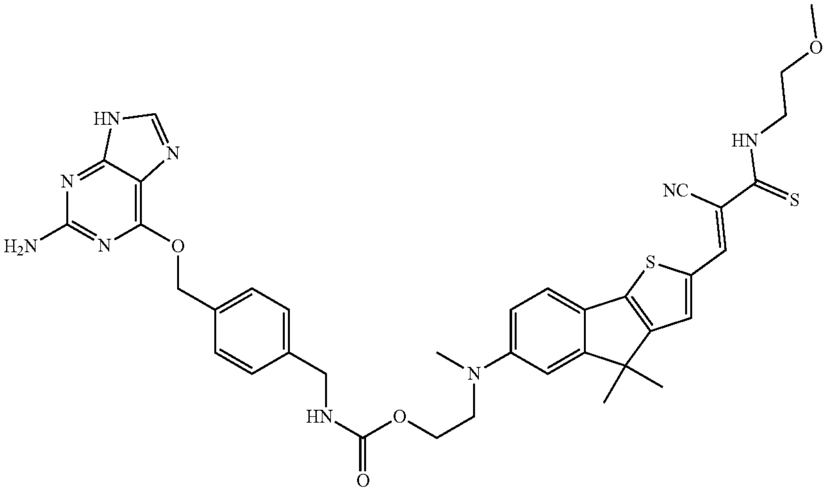

-continued
probe 21
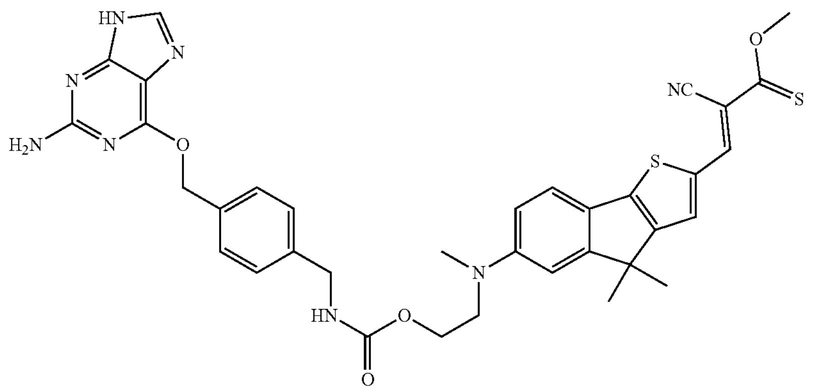
probe 22
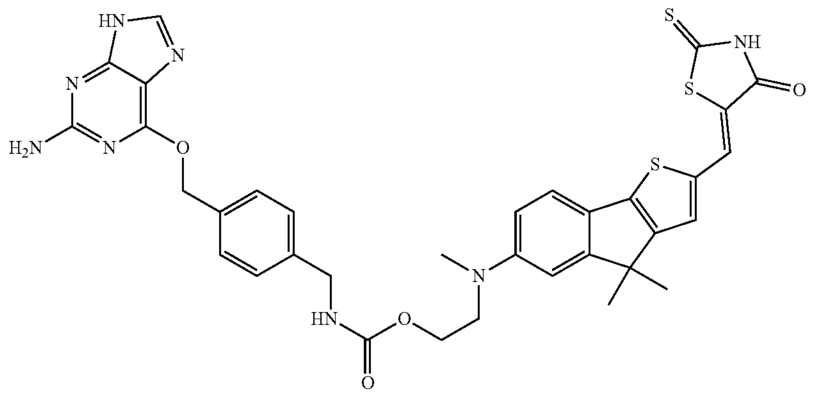
probe 23
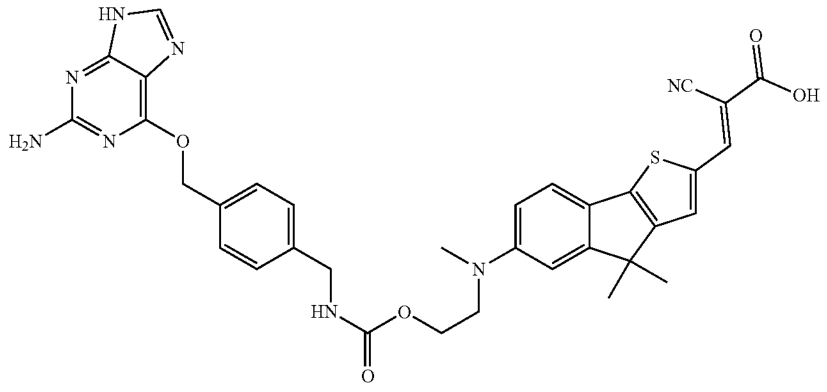
probe 24
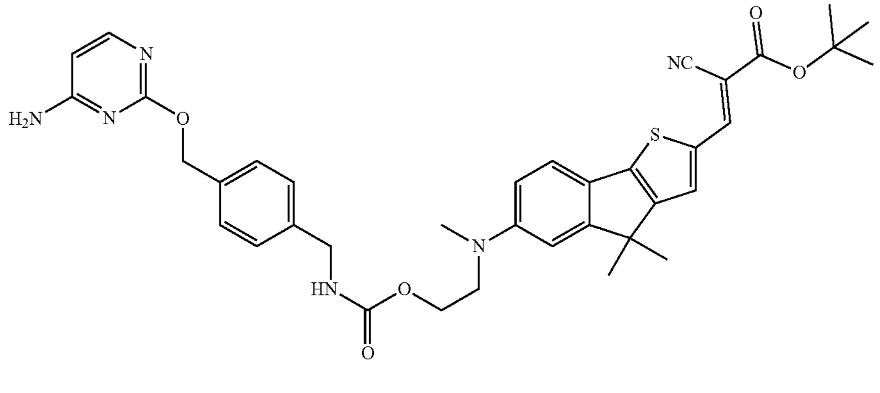

-continued
probe 25
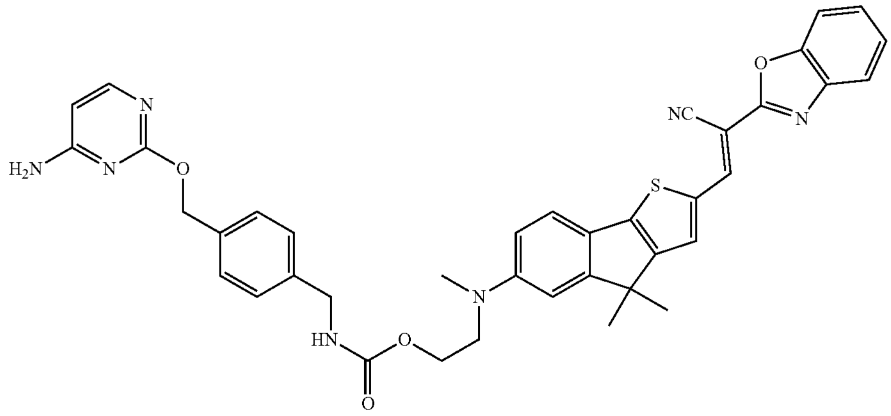
probe 26
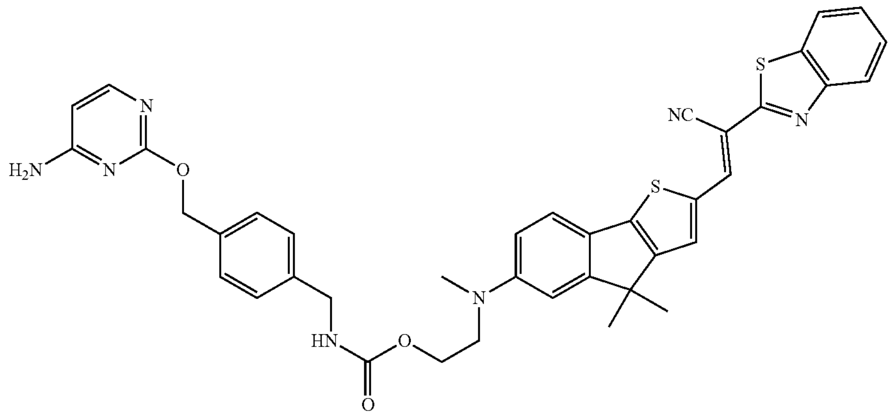
probe 27
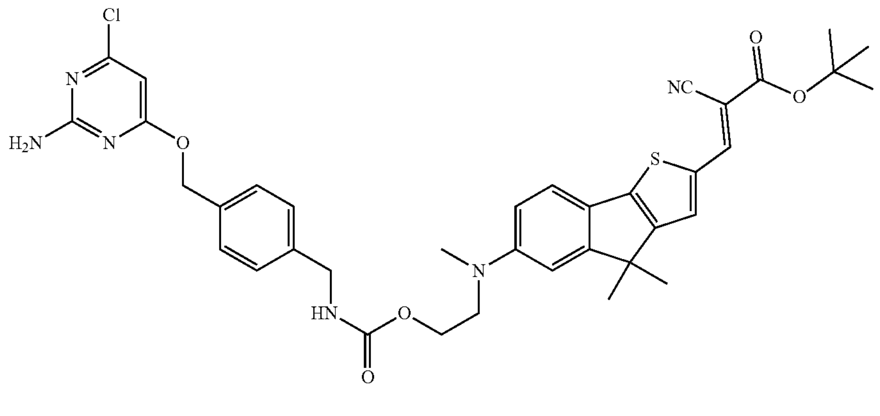

-continued
probe 28
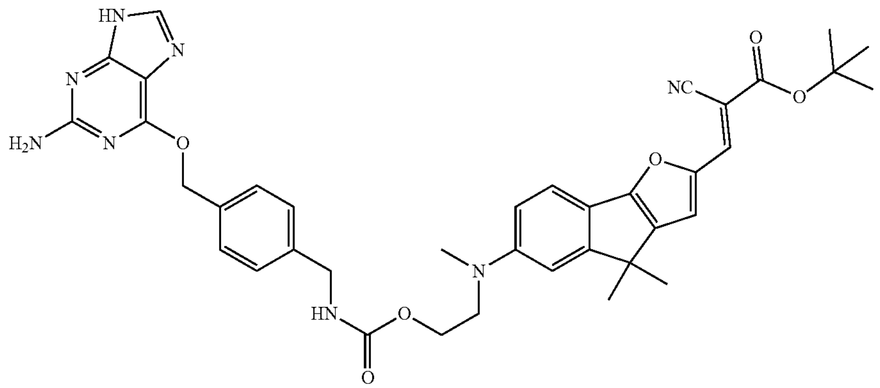
probe 29
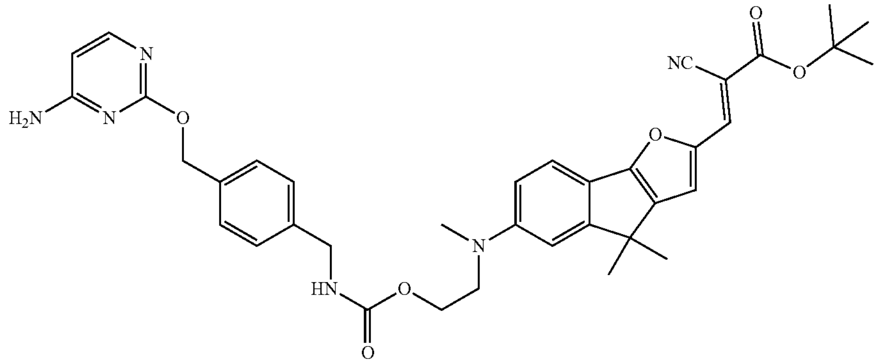
probe 30
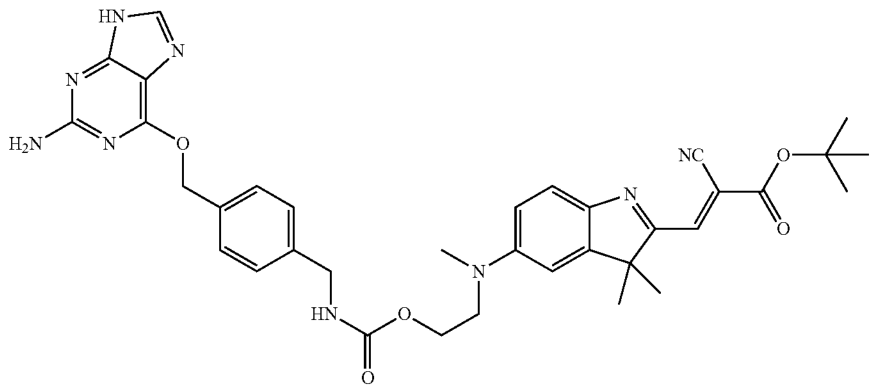
probe 31
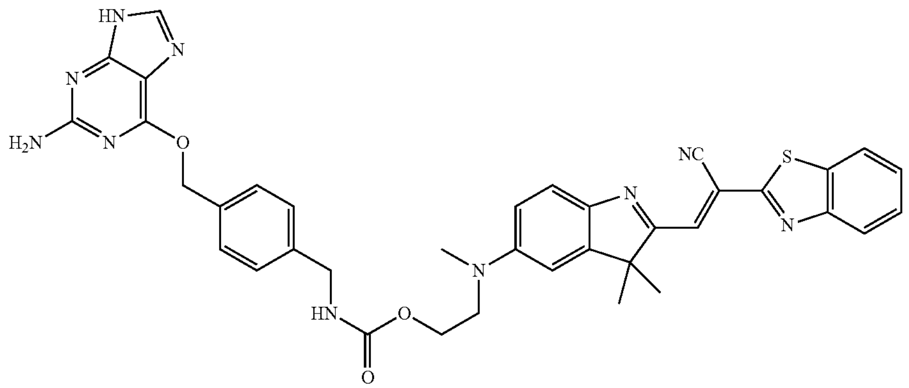
and -continued probe 32

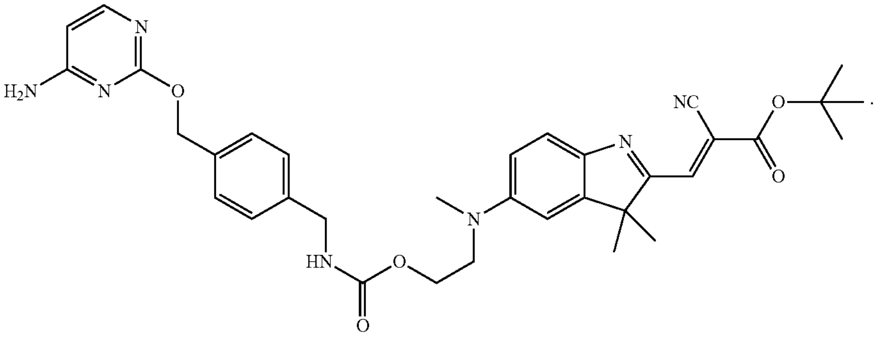

3. The fluorescent probe according to claim 1, wherein $X_1$ is a $C_{1-10}$ linear or branched alkyl group, and $X_2$ is a $C_{1-10}$ linear or branched chain alkylene group.

4. A probe kit comprising the fluorescent probe according to claim 1.

5. The probe kit according to claim 4, wherein, said probe kit further comprises a biocompatible medium.

6. The probe kit according to claim 5, wherein, said biocompatible medium is at least one selected from dimethyl sulfoxide, a buffer, and physiological saline.

7. The probe kit according to claim 6, wherein, said buffer includes phosphate buffer.

8. A fluorescent activated protein specific labeling method, comprising steps of:

contacting the fluorescent probe according to claim 1 with a target protein having a protein tag; and performing a labeling reaction between the fluorescent probe and the protein tag to label the protein tag with the fluorescent probe.

9. The fluorescent activated protein specific labeling method according to claim 8, wherein, the labeling of the protein tag with the fluorescent probe is covalently labeling; and a reaction medium of said labeling reaction is selected from a pure protein solution, a cell lysate and an in situ medium in which the target protein having a protein tag is located.

10. The fluorescent activated protein specific labeling method according to claim 9, wherein, the in situ medium is selected from intracellular media, organelle media, living tissue media, blood, and body fluids.

11. A method for quantification, detection or kinetic studies of proteins, or for imaging of cells, tissues, and living bodies, comprising a step of using the fluorescent probe of claim 1 to quantify proteins, detect proteins, or perform kinetic studies of proteins or to image cells, image tissues, or image living bodies.

* * * * *